(12) United States Patent  
Caroff et al.

(10) Patent No.: US 8,518,912 B2
(45) Date of Patent: Aug. 27, 2013

(54) PHOSPHONIC ACID DERIVATES AND THEIR USE AS P2Y$_{12}$ RECEPTOR ANTAGONISTS

(75) Inventors: Eva Caroff, Ranspach-le-Haut (FR); Kurt Hilpert, Hofstetten (CH); Francis Hubler, Hegenheim (FR); Emmanuel Meyer, Aarau (CH); Dorte Renneberg, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 314 days.

(21) Appl. No.: 12/745,358

(22) PCT Filed: Nov. 28, 2008

(86) PCT No.: PCT/IB2008/055002
§ 371 (c)(1),
(2), (4) Date: May 28, 2010

(87) PCT Pub. No.: WO2009/069100
PCT Pub. Date: Jun. 4, 2009

(65) Prior Publication Data
US 2010/0261678 A1  Oct. 14, 2010

(51) Int. Cl.
*A61K 31/675* (2006.01)
*C07F 9/06* (2006.01)

(52) U.S. Cl.
USPC ............................................ 514/86; 544/243

(58) Field of Classification Search
USPC ......................................... 514/86; 544/243
See application file for complete search history.

(56) References Cited

U.S. PATENT DOCUMENTS

| | | | |
|---|---|---|---|
| RE26,253 E | 8/1967 | Petisi et al. | |
| 3,338,963 A | 8/1967 | Patisi et al. | |
| 3,341,585 A | 9/1967 | Bitha et al. | |
| 3,345,410 A | 10/1967 | Winterbottom et al. | |
| 3,373,196 A | 3/1968 | Bitha and Hlavka | |
| 3,518,306 A | 6/1970 | Martell Jr., et al. | |
| 3,579,579 A | 5/1971 | Hlavka et al. | |
| 5,281,628 A | 1/1994 | Hlavka et al. | |
| 5,284,963 A | 2/1994 | Sum et al. | |
| 5,326,759 A | 7/1994 | Hlavka et al. | |
| 5,328,902 A | 7/1994 | Sum et al. | |
| 5,380,888 A | 1/1995 | Sum et al. | |
| 5,401,729 A | 3/1995 | Sum et al. | |
| 5,401,863 A | 3/1995 | Hlavka et al. | |
| 5,466,684 A | 11/1995 | Sum et al. | |
| 3,226,436 A | 12/1995 | Petisi et al. | |
| 5,494,903 A | 2/1996 | Hlavka et al. | |
| 5,495,018 A | 2/1996 | Sum et al. | |
| 5,495,031 A | 2/1996 | Sum et al. | |
| 5,529,990 A | 6/1996 | Hlavka et al. | |
| 5,530,117 A | 6/1996 | Hlavka et al. | |
| 6,258,822 B1 | 7/2001 | Geyer et al. | |
| 6,617,318 B1 | 9/2003 | Nelson et al. | |
| 6,624,168 B2 | 9/2003 | Nelson et al. | |
| 6,642,270 B2 | 11/2003 | Nelson et al. | |
| 6,683,068 B2 | 1/2004 | Nelson et al. | |
| 6,816,635 B2 | 11/2004 | Nelson et al. | |
| 6,818,634 B2 | 11/2004 | Nelson et al. | |
| 6,833,365 B2 | 12/2004 | Levy et al. | |
| 6,841,546 B2 | 1/2005 | Draper et al. | |
| 6,846,939 B2 | 1/2005 | Nelson et al. | |
| 6,855,715 B1 | 2/2005 | Liebeschuetz et al. | |
| 7,001,918 B2 | 2/2006 | Huss et al. | |
| 7,045,507 B2 | 5/2006 | Draper et al. | |
| 7,056,902 B2 | 6/2006 | Nelson et al. | |
| 7,067,681 B2 | 6/2006 | Nelson et al. | |

(Continued)

FOREIGN PATENT DOCUMENTS

| EP | 0407200 | 1/1991 |
|---|---|---|
| EP | 0535346 | 4/1993 |

(Continued)

OTHER PUBLICATIONS

Barden, Timothy C. et al, "Glycylcylines'3. 9-Aminodoxycyclinecarboxamides," *J. Med. Chem.*, vol. 37:3205-3211 (1994).

Sum, Phaik-Eng et al, "Synthesis and Structure—Activity Relationship of Novel Glycylcydine Derivatives Leading to the Discovery of GAR-936," *Bioorganic & Medicinal Chemistry Letters*, vol.9:1459-1462 (1999).

Sum, Phaik-Eng et al, "Glycylcyclines 1. A New Generation of Potent Antibacterial Agents through Modification of 9-Aminotetracyclines," *J. Med. Chem.*, vol. 37:184-188 (1994).

Parlow, J.J. et al, "Piperazinyl glutamate pyridines as potent orally bioavailable P2Y$_{12}$ antagonists for inhibition of platelet aggregation," *J. Med. Chem.*, 2010, 53, 2010-2037.

Alpegiano, M., et al., "On the Preparation of 4-Hydroxymethyl-5-Methyl-1, 3- Dioxol-2-One", Synthetic Communications, vol. 22(9), pp. 1277-1282, (1992).

(Continued)

*Primary Examiner* — James O Wilson
*Assistant Examiner* — Ebenezer O Sackey
(74) *Attorney, Agent, or Firm* — Hoxie & Associates, LLC

(57) ABSTRACT

The invention relates to 2-phenyl-pyrimidine derivatives containing a phosphonic acid motif and their use as P2Y$_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals. (I).

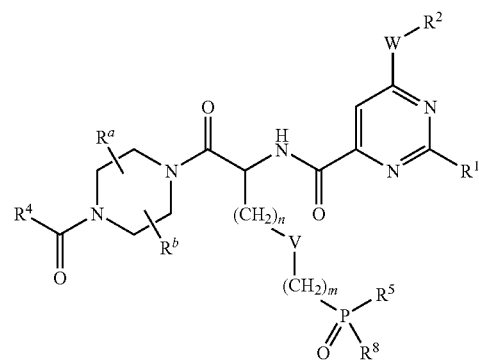

39 Claims, No Drawings

(56) References Cited

U.S. PATENT DOCUMENTS

| | | | |
|---|---|---|---|
| 8,058,263 B2 * | 11/2011 | Caroff et al. ............. 514/85 | |
| 8,067,419 B2 | 11/2011 | Binkert et al. | |
| 2002/0123637 A1 | 9/2002 | Levy et al. | |
| 2002/0128237 A1 | 9/2002 | Nelson et al. | |
| 2002/0128238 A1 | 9/2002 | Nelson et al. | |
| 2002/0132798 A1 | 9/2002 | Nelson et al. | |
| 2003/0060474 A1 | 3/2003 | Bryant et al. | |
| 2004/0048835 A1 | 3/2004 | Nelson et al. | |
| 2004/0063674 A1 | 4/2004 | Levy et al. | |
| 2004/0092490 A1 | 5/2004 | Draper et al. | |
| 2004/0138183 A1 | 7/2004 | Nelson et al. | |
| 2004/0152674 A1 | 8/2004 | Levy et al. | |
| 2004/0176334 A1 | 9/2004 | Nelson et al. | |
| 2004/0214800 A1 | 10/2004 | Levy et al. | |
| 2004/0214801 A1 | 10/2004 | Nelson et al. | |
| 2004/0242548 A1 | 12/2004 | Draper et al. | |
| 2005/0020545 A1 | 1/2005 | Draper et al. | |
| 2005/0026875 A1 | 2/2005 | Nelson et al. | |
| 2005/0026876 A1 | 2/2005 | Nelson et al. | |
| 2005/0038002 A1 | 2/2005 | Nelson et al. | |
| 2005/0038037 A1 | 2/2005 | Bryant et al. | |
| 2005/0065163 A1 | 3/2005 | Bryant et al. | |
| 2005/0070510 A1 | 3/2005 | Draper et al. | |
| 2005/0119235 A1 | 6/2005 | Nelson et al. | |
| 2005/0137174 A1 | 6/2005 | Ohemeng et al. | |
| 2005/0143352 A1 | 6/2005 | Nelson et al. | |
| 2005/0148551 A1 | 7/2005 | Nelson et al. | |
| 2005/0187198 A1 | 8/2005 | Nelson et al. | |
| 2005/0215532 A1 | 9/2005 | Levy et al. | |
| 2005/0250744 A1 | 11/2005 | Levy et al. | |
| 2005/0282767 A1 | 12/2005 | Myers et al. | |
| 2006/0003971 A1 | 1/2006 | Nelson | |
| 2006/0008463 A1 | 1/2006 | Itoh et al. | |
| 2006/0008933 A1 | 1/2006 | Muller et al. | |
| 2006/0014876 A1 | 1/2006 | Bushelman et al. | |
| 2008/0194576 A1 | 8/2008 | Caroff et al. | |
| 2008/0234272 A1 | 9/2008 | Binkert et al. | |
| 2011/0028484 A1 | 2/2011 | Caroff et al. | |
| 2011/0046089 A1 | 2/2011 | Caroff et al. | |
| 2012/0053149 A1 | 3/2012 | Caroff et al. | |

FOREIGN PATENT DOCUMENTS

| | | |
|---|---|---|
| EP | 0536515 | 4/1993 |
| EP | 0582790 | 1/1994 |
| EP | 058289 | 2/1994 |
| GB | 921252 | 3/1963 |
| GB | 1469384 | 4/1977 |
| JP | 5373586 | 6/1978 |
| JP | 53073586 | 6/1978 |
| WO | WO-99/37306 A1 | 7/1999 |
| WO | WO-00/28983 A1 | 5/2000 |
| WO | WO-01/19784 A1 | 3/2001 |
| WO | WO 02/098856 | 12/2002 |
| WO | WO 2004/052366 | 6/2004 |
| WO | WO 2004/092189 | 10/2004 |
| WO | WO 2006/114774 | 11/2006 |
| WO | WO 2008/044217 | 4/2008 |
| WO | WO 2008/050301 | 5/2008 |
| WO | WO 2008/128647 | 10/2008 |
| WO | WO 2009/080226 | 7/2009 |
| WO | WO 2009/080227 | 7/2009 |
| WO | WO 2009/125365 | 10/2009 |
| WO | WO 2009/125366 | 10/2009 |
| WO | WO 2010/116328 | 10/2010 |
| WO | WO 2010/122504 | 10/2010 |

OTHER PUBLICATIONS

Born, G.V.R., et al., "The Aggregation of Blood Platelets", J. Physiol., vol. 168, pp. 178-195, (1963).
Furstner, a., et al., "Iron-Catalyzed Cross-Coupling Reactions", J. Am. Chem. Soc., vol. 124, pp. 13856-13863, (2002).
Gould, P.L., "Salt Selection for Basic Drugs", International Journal of Pharmaceutics, vol. 33, pp. 201-217, (1986).
Iyer, R.P., et al., "Synthesis of Iodoalkylacylates and their Use in the Preparation of S-Alkyl Phosphorothiolates", Synthetic Communications, vol. 25(18), pp. 2739-2749, (1995).
Parlow, J.J., et al., "Piperazinyl-glutamate-pyridines as Potent Orally Bioavailble P2Y12 Antagonists for Inhibition of Platelet Aggregation", Bioorganic & Medicinal Chemistry Letters, vol. 19, pp. 4657-4663, (2009).
Parlow, J.J., et al., "Piperazinyl-glutamate-pyrimidines as Potent P2Y12 Antagonists for Inhibition of Platelet Aggregation", Bioorganic & Medicinal Chemistry Letters, vol. 19, pp. 6148-6156, (2009).
Remington, The Science and Practice of Pharmacy, $21^{st}$ Edition (2005), Part 5, "Pharmaceutical Manufacturing" [published by Lippincott Williams & Wilkins].
Sun, C.Q., et al., "A General Synthesis of Dioxolenone Prodrug Moieties", Tetrahedron Letters, vol. 43, pp. 1161-1164, (2002).
Amir et al., "Treatment of Thrombotic Thrombocytopenic Pupura with Anti Platelet Drugs", Blood, vol. 42, No. 1, pp. 27-33, Jul. 1973.
Antithrombotic Trialists' Collaboration, "Collaborative Meta-Analysis of Randomised Trials of Anti Platelet Therapy for Prevention of Death, Myocardial Infarction, and Stroke in High Risk Patients", British Medical Journal, vol. 324, pp. 71-86, 2002.
Balduini et al., "Platelet Aggregation in Platelet-Rich Plasma and Whole Blood in 120 Patients with Myeloproliferative Disorders", Coagulation and Transfusion Medicine, vol. 95, No. 1, pp. 82-86, Jan. 1991.
Bartoli et al., "Reaction of Dianions of Acyclic B-Enamino Ketones with Electrophiles. 3. Nitriles: Synthesis of Pyridine and Pyrimidine Derivatives", J. Org. Chem., vol. 57, pp. 6020-6025, 1992.
Blanger et al., "New Approach to Aphidicolin and Total Asymmetric Synthesis of Unnatural (11R)-(-)- 8-Epi-11-hydroxyaphidicolin by Tandem Transannular Diels—Alder/Aldol Reactions", J. Org. Chem., vol. 65, pp. 7070-7074, 2000.
Bertrand, "Randomized Multicenter Comparison of Conventional Anticoagulation Versus Antiplatelet Therapy in Unplanned and Elective Coronary Stenting", Circulation, vol. 98, pp. 1597-1603, 1998.
Brighton et al., "Antiphospholipid Antibodies and Thrombosis", Bailliere's Clinical Haematology, vol. 7, No. 3, pp. 541-557, Sep. 1994.
Caprie Steering Committee, "A Randomized, Blinded, Trial of Clopidogrel Versus Aspirin in Patients at Risk of Ischaemic Events (CAPRIE)", The Lancet, vol. 348, pp. 1329-1339, Nov. 16, 1996.
Charette, et al., "Enantioselective Cyclopropanation of Allylic Alcohols with Dioxaborolane Ligands: Scope and Synthetic Applications", J. Am. Chem. Soc., vol. 120, pp. 11943-11952, 1998.
Collins et al., "Review Article: Platelets in Inflammatory Bowel Diease-Pathogenic Role and Therapeutic Implications", Aliment Pharmacal. Ther., vol. 11, pp. 237-247, 1997.
Database Chemcats, Chemical Abstracts Service, Columbus, OH, USA; XP002420714; Order Number (ON) CGX-3221820; 2005.
Database Chemcats, Chemical Abstracts Service, Columbus, OH, USA; XP002420715; Order Number (ON): 15569369, 15467386; 2006.
Davies et al., "Intramyocardial Platelet Aggregation in Patients with Unstable Angina Suffering Sudden Ischemic Cardiac Death", Pathophysiology and Natural History- Platelets, Circulation, vol. 73, No. 3, pp. 418-427, 1986.
Felfernig-Boehm et al., "Early Detection of Preeclampsia by Determination of Platelet Aggregability", Thrombosis Research, vol. 98, pp. 139-146, 2000.
Feokistov et al., "Adenosine A2B Receptors, Pharmacological Reviews", vol. 49, No. 4, pp. 381-402, 1997.
Fox et al., "Benefits and Risks of the Combination of Ciopidogrel and Aspirin in Patients Undergoing Surgical Revascularization for Non-ST-Elevation Acute Coronary Syndrome: The Clidogrel in Unstable Angina to Prevent Recurrent Ischemic Events (CURE) Trial", Circulation, vol. 110, pp. 1202-1208, 2004.
Halushka et al., "Protective Effects of Aspirin in Endotoxic Shock", The Journal of Pharmacology and Experimental Therapeutics, vol. 218, No. 2, pp. 464-469, 1981.
Hovens et al., "Aspirin in the Prevention and Treatment of Venous Thromboembolism", Journal of Thrombosis and Haemostasis, vol. 4, pp. 1470-1475, 2006.

Iyer et al., "Synthesis of Iodoalkylacylates and Their Use in the Preparation of S-Alkyl Phosphorothiolates", Synthetic Communications, vol. 25, No. 18, pp. 2739-2749, 1995.

Kharbanda et al., "Prevention of Inflammation-Induced Endothelial Dysfunction: A Novel Vasculo-Protective Action of Aspirin", Circulation, vol. 105, pp. 2600-2604, 2002.

Megalopoulos Etal., "Recurrent Arterial Thromboses in a Woman with Heparin Induced Thrombocytopenia, Successfully Managed with Iloprost Followed by Clopidogrel. An Alternative Therapeutic Option for Heparin Induced Thrombocytopenia Type II Syndrome", International Angiology, vol. 25, No. 1, pp. 84-89, Mar. 2006.

Mehta et al., "Effects of Pretreatment with Clopidogrel and Aspirin Followed by Long-Term Therapy in Patients Undergoing Percutaneous Coronary Intervention: The PCI-CURE Study", The Lancet, vol. 358, pp. 527-533, Aug. 18, 2001.

Nogard, "Cangretor: A Novel PsY12 Receptor Antagonist", Expert Opinion, Invest.Drugs, vol. 18, No. 8, pp. 1219-1230, 2009.

Notice of Allowance dated Jun. 27, 2011, for U.S. Appl. No. 12/936,661.

Office Action dated Aug. 31, 2012, for U.S. Appl. No. 12/936,664.
Office Action dated Jan. 21, 2011, for U.S. Appl. No. 12/936,661.
Office Action dated Jan. 19, 2011, for U.S. Appl. No. 12/445,352.
Office Action dated Oct. 28, 2010, U.S. Appl. No. 11/912,545.

Payne et al., "Beneficial Effects of Clopidogrel Combined with Aspirin in Reducing Cerebral Emboli in Patients Undergoing Carotid Endarterectomy", Circulation, vol. 109, pp. 1476-1481, 2004.

Shao Etal., "Phenoxyphenyl Pyridines as Novel State-Dependent, High-Potency Sodium Channel Inhibitors", J. Med. Chem., vol. 47, pp. 4277-4285, 2004.

Sheppard et al, "Discovery and Optimization of Anthranilic Acid Sulfonamides as Inhibitors of Methionine Aminopeptidase-2: A Structural Basis for the Reduction of Albumin Binding", J. Med. Chem., vol. 49, pp. 3832-3849, 2006.

Stathakis et al., "Platelet Dysfunction in Essential Thrombocythaemia", Annals of Clinical Research, vol. 6, pp. 198-202, 1974.

Thorsen et al., "The Treatment of the Hemolytic-Uremic Syndrome with Inhibitors of Platelet Function", The American Journal of Medicine, vol. 66, pp. 711-716, Apr. 1979.

Triadou et al., "Platelet Function in Sickle Cell Disease During Steady State", Nouvelle Revue Francaise Hematologic, vol. 32, pp. 137-142, 1990.

University of Perugia, "Aspirin for the Prevention of Recurrent Venous Thromboembolism and Cardiovascular Events", pp. 1-3, ClinicalTrials.gov/ct/show/NCT002226 77, Sep. 13, 2005.

Yao et al., "Clopidogrel is More Effective Than Aspirin as Adjuvant Treatment to Prevent Reocclusion After Thrombolysis", Am. J. Physiol., vol. 267, pp. H488-H493, 1994.

* cited by examiner

PHOSPHONIC ACID DERIVATES AND THEIR USE AS P2Y$_{12}$ RECEPTOR ANTAGONISTS

CROSS REFERENCE TO RELATED APPLICATIONS

This application is a United States National Stage Application under 35 USC §371 of PCT/IB2008/055002 filed Nov. 28, 2008, which claims the benefit of PCT/IB2007/054850, filed Nov. 29, 2007.

FIELD OF THE INVENTION

The present invention relates to certain phosphonic acid derivatives and their use as P2Y$_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

BACKGROUND OF THE INVENTION

Haemostasis is referred to as the natural balance of maintaining the fluidity of the blood in the vascular system and preventing excessive blood loss subsequent to blood vessel injury by rapid formation of a solid blood clot. After vascular damage, contraction of the vessels and platelet adhesion occur immediately followed by aggregation of the platelets, activation of the coagulation cascade and finally also of the fibrinolytic system. Haemostatic abnormalities can lead to excessive bleeding or thrombosis, both life-threatening situations.

A series of antiplatelet agents have been developed over the past several years based on different mechanisms of action. The most widely used agent in antiplatelet therapy is aspirin, which irreversibly inhibits cyclooxygenase-1 and thereby affecting the thromboxane pathway. Although not optimally efficacious, treatment with aspirin remains the standard therapy against which new therapeutics are compared and judged.

Other drugs like the phosphodiesterase inhibitors dipyridamole and cilostazol, as well as the vitamin K antagonists (warfarin), are marketed but do not show all desirable features for such drugs. Three intravenously applicable, potent GPIIb/IIIa receptor antagonists (abciximab, eptifibatide, and tirofiban) blocking platelet aggregation are available on the market. Besides, some orally active GPIIb/IIIa antagonists (e.g. sibrafiban, xemilofiban or orbofiban) have not been successful in clinical development so far.

Adenosine 5'-diphosphate (ADP) is a key mediator in platelet activation and aggregation interfering with two platelet ADP receptors P2Y$_1$ and P2Y$_{12}$.

Antagonists of the platelet ADP receptor have been identified and display inhibition of platelet aggregation and anti-thrombotic activity. The most effective antagonists known so far are the thienopyridines ticlopidine, clopidogrel and CS-747, which have been used clinically as antithrombotic agents. It could be shown that these drugs, via their reactive metabolites, irreversibly block the ADP receptor subtype P2Y$_{12}$.

Some P2Y$_{12}$ antagonists like AR-C69931MX (Cangrelor) or AZD6140 have reached phase II clinical studies. These inhibitors are selective platelet ADP receptor antagonists, which inhibit ADP-dependent platelet aggregation, and are effective in vivo.

Piperazino-carbonylmethylaminocarbonyl-naphtyl or -quinolyl derivatives have been described as ADP receptor antagonists in WO 02/098856 and WO 2004/052366.

WO 2006/114774 describes 2-phenyl-4-(carbonylmethylaminocarbonyl)-pyrimidine derivatives as P2Y$_{12}$ receptor antagonists. However these compounds do not contain any phosphonic acid or phosphonate motif.

DESCRIPTION OF THE INVENTION

The inventors have now found that the phosphonic acid derivatives according to the present invention surprisingly show significantly improved biological properties compared to the corresponding carboxylic acid derivatives previously known to one skilled in the art.

Various embodiments of the invention are presented hereafter:

1) The present invention firstly relates to the compounds of formula I

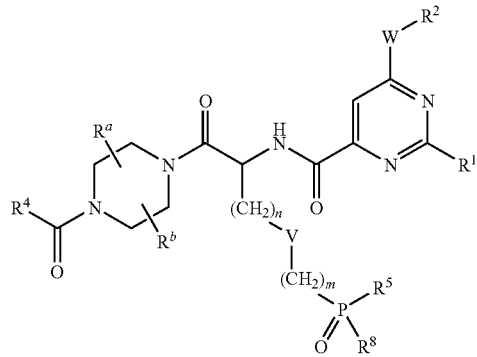

formula I wherein

R$^1$ represents phenyl, wherein the phenyl is unsubstituted or substituted 1 to 3 times (preferably unsubstituted or substituted once or twice, more preferably unsubstituted or substituted once and most preferably unsubstituted) by substituents each independently selected from the group consisting of halogen, methyl, methoxy, trifluoromethyl and trifluoromethoxy;

W represents a bond, and R$^2$ represents alkyl, hydroxyalkyl, alkoxyalkyl, cycloalkyl, aryl or heteroaryl; or W represents —O— and R$^2$ represents alkyl, cycloalkyl, hydroxyalkyl or heterocyclyl; or W represents —NR$^3$—, R$^2$ represents alkyl, alkoxycarbonylalkyl, carboxyalkyl, hydroxyalkyl, alkoxyalkyl, heterocyclyl, cycloalkyl, aryl or aralkyl and R$^3$ represents hydrogen or alkyl; or W represents —NR$^3$— and R$^2$ and R$^3$ form, together with the nitrogen that carries them, a heterocyclic ring of 4 to 7 members wherein the members needed to complete said heterocyclic ring are each independently selected from —CH$_2$—, —CHR$^x$—, —O—, —S—, —CO— and —NR$^y$—, it being understood however that said heterocyclic ring does not contain more than one member selected from the group consisting of —CHR$^x$—, —O—, —S—, —CO— and —NR$^y$—, R$^x$ representing hydroxy, hydroxymethyl, alkoxymethyl or alkoxy and R$^y$ representing hydrogen or alkyl;

or W represents —NR$^3$— and R$^2$ and R$^3$ form, together with the nitrogen that carries them, an imidazolyl, pyrazolyl, 1,2,3-triazolyl or 1,2,4-triazolyl ring, which ring may be substituted by an alkyl group (especially by a methyl group);

$R^a$ represents hydrogen or methyl;
$R^b$ represents hydrogen or methyl;
$R^4$ represents alkoxy;
n represents 0, 1, 2 or 3, V represents a bond, and m represents 0; or
n represents 0 or 1, V represents phenyl, and m represents 0; or
n represents 1, V represents phenyl, and m represents 1;
$R^5$ and $R^8$ are identical and represent each hydroxy, unsubstituted phenyloxy, unsubstituted benzyloxy, a group —O—(CHR$^6$)—O—C(=O)—R$^7$, a group —O—(CHR$^6$)—O—C(=O)—O—R$^7$, a group —O—(CHR$^6$)—C(=O)—O—R$^9$, a group —NH—(CHR$^{10}$)—C(=O)—O—R$^9$ or a group —NH—C(CH$_3$)$_2$—C(=O)—O—R$^9$; or
$R^5$ represents hydroxy or unsubstituted phenyloxy, and $R^8$ represents a group —O—(CH$_2$)—O—C(=O)—R$^9$ or a group —NH—CH(CH$_3$)—C(=O)—O—R$^9$; or
P(O)R$^5$R$^8$ represents a group selected from the following structures

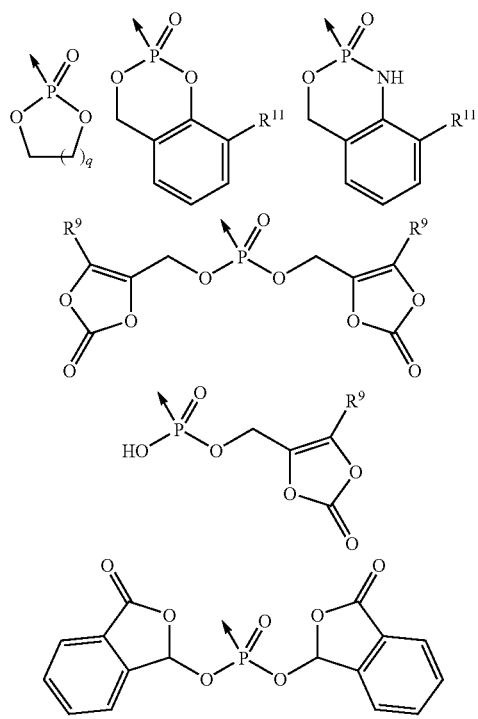

wherein the arrow marks the point of attachment to the remaining part of compounds of formula I;
q represents 1 or 2;
$R^6$ represents hydrogen or (C$_1$-C$_3$)alkyl;
$R^7$ represents (C$_1$-C$_4$)alkyl or unsubstituted (C$_3$-C$_6$)cycloalkyl;
$R^9$ represents (C$_1$-C$_4$)alkyl;
$R^{10}$ represents hydrogen, (C$_1$-C$_4$)alkyl, unsubstituted phenyl or unsubstituted benzyl;
$R^{11}$ represents hydrogen, (C$_1$-C$_4$)alkyl or (C$_1$-C$_4$)alkoxy;
and to the salts (in particular pharmaceutically acceptable salts) of such compounds.

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art.

The compounds of formula I are P2Y$_{12}$ receptor antagonists. Accordingly, they are useful in therapy (including combination therapy), where they can be widely used as inhibitors of platelet activation, aggregation and degranulation, as promoters of platelet disaggregation or as anti-thrombotic agents.

The following paragraphs provide definitions of the various chemical moieties for the compounds according to the invention. Said definitions are intended to apply uniformly throughout the specification and claims unless an otherwise expressly set out definition provides a broader or narrower definition.

The term "halogen" refers to fluorine, chlorine, bromine or iodine, preferably to fluorine, chlorine or bromine and more preferably to fluorine.

The term "alkyl", used alone or in combination, refers to a saturated straight or branched chain alkyl group containing 1 to 7 carbon atoms (e.g. methyl, ethyl, n-propyl, iso-propyl, n-butyl, iso-butyl, sec-butyl, tert-butyl, n-pentyl, neopentyl, iso-pentyl, n-hexyl, iso-hexyl, n-heptyl or iso-heptyl), and preferably 1 to 4 carbon atoms. Representative examples of preferred alkyl groups include methyl, ethyl, n-propyl, iso-propyl, n-butyl, iso-butyl, sec-butyl and tert-butyl. The term "(C$_x$-C$_y$)alkyl" (x and y being integers) refers to a straight or branched chain alkyl group containing x to y carbon atoms.

The term "alkoxy", used alone or in combination, refers to a saturated straight or branched chain alkoxy group containing 1 to 6 carbon atoms (e.g. methoxy, ethoxy, n-propoxy, iso-propoxy, n-butoxy, iso-butoxy, sec-butoxy, tert-butoxy, n-pentoxy, neopentyloxy, iso-pentyloxy, n-hexyloxy or iso-hexyloxy), and preferably 1 to 4 carbon atoms. Representative examples of preferred alkoxy groups include methoxy, ethoxy, n-propoxy, iso-propoxy, n-butoxy, iso-butoxy, sec-butoxy and tert-butoxy. The term "(C$_x$-C$_y$)alkoxy" (x and y being integers) refers to a straight or branched chain alkoxy group containing x to y carbon atoms.

The term "hydroxyalkyl", as used herein, refers to an alkyl group as previously defined wherein one hydrogen atom has been replaced by a hydroxy (i.e. —OH) group. Examples of hydroxyalkyl groups include, but are not limited to, hydroxymethyl, 2-hydroxy-ethyl, 2-hydroxy-propyl, 2-hydroxy-1-methyl-ethyl, 2-hydroxy-1,1-dimethyl-ethyl, 1-hydroxy-propyl, 3-hydroxy-propyl, 1-hydroxy-butyl, 3-hydroxy-butyl, 4-hydroxy-butyl, 3-hydroxy-pentyl and 3-hydroxy-3-methyl-butyl (and preferably hydroxymethyl, 2-hydroxy-ethyl and 3-hydroxy-butyl).

The term "alkoxyalkyl", as used herein, refers to an alkyl group as previously defined wherein one hydrogen atom has been replaced by an alkoxy group as previously defined. Examples of alkoxyalkyl groups include, but are not limited to, 3-methoxy-propyl, methoxymethyl and 2-methoxy-ethyl (and notably methoxymethyl and 2-methoxy-ethyl). In analogy, the term "alkoxymethyl" means for example methoxymethyl or 2-methoxy-ethyl.

The term "cycloalkyl", as used herein, alone or in any combination, refers to a saturated cyclic hydrocarbon moiety containing 3 to 7 carbon atoms which may be unsubstituted or substituted once by hydroxy, hydroxymethyl, alkoxymethyl (preferably methoxymethyl or ethoxymethyl and more preferably methoxymethyl) or alkoxy (preferably methoxy or ethoxy and more preferably methoxy). Representative examples of cycloalkyl groups include, but are not limited to, cyclopropyl, cyclobutyl, cyclopentyl, cyclohexyl, 4-hydroxy-cyclohexyl, 2-hydroxy-cyclohexyl, 2-hydroxymethyl-cyclopropyl and 2-methoxymethyl-cyclopropyl (in particular cyclopropyl, 2-hydroxymethyl-cyclopropyl and 2-methoxymethyl-cyclopropyl).

The term "alkoxycarbonylalkyl" refers to an alkyl group as previously defined wherein one hydrogen atom has been replaced by an alkoxycarbonyl group, that is, a —C(=O)— group itself substituted by an alkoxy group as previously defined. Representative examples of alkoxycarbonylalkyl groups include, but are not limited to, 2-ethoxycarbonyl-ethyl and 2-methoxycarbonyl-ethyl.

The term "carboxyalkyl" refers to an alkyl group as previously defined wherein one hydrogen atom has been replaced by a carboxy group (that is, by a —COOH group). Representative examples of carboxyalkyl groups include, but are not limited to, 2-carboxy-ethyl and 3-carboxy-propyl.

The term "aryl" refers to an aromatic cyclic group with one, two or three rings, having from 6 to 14 carbon ring-atoms and preferably from 6 to 10 carbon ring-atoms, for example to phenyl or naphthyl groups (and notably to phenyl groups). Any aryl group (and in particular any phenyl group) as defined herein may be unsubstituted or substituted with one, two or more substituents (preferably with one to three substituents, more preferably with one or two substituents and notably with one substituent), each independently selected from the group consisting of halogen, alkyl and alkoxy. Specific examples of aryl groups are phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2,4-difluorophenyl, 3,4-difluorophenyl, 2,4-dimethoxyphenyl and 2,4-dimethylphenyl (preferably phenyl and 4-methoxyphenyl).

The term "aralkyl", as used herein, alone or in any combination, refers to an aryl group appended to the parent molecular moiety through an alkyl group wherein however the aryl group may be unsubstituted or substituted with 1 to 3 substituents selected independently from the group consisting of halogen, alkyl and alkoxy. Representative examples of aralkyl groups include, but are not limited to, benzyl, 2-phenylethyl, 3-phenylpropyl and 2-naphth-2-ylethyl. Preferred aralkyl groups are the phenylalkyl groups.

The term "phenylalkyl", as used herein, alone or in any combination, refers to an unsubstituted phenyl group appended to the parent molecular moiety through an alkyl group. Representative examples of phenylalkyl groups include, but are not limited to, benzyl, 2-phenylethyl and 3-phenylpropyl. Preferred is benzyl.

The term "heteroaryl", as used herein, alone or in combination, refers to a mono-, bi- or tricyclic aromatic ring system containing up to 14 ring atoms wherein at least one of the rings contains at least one heteroatom independently selected from the group consisting of nitrogen, oxygen and sulfur; in addition, the term "heteroaryl" may also refer to 1-oxy-pyridinyl groups. The heteroaryl group can be unsubstituted or substituted with 1 to 3 substituents (preferably 1 to 2 substituents and more preferably 1 substituent) selected independently from the group consisting of halogen, alkyl, alkoxy, trifluoromethyl and trifluoromethoxy. Representative examples of heteroaryl groups include, but are not limited to, thienyl, furanyl, pyrrolyl, pyrazolyl, thiazolyl, imidazolyl, oxazolyl, pyridinyl, 1-oxy-4-pyridinyl, 1-oxy-3-pyridinyl, 1-oxy-2-pyridinyl, pyrimidinyl, quinolinyl, benzimidazolyl, benzothiazolyl, benzothienyl, benzoxazolyl, benzofuranyl, indolyl, carbazolyl, phenothiazinyl and phenoxazinyl (preferably thienyl, pyrazolyl and 4-methyl-pyrazolyl).

The term "monocyclic heteroaryl", as used herein, refers to a monocyclic aromatic ring system containing 5 or 6 ring atoms among which 1 or 2 may be heteroatoms selected from O, N and S. The monocyclic heteroaryl group can be unsubstituted or substituted with 1 to 2 substituents (preferably 1 substituent) selected independently from the group consisting of halogen, alkyl, alkoxy, trifluoromethyl and trifluoromethoxy. Representative examples of monocyclic heteroaryl groups include, but are not limited to, thienyl, furanyl, pyrrolyl, pyrazolyl, thiazolyl, imidazolyl, oxazolyl, pyridinyl and pyrimidinyl.

The term "heterocyclyl", as used herein, alone or in any combination, refers to an unsubstituted saturated monocyclic moiety of 3 to 7 ring members containing 1 to 2 heteroatoms selected from nitrogen, oxygen and sulfur, it being however understood that (i) a heterocyclyl group is not attached to the rest of the molecule by a nitrogen atom, (ii) a heterocyclyl group of 3 or 4 ring members contains only one heteroatom which is a nitrogen atom and (iii) a heterocyclyl group does not contain 2 sulfur atoms. The sulfur atom of a heterocyclyl group may be in an oxidised form, i.e. as a sulfoxide or sulfonyl. Representative examples of heterocyclyl groups include, but are not limited to, azetidinyl, pyrrolidinyl, tetrahydrofuranyl, piperidinyl, piperazinyl, morpholinyl and thiomorpholinyl (preferably tetrahydrofuran-3-yl).

In this patent application, variably attached bonds may be used for substituents or groups. In such case it is meant that the substituent or group is attached to either atom linked by the bond into which the variably attached bond is drawn into. For example, the compound drawn below

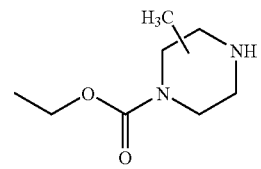

is either 2-methyl-piperazine-1-carboxylic acid ethyl ester or 3-methyl-piperazine-1-carboxylic acid ethyl ester.

Besides, the following paragraphs provide definitions of various other terms. Said definitions are intended to apply uniformly throughout the specification and claims unless an otherwise expressly set out definition provides a broader or narrower definition.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively the term "around") placed before a temperature "Y" refers in the current application to an interval extending from the temperature Y minus 10° C. to Y plus 10° C., and preferably to an interval extending from Y minus 5° C. to Y plus 5° C.

2) In particular, the invention relates to compounds of formula I that are also compounds of formula $I_{CE}$

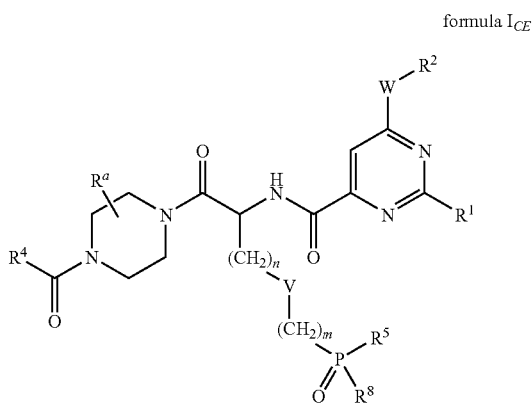

formula $I_{CE}$ wherein $R^1$ represents phenyl, wherein the phenyl is unsubstituted or monosubstituted with halogen, methyl or trifluoromethyl;

W represents a bond, and $R^2$ represents alkyl, hydroxyalkyl (notably 3-hydroxy-butyl), alkoxyalkyl (notably 3-methoxy-propyl), a cycloalkyl group of 3 to 7 carbon atoms (preferably of 3 to 6, more preferably of 3 to 5 carbon atoms and most preferably of 3 carbon atoms) which may be substituted once by hydroxymethyl or alkoxymethyl (preferably methoxymethyl or ethoxymethyl and more preferably methoxymethyl), a phenyl group which is unsubstituted or monosubstituted with alkoxy, or an unsubstituted monocyclic heteroaryl group; or W represents —O— and $R^2$ represents alkyl (notably methyl), cycloalkyl (notably cyclopentyl), hydroxyalkyl (notably 2-hydroxyethyl) or heterocyclyl (notably tetrahydrofuran-3-yl); or W represents —$NR^3$—, $R^2$ represents alkyl, alkoxycarbonylalkyl [notably 2-(ethoxycarbonyl)-ethyl], carboxyalkyl (notably 2-carboxy-ethyl), hydroxyalkyl (notably 2-hydroxy-ethyl), alkoxyalkyl, heterocyclyl (notably teterahydrofuran-3-yl), cycloalkyl (notably cyclopropyl), phenyl or phenylalkyl (notably benzyl) and $R^3$ represents hydrogen or alkyl (notably methyl); or W represents —$NR^3$— and $R^2$ and $R^3$ form, together with the nitrogen that carries them, a heterocyclic ring of 4 to 7 members (preferably 4 to 6 members) wherein the members needed to complete said heterocyclic ring are each independently selected from —$CH_2$—, —$CHR^x$—, —O— and —$NR^y$—, it being understood however that said heterocyclic ring does not contain more than one member selected from the group consisting of —$CHR^x$—, —O— and —$NR^y$—, $R^x$ representing hydroxy, hydroxymethyl, alkoxymethyl (notably methoxymethyl) or alkoxy (notably methoxy) and $R^y$ representing alkyl (especially methyl);

or W represents —$NR^3$— and $R^2$ and $R^3$ form, together with the nitrogen that carries them, a pyrazolyl ring which may be unsubstituted or monosubstituted by an alkyl group (especially by a methyl group);

$R^a$ represents hydrogen or methyl;

$R^4$ represents alkoxy (preferably ethoxy or n-butoxy);

n represents 0, 1, 2 or 3, V represents a bond, and m represents 0; or n represents 0 or 1, V represents phenyl, and m represents 0; or n represents 1, V represents phenyl, and m represents 1;

$R^5$ and $R^8$ are identical and represent each hydroxy, unsubstituted phenyloxy, unsubstituted benzyloxy, a group —O—($CHR^6$)—O—C(=O)—$R^7$, a group —O—($CHR^6$)—O—C(=O)—O—$R^7$, a group —O—($CHR^6$)—C(=O)—O—$R^9$, a group —NH—($CHR^{10}$)—C(=O)—O—$R^9$ or a group —NH—C($CH_3$)$_2$—C(=O)—O—$R^9$; or $R^5$ represents hydroxy and $R^8$ represents a group —O—($CH_2$)—O—C(=O)—$R^9$; or $R^5$ represents unsubstituted phenyloxy and $R^8$ represents a group —NH—CH($CH_3$)—C(=O)—O—$R^9$; or P(O)$R^5R^8$ represents a group selected from the following structures

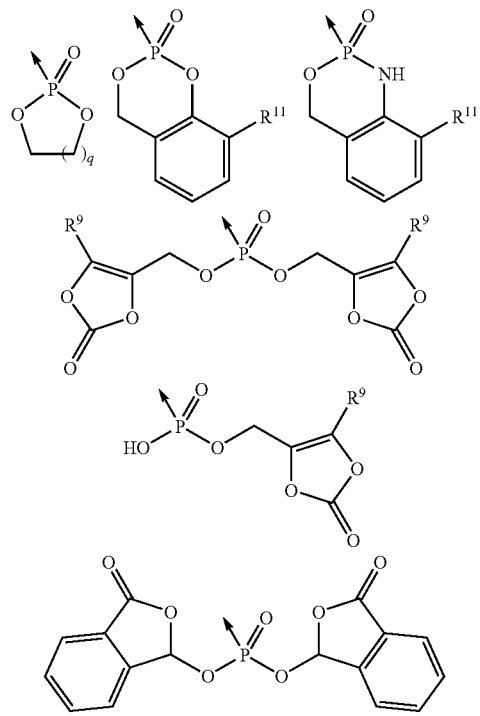

wherein the arrow marks the point of attachment to the remaining part of compounds of formula $I_{CE}$;

q represents 2;

$R^6$ represents hydrogen or ($C_1$-$C_3$)alkyl (preferably hydrogen or methyl);

$R^7$ represents ($C_1$-$C_4$)alkyl or unsubstituted ($C_3$-$C_6$)cycloalkyl;

$R^9$ represents ($C_1$-$C_4$)alkyl;

$R^{10}$ represents hydrogen, ($C_1$-$C_4$)alkyl, unsubstituted phenyl or unsubstituted benzyl;

$R^{11}$ represents hydrogen, ($C_1$-$C_4$)alkyl or ($C_1$-$C_4$)alkoxy;

and to the salts (in particular pharmaceutically acceptable salts) of such compounds.

3) According to one preferred embodiment, the invention relates to compounds of formula I that are also compounds of formula $I_P$

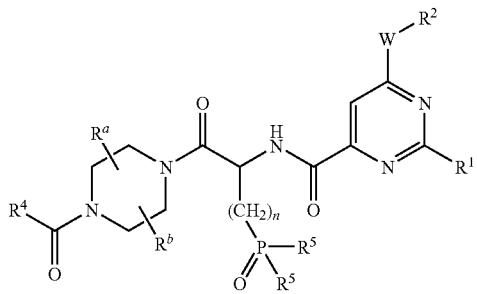

formula $I_P$ wherein $R^1$ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;

W represents a bond, and $R^2$ represents alkyl, hydroxyalkyl, alkoxyalkyl, cycloalkyl, aryl or heteroaryl; or W represents —O— and $R^2$ represents alkyl or heterocyclyl; or W represents —$NR^3$—, $R^2$ represents alkyl, alkoxycarbonylalkyl, carboxyalkyl, hydroxyalkyl, alkoxyalkyl, heterocyclyl, cycloalkyl, aryl or aralkyl and $R^3$ represents hydrogen or alkyl; or W represents —$NR^3$— and $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^y$—, it being understood however that said heterocyclic ring does not contain more than one member selected from the group consisting of —$CHR^x$—, —O—, —S—, —CO— and —$NR^y$—, $R^x$ representing hydroxy, hydroxymethyl, alkoxymethyl or alkoxy and $R^y$ representing hydrogen or alkyl;

or also W represents —$NR^3$— and $R^2$ and $R^3$ form, together with the nitrogen that carries them, an imidazolyl, pyrazolyl, 1,2,3-triazolyl or 1,2,4-triazolyl ring, which ring may be substituted by an alkyl group (especially by a methyl group);

$R^a$ represents hydrogen or methyl;

$R^b$ represents hydrogen or methyl;

$R^4$ represents alkoxy;

n represents 0, 1 or 2;

$R^5$ represents hydroxy or a group —O—($CHR^6$)—O—C(=O)—$R^7$ wherein $R^6$ represents hydrogen or ($C_1$-$C_3$) alkyl and $R^7$ represents ($C_1$-$C_4$)alkyl;

and to the salts (in particular pharmaceutically acceptable salts) of such compounds.

4) In particular, the invention relates to compounds of formula $I_P$ that are also compounds of formula $I_{CEP}$

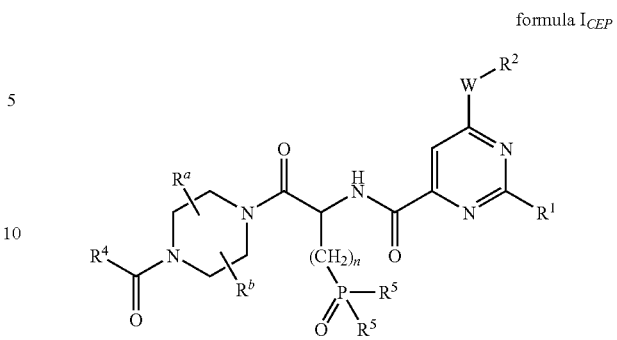

formula $I_{CEP}$ wherein $R^1$ represents phenyl optionally substituted once or twice by substituents independently selected from the group consisting of halogen, methyl, methoxy, trifluoromethyl and trifluoromethoxy (and preferably optionally substituted once or twice by substituents independently selected from the group consisting of halogen, methyl and trifluoromethyl, especially optionally substituted once by halogen, methyl or trifluoromethyl);

W represents a bond, and $R^2$ represents alkyl, hydroxyalkyl, alkoxyalkyl, cycloalkyl, a phenyl group optionally substituted once by alkoxy, or also an unsubstituted monocyclic heteroaryl group; or W represents —O— and $R^2$ represents alkyl (notably methyl) or heterocyclyl (notably tetrahydrofuran-3-yl); or W represents —$NR^3$—, $R^2$ represents alkyl, alkoxycarbonylalkyl, carboxyalkyl, hydroxyalkyl, alkoxyalkyl, heterocyclyl, phenyl or phenylalkyl, or a cycloalkyl group of 3 to 7 carbon atoms (preferably of 3 to 6 and more preferably of 3 to 5 carbon atoms) which may be substituted once by hydroxymethyl or alkoxymethyl (preferably methoxymethyl or ethoxymethyl and more preferably methoxymethyl), and $R^3$ represents hydrogen or alkyl (and notably hydrogen or methyl); or W represents —$NR^3$— and $R^2$ and $R^3$ form, together with the nitrogen that carries them, a heterocyclic ring of 4 to 7 members (and notably of 5 to 6 members) wherein the members needed to complete said heterocyclic ring are each independently selected from —$CH_2$—, —$CHR^x$—, —O— and —$NR^y$—, it being understood however that said heterocyclic ring does not contain more than one member selected from the group consisting of —$CHR^x$—, —O— and —$NR^y$—, $R^x$ representing hydroxy, hydroxymethyl or alkoxy (notably methoxy) and $R^y$ representing alkyl (especially methyl);

or also W represents —$NR^3$— and $R^2$ and $R^3$ form, together with the nitrogen that carries them, a pyrazolyl ring which may be substituted by an alkyl group (especially by a methyl group);

$R^a$ represents hydrogen or methyl;

$R^b$ represents hydrogen;

$R^4$ represents alkoxy;

n represents 0, 1 or 2;

$R^5$ represents hydroxy or a group —O—($CHR^6$)—O—C(=O)—$R^7$ wherein $R^6$ represents hydrogen or ($C_1$-$C_3$) alkyl and $R^7$ represents ($C_1$-$C_4$)alkyl;

and to salts (in particular pharmaceutically acceptable salts) of compounds of formula $I_{CE}$.

5) Preferably, the compounds of formula I as defined in embodiment 1) or 2) above or their salts (among which the pharmaceutically acceptable salts will be preferred) will be such that they are also compounds of formula $I_{ST1}$ and have the stereochemistry drawn below formula $I_{ST1}$

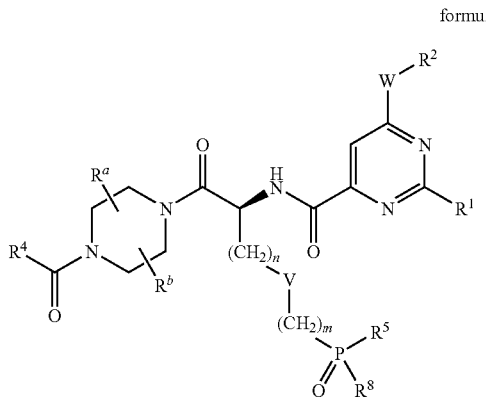

6) According to another preferred embodiment of this invention, the compounds of formula I as defined in embodiment 1) or 2) or their salts (among which the pharmaceutically acceptable salts will be preferred) will be such that they are also compounds of formula $I_{ST2}$, wherein n represents 1 or 3, and have the stereochemistry drawn below formula $I_{ST2}$

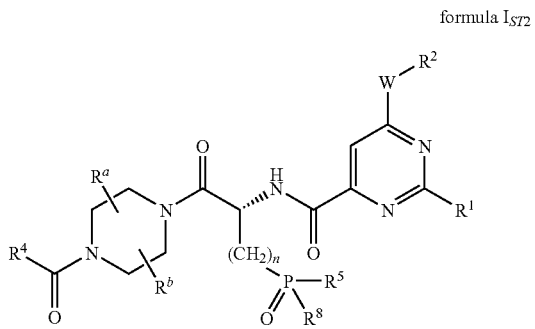

7) According to one preferred embodiment of this invention, the compounds of formula I as defined in embodiment 1), 2) or 5) or their salts (among which the pharmaceutically acceptable salts will be preferred) will be such that V represents a bond.
8) According to another preferred embodiment of this invention, the compounds of formula I as defined in embodiment 1), 2) or 5) or their salts (among which the pharmaceutically acceptable salts will be preferred) will be such that V represents phenyl.
9) According to a preferred embodiment of this invention, the compounds of formula I as defined in embodiment 1), 2), 5) or 7) or their salts (among which the pharmaceutically acceptable salts will be preferred) will be such that when V represents a bond, then m represents 0 and n represents 1, 2 or 3.
10) According to a preferred embodiment of this invention, the compounds of formula I as defined in embodiment 1), 2), 5) or 8) or their salts (among which the pharmaceutically acceptable salts will be preferred) will be such that when V represents phenyl, then m represents 0 and n represents 0 or 1.
11) According to a preferred embodiment of this invention, the compounds of formula I as defined in embodiment 1), 2), 5) or 8) or their salts (among which the pharmaceuti-cally acceptable salts will be preferred) will be such that when V represents phenyl, then m represents 1 and n represents 1.
12) According to a preferred embodiment of this invention, the compounds of formula I as defined in any one of embodiments 1), 2), 5), 7) or 9) or their salts (among which the pharmaceutically acceptable salts will be preferred) will be such that when n represents 2, V represents a bond and m represents 0, then $R^4$ represents $(C_4-C_6)$alkoxy, especially linear $(C_4-C_6)$alkoxy and in particular n-butoxy.
13) According to one preferred embodiment of this invention, the compounds of formula $I_P$ as defined in embodiment 3) or 4) above or their salts (among which the pharmaceutically acceptable salts will be preferred) will be such that when n represents 2, then $R^4$ represents $(C_4-C_6)$alkoxy, especially linear $(C_4-C_6)$alkoxy and in particular n-butoxy.
14) According to one particular embodiment of this invention, the compounds of formula I as defined in any one of embodiments 1) to 5), 7), 8) or 10) or their salts (among which the pharmaceutically acceptable salts will be preferred) will be such that n represents 0.
15) According to another particular embodiment of this invention, the compounds of formula I as defined in any one of embodiments 1) to 11) or their salts (among which the pharmaceutically acceptable salts will be preferred) will be such that n represents 1.
16) According to yet another particular embodiment of this invention, the compounds of formula I as defined in any one of embodiments 1) to 5), 7), 9) or 12) to 13) or their salts (among which the pharmaceutically acceptable salts will be preferred) will be such that n represents 2.
17) According to yet another particular embodiment of this invention, the compounds of formula $I_P$ as defined in embodiment 3) or 4) above or their salts (among which the pharmaceutically acceptable salts will be preferred) will be such that n represents 2.
18) According to yet another particular embodiment of this invention, the compounds of formula I as defined in embodiment 1), 2), 5), 6), 7) or 9) or their salts (among which the pharmaceutically acceptable salts will be preferred) will be such that n represents 3.
19) Preferably, the compounds of formula I as defined in any one of embodiments 1) to 18) above or their salts (among which the pharmaceutically acceptable salts will be preferred) will be such that $R^4$ represents $(C_4-C_6)$alkoxy, especially linear $(C_4-C_6)$alkoxy and in particular n-butoxy.
20) Preferably, the compounds of formula $I_P$ as defined in embodiment 17) above or their salts (among which the pharmaceutically acceptable salts will be preferred) will be such that $R^4$ represents $(C_4-C_6)$alkoxy, especially linear $(C_4-C_6)$alkoxy and in particular n-butoxy.
21) Preferably, the compounds of formula $I_P$ as defined in embodiment 17) or 20) above or their salts (among which the pharmaceutically acceptable salts will be preferred) will be such that they have the stereochemistry drawn below

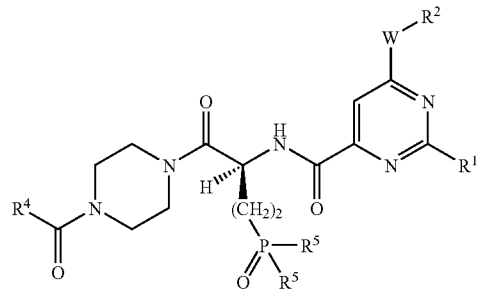

22) Preferably, the compounds of formula I as defined in one of embodiments 1) to 21) above or their salts (among which the pharmaceutically acceptable salts will be preferred) will be such that $R^1$ represents phenyl optionally substituted once by halogen, methyl, methoxy, trifluoromethyl or trifluoromethoxy (notably phenyl optionally substituted once by halogen, methyl or trifluoromethyl and especially phenyl optionally substituted once by fluorine, methyl or trifluoromethyl).

23) More preferably, the compounds of formula I as defined in one of embodiments 1) to 22) above or their salts (among which the pharmaceutically acceptable salts will be preferred) will be such that $R^1$ represents unsubstituted phenyl.

24) According to one variant of this invention, the compounds of formula I as defined in one of embodiments 1) to 23) above or their salts (among which the pharmaceutically acceptable salts will be preferred) will be such that W represents a bond.

25) Preferably, the compounds of formula I as defined in embodiment 24) above or their salts (among which the pharmaceutically acceptable salts will be preferred) will be such that $R^2$ represents alkyl (notably methyl and isopropyl and especially methyl), hydroxyalkyl (especially 3-hydroxy-butyl), alkoxyalkyl (especially 3-methoxy-propyl), cycloalkyl (especially cyclopropyl optionally substituted once by hydroxymethyl or alkoxymethyl), a phenyl group optionally substituted once by alkoxy, or also an unsubstituted monocyclic heteroaryl group (especially thiophen-3-yl).

26) More preferably, the compounds of formula I as defined in embodiment 25) above or their salts (among which the pharmaceutically acceptable salts will be preferred) will be such that $R^2$ represents hydroxyalkyl, alkoxyalkyl or cycloalkyl (especially cyclopropyl optionally substituted once by alkoxymethyl or alkoxy and more especially cyclopropyl optionally substituted once by alkoxymethyl).

27) According to another variant of this invention, the compounds of formula I as defined in one of embodiments 1), 2), 5) to 12), 14) to 16), 18) to 20), 22) or 23) above or their salts (among which the pharmaceutically acceptable salts will be preferred) will be such that W represents —O— and $R^2$ represents alkyl (notably methyl), cycloalkyl (notably cyclopentyl), hydroxyalkyl (notably 2-hydroxyethyl) or heterocyclyl (notably tetrahydrofuran-3-yl).

28) According to another variant of this invention, the compounds of formula I as defined in one of embodiments 1) to 23) above or their salts (among which the pharmaceutically acceptable salts will be preferred) will be such that W represents —O—.

29) Preferably, the compounds of formula I as defined in embodiment 28) above or their salts (among which the pharmaceutically acceptable salts will be preferred) will be such that $R^2$ represents methyl or heterocyclyl (e.g. tetrahydrofuran-3-yl), and notably heterocyclyl (especially tetrahydrofuran-3-yl).

30) According to a further variant of this invention, the compounds of formula I as defined in one of embodiments 1), 3) or 5) to 23) above or their salts (among which the pharmaceutically acceptable salts will be preferred) will be such that W represents —$NR^3$—, $R^2$ represents alkyl, alkoxycarbonylalkyl, carboxyalkyl, hydroxyalkyl, alkoxyalkyl, heterocyclyl, cycloalkyl, aryl or aralkyl and $R^3$ represents hydrogen or alkyl, or such that W represents —$NR^3$— and $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^y$—, it being understood however that said heterocyclic ring does not contain more than one member selected from the group consisting of —$CHR^x$—, —O—, —S—, —CO— and —$NR^y$—, $R^x$ representing hydroxy, hydroxymethyl, alkoxymethyl or alkoxy and $R^y$ representing hydrogen or alkyl or also such that W represents —$NR^3$— and $R^2$ and $R^3$ form, together with the nitrogen that carries them, either an imidazolyl, pyrazolyl, 1,2,3-triazolyl or 1,2,4-triazolyl ring, which ring may be substituted by an alkyl group (especially by a methyl group).

31) According to a further variant of this invention, the compounds of formula I as defined in one of embodiments 1) to 3) or 5) to 23) above or their salts (among which the pharmaceutically acceptable salts will be preferred) will be such that W represents —$NR^3$—, $R^2$ represents alkyl, alkoxycarbonylalkyl, carboxyalkyl, hydroxyalkyl, alkoxyalkyl, heterocyclyl, cycloalkyl, phenyl or phenylalkyl and $R^3$ represents hydrogen or alkyl; or such that W represents —$NR^3$— and $R^2$ and $R^3$ form, together with the nitrogen that carries them, a heterocyclic ring of 4 to 7 members (preferably 4 to 6 members) wherein the members needed to complete said heterocyclic ring are each independently selected from —$CH_2$—, —$CHR^x$—, —O— and —$NR^y$—, it being understood however that said heterocyclic ring does not contain more than one member selected from the group consisting of —$CHR^x$—, —O— and —$NR^y$—, $R^x$ representing hydroxy, hydroxymethyl, alkoxymethyl or alkoxy (notably methoxy) and $R^y$ representing alkyl (especially methyl) or also such that W represents —$NR^3$— and $R^2$ and $R^3$ form, together with the nitrogen that carries them, a pyrazolyl ring which may be unsubstituted or monosubstituted by an alkyl group (especially by a methyl group);

32) According to one subvariant of said further variant, the compounds of formula I as defined in embodiment 30) above or their salts (among which the pharmaceutically acceptable salts will be preferred) will be such that W represents —$NR^3$—, $R^2$ represents alkyl, alkoxycarbonylalkyl, carboxyalkyl, hydroxyalkyl, alkoxyalkyl, heterocyclyl, cycloalkyl, aryl or aralkyl and $R^3$ represents hydrogen or alkyl (notably hydrogen or methyl).

33) Preferably, the compounds of formula I as defined in embodiment 31) or 32) above or their salts (among which the pharmaceutically acceptable salts will be preferred) will be such that W represents —$NR^3$—, $R^2$ represents alkyl, alkoxycarbonylalkyl, carboxyalkyl, hydroxyalkyl, alkoxyalkyl, heterocyclyl, cycloalkyl or phenylalkyl and $R^3$ represents hydrogen or alkyl (notably hydrogen or methyl).

34) More preferably, the compounds of formula I as defined in embodiment 31) or 32) above or their salts (among which the pharmaceutically acceptable salts will be preferred) will be such that W represents —$NR^3$—, $R^2$ represents ($C_1$-$C_4$)alkyl, ($C_1$-$C_2$)alkoxy-carbonyl-($C_1$-$C_4$)alkyl, carboxy-($C_1$-$C_4$)alkyl, ($C_1$-$C_4$)hydroxyalkyl, ($C_1$-$C_2$)alkoxy-($C_1$-$C_4$)alkyl, heterocyclyl, cycloalkyl or phenylalkyl (and in particular methyl, ethyl, iso-propyl, 2-ethoxycarbonyl-ethyl, 2-carboxy-ethyl, 2-hydroxyethyl, 2-methoxy-ethyl, tetrahydrofuran-3-yl, cyclopropyl or benzyl) and $R^3$ represents hydrogen or methyl (and notably hydrogen).

35) According to another subvariant of said further variant, the compounds of formula I as defined in embodiment 30) above or their salts (among which the pharmaceutically acceptable salts will be preferred) will be such that W represents —NR³— and R² and R³ form, together with the nitrogen that carries them, a heterocyclic ring of 4 to 7 members wherein the members needed to complete said heterocyclic ring are each independently selected from —CH₂—, —CHRˣ—, —O—, —S—, —CO— and —NRʸ—, it being understood however that said heterocyclic ring does not contain more than one member selected from the group consisting of —CHRˣ—, —O—, —S—, —CO— and —NRʸ—, Rˣ representing hydroxy, hydroxymethyl, alkoxymethyl or alkoxy and Rʸ representing hydrogen or alkyl (notably hydrogen or methyl).

36) Preferably, the compounds of formula I as defined in embodiment 31) or 35) above or their salts (among which the pharmaceutically acceptable salts will be preferred) will be such that W represents —NR³— and R² and R³ form, together with the nitrogen that carries them, a heterocyclic ring of 4 to 7 members (and notably of 4 to 6 members and especially of 5 to 6 members) wherein the members needed to complete said heterocyclic ring are each independently selected from —CH₂—, —CHRˣ—, —O— and —NRʸ—, it being understood however that said heterocyclic ring does not contain more than one member selected from the group consisting of —CHRˣ—, —O— and —NRʸ—, Rˣ representing hydroxy, hydroxymethyl, alkoxymethyl or alkoxy (and notably hydroxy, hydroxymethyl or alkoxy) and Rʸ representing alkyl (especially methyl).

37) More preferably, the compounds of formula I as defined in embodiment 31) or 35) above or their salts (among which the pharmaceutically acceptable salts will be preferred) will be such that W represents —NR³— and R² and R³ form, together with the nitrogen that carries them, a heterocyclic ring of 4 to 6 members (and especially of 5 to 6 members) wherein the members needed to complete said heterocyclic ring are each independently selected from —CH₂—, —CHRˣ—, —O— and —NRʸ—, it being understood however that said heterocyclic ring does not contain more than one member selected from the group consisting of —CHRˣ—, —O— and —NRʸ—, Rˣ representing hydroxy, hydroxymethyl, methoxymethyl or methoxy (especially hydroxy, hydroxymethyl or methoxy) and Rʸ representing methyl (and especially such that R² and R³ form, together with the nitrogen that carries them, 3-methoxymethyl-azetidin-1-yl, pyrrolidin-1-yl, morpholin-4-yl, 4-methyl-piperazin-1-yl, 3-methoxy-pyrrolidin-1-yl, 3-hydroxy-pyrrolidin-1-yl or 2-hydroxymethyl-piperidin-1-yl and in particular such that R² and R³ form, together with the nitrogen that carries them, pyrrolidin-1-yl, morpholin-4-yl, 4-methyl-piperazin-1-yl, 3-methoxy-pyrrolidin-1-yl, 3-hydroxy-pyrrolidin-1-yl or 2-hydroxymethyl-piperidin-1-yl).

38) According to yet another subvariant of said further variant, the compounds of formula I as defined in embodiment 30) above or their salts (among which the pharmaceutically acceptable salts will be preferred) will be such that W represents —NR³— and R² and R³ form, together with the nitrogen that carries them, an imidazolyl, pyrazolyl, 1,2,3-triazolyl or 1,2,4-triazolyl ring, which ring may be substituted by an alkyl group (especially by a methyl group).

39) Preferably, the compounds of formula I as defined in embodiment 31) or 38) above or their salts (among which the pharmaceutically acceptable salts will be preferred) will be such that R² and R³ form, together with the nitrogen that carries them, a pyrazolyl ring which may be substituted by a methyl group (and in particular such that R² and R³ form, together with the nitrogen that carries them, pyrazol-1-yl or 4-methyl-pyrazol-1-yl).

40) Besides, the compounds of formula I as defined in one of embodiments 1) to 11), 14) to 18) or 21) to 39) above (among which the pharmaceutically acceptable salts will be preferred) will preferably be such that R⁴ represents (C₂-C₄)alkoxy, especially linear (C₂-C₄)alkoxy, in particular ethoxy or n-butoxy.

41) According to a preferred variant of embodiment 40), the compounds of formula I (among which the pharmaceutically acceptable salts will be preferred) will be such that R⁴ represents ethoxy.

42) According to another preferred variant of embodiment 40), the compounds of formula I as defined in one of embodiments 1) to 39) above (among which the pharmaceutically acceptable salts will be preferred) will be such that R⁴ represents n-butoxy.

43) One main embodiment of this invention relates to the compounds of formula I$_P$ as defined in embodiment 3) that are also compounds of formula I$_{PD}$

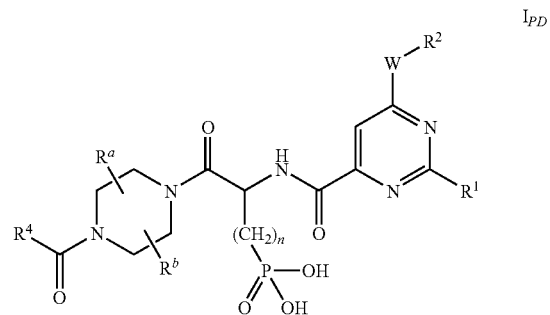

wherein
R¹ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;
W represents a bond, and R² represents alkyl, hydroxyalkyl, alkoxyalkyl, cycloalkyl, aryl or heteroaryl; or
W represents —O— and R² represents alkyl or heterocyclyl; or
W represents —NR³—, R² represents alkyl, alkoxycarbonylalkyl, carboxyalkyl, hydroxyalkyl, alkoxyalkyl, heterocyclyl, cycloalkyl, aryl or aralkyl and R³ represents hydrogen or alkyl; or
W represents —NR³— and R² and R³ form, together with the nitrogen that carries them, a heterocyclic ring of 4 to 7 members wherein the members needed to complete said heterocyclic ring are each independently selected from —CH₂—, —CHRˣ—, —O—, —S—, —CO— and —NRʸ—, it being understood however that said heterocyclic ring does not contain more than one member selected from the group consisting of —CHRˣ—, —O—, —S—, —CO— and —NRʸ—, Rˣ representing hydroxy, hydroxymethyl, alkoxymethyl or alkoxy and Rʸ representing hydrogen or alkyl;
or also W represents —NR³— and R² and R³ form, together with the nitrogen that carries them, an imidazolyl, pyrazolyl, 1,2,3-triazolyl or 1,2,4-triazolyl ring, which ring may be substituted by an alkyl group (especially by a methyl group);
Rᵃ represents hydrogen or methyl;
Rᵇ represents hydrogen or methyl;

$R^4$ represents alkoxy;

n represents 0, 1 or 2;

and to the salts (in particular pharmaceutically acceptable salts) of such compounds.

44) Another main embodiment of this invention relates to the compounds of formula $I_P$ as defined in embodiment 3) that are also compounds of formula $I_{P\text{-}PDG}$

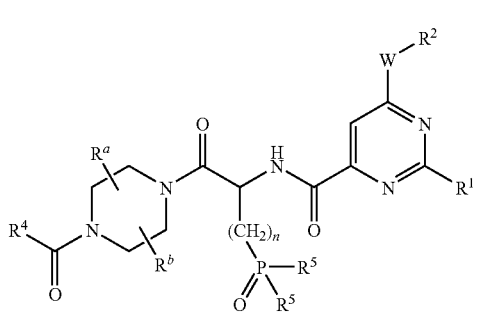

wherein $R^1$ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;

W represents a bond, and $R^2$ represents alkyl, hydroxyalkyl, alkoxyalkyl, cycloalkyl, aryl or heteroaryl; or W represents —O— and $R^2$ represents alkyl or heterocyclyl; or W represents —$NR^3$—, $R^2$ represents alkyl, alkoxycarbonylalkyl, carboxyalkyl, hydroxyalkyl, alkoxyalkyl, heterocyclyl, cycloalkyl, aryl or aralkyl and $R^3$ represents hydrogen or alkyl; or W represents —$NR^3$— and $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^y$—, it being understood however that said heterocyclic ring does not contain more than one member selected from the group consisting of —$CHR^x$—, —O—, —S—, —CO— and —$NR^y$—, $R^x$ representing hydroxy, hydroxymethyl, alkoxymethyl or alkoxy and $R^y$ representing hydrogen or alkyl;

or also W represents —$NR^3$— and $R^2$ and $R^3$ form, together with the nitrogen that carries them, an imidazolyl, pyrazolyl, 1,2,3-triazolyl or 1,2,4-triazolyl ring, which ring may be substituted by an alkyl group (especially by a methyl group);

$R^a$ represents hydrogen or methyl;

$R^b$ represents hydrogen or methyl;

$R^4$ represents alkoxy;

n represents 0, 1 or 2;

$R^5$ represents a group —O—($CHR^6$)—O—C(=O)—$R^7$ wherein $R^6$ represents hydrogen or ($C_1$-$C_3$)alkyl and $R^7$ represents ($C_1$-$C_4$)alkyl;

and to the salts (in particular pharmaceutically acceptable salts) of such compounds.

45) Preferably, the compounds of formula $I_P$ as defined in embodiment 44) above or their salts (among which the pharmaceutically acceptable salts will be preferred) will be such that $R^6$ represents hydrogen (and notably such that $R^5$ represents 2,2-dimethyl-propionyloxymethoxy or isobutyryloxymethoxy).

46) According to a preferred embodiment, the compounds of formula I as defined in any one of embodiments 1) to 43) above or their salts (among which the pharmaceutically acceptable salts will be preferred) will be such that $R^5$ and, if present, $R^8$ are identical and represent hydroxy.

47) According to another preferred embodiment, the compounds of formula I as defined in any one of embodiments 1), 2), 5) to 12), 14) to 16), 18), 19) or 22) to 42) above or their salts (among which the pharmaceutically acceptable salts will be preferred) will be such that $R^5$ and, if present, $R^8$ are identical and represent each unsubstituted phenyloxy, unsubstituted benzyloxy, a group —O—($CHR^6$)—O—C(=O)—$R^7$, a group —O—($CHR^6$)—O—C(=O)—O—$R^7$, a group —O—($CHR^6$)—C(=O)—O—$R^9$, a group —NH—($CHR^{10}$)—C(=O)—O—$R^9$ or a group —NH—C($CH_3$)$_2$—C(=O)—O—$R^9$.

48) According to a more preferred embodiment, the compounds of formula I as defined in embodiment 47) above or their salts (among which the pharmaceutically acceptable salts will be preferred) will be such that $R^5$ and, if present, $R^8$ are identical and represent —O—($CHR^6$)—O—C(=O)—$R^7$ (and most preferably —O—($CH_2$)—O—C(=O)—$R^7$).

49) According to another preferred embodiment, the compounds of formula I as defined in embodiment 47) above or their salts (among which the pharmaceutically acceptable salts will be preferred) will be such that $R^5$ and, if present, $R^8$ are identical and represent —O—($CHR^6$)—O—C(=O)—O—$R^7$ (and most preferably —O—($CH_2$)—O—C(=O)—O—$R^7$).

50) According to another preferred embodiment, the compounds of formula I as defined in embodiment 47) above or their salts (among which the pharmaceutically acceptable salts will be preferred) will be such that $R^5$ and, if present, $R^8$ are identical and represent —NH—($CHR^{10}$)—C(=O)—O—$R^9$ or —NH—C($CH_3$)$_2$—C(=O)—O—$R^9$.

51) According to still another preferred embodiment, the compounds of formula I as defined in any one of embodiments 1), 2), 5) to 12), 14) to 16), 18), 19) or 22) to 42) above or their salts (among which the pharmaceutically acceptable salts will be preferred) will be such that $R^5$ represents hydroxy and $R^8$ represents a group —O—($CH_2$)—O—C(=O)—$R^9$ (and notably —O—($CH_2$)—O—C(=O)—$CH_3$).

52) According to still another preferred embodiment, the compounds of formula I as defined in any one of embodiments 1), 2), 5) to 12), 14) to 16), 18), 19) or 22) to 42) above or their salts (among which the pharmaceutically acceptable salts will be preferred) will be such that $R^5$ represents unsubstituted phenyloxy and $R^8$ represents a group —NH—CH($CH_3$)—C(=O)—O—$R^9$ (and notably —NH—CH($CH_3$)—C(=O)—O—$CH_2CH_3$).

53) According to still another preferred embodiment, the compounds of formula I as defined in any one of embodiments 1), 2), 5) to 12), 14) to 16), 18), 19) or 22) to 42) above or their salts (among which the pharmaceutically acceptable salts will be preferred) will be such that P(O)$R^5R^8$ represents a group selected from the following structures

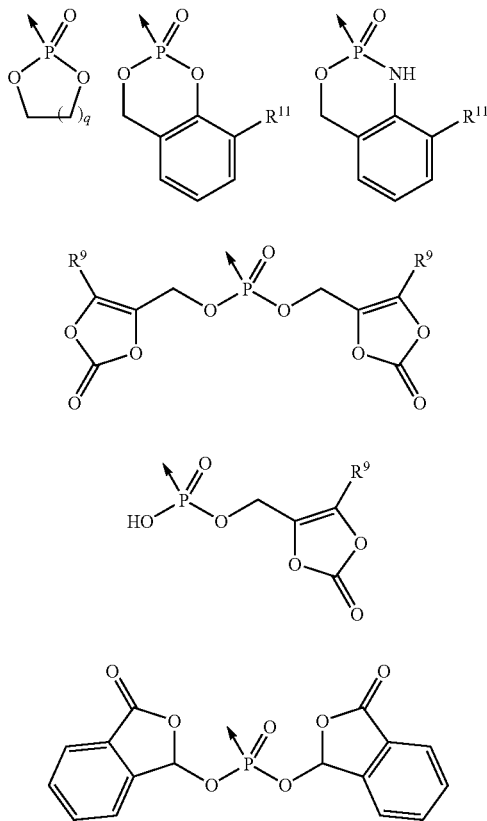

wherein the arrow marks the point of attachment to the remaining part of compounds of formula I, q represents 1 or 2 (and preferably 2), $R^9$ represents $(C_1$-$C_4)$alkyl (and preferably methyl or tert-butyl) and $R^{11}$ represents hydrogen, $(C_1$-$C_4)$alkyl or $(C_1$-$C_4)$alkoxy.

54) Another preferred embodiment of this invention relates to the compounds of formula I as defined in embodiment 1), wherein $R^1$ represents phenyl;

W represents —$NR^3$— and $R^2$ and $R^3$ form, together with the nitrogen that carries them, a heterocyclic ring of 5 members wherein the members needed to complete said heterocyclic ring are each independently selected from —$CH_2$— and —$CHR^x$—, it being understood however that said heterocyclic ring does not contain more than one —$CHR^x$— group, $R^x$ representing alkoxy (and preferably W represents —$NR^3$— and $R^2$ and $R^3$ form, together with the nitrogen that carries them, a 3-methoxy-pyrrolidin-1-yl group);

$R^a$ represents hydrogen;

$R^b$ represents hydrogen;

$R^4$ represents alkoxy;

n represents 1 or 2, V represents a bond, and m represents 0;

$R^5$ and $R^8$ are identical and represent each a group —O—(CHR$^6$)—O—C(=O)—$R^7$, a group —O—(CHR$^6$)—O—C(=O)—O—$R^7$ or a group —NH—(CHR$^{10}$)—C(=O)—O—$R^9$; or P(O)$R^5R^8$ represents a group selected from the following structures wherein the arrow marks the point of attachment to the remaining part of compounds of formula I;

q represents 2;

$R^6$ represents hydrogen;

$R^7$ represents $(C_1$-$C_4)$alkyl;

$R^9$ represents $(C_1$-$C_4)$alkyl;

$R^{10}$ represents hydrogen, $(C_1$-$C_4)$alkyl or unsubstituted phenyl;

and to the salts (in particular pharmaceutically acceptable salts) of such compounds.

55) The following compounds of formula I as defined in embodiment 1) to 4) are particularly preferred:

4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid ethyl ester;

4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester;

4-((S)-2-{[6-((S)-3-methoxy-pyrrolidin-1-yl)-2-phenyl-pyrimidine-4-carbonyl]-amino}-3-phosphono-propionyl)-piperazine-1-carboxylic acid ethyl ester;

4-((S)-2-{[6-((S)-3-methoxy-pyrrolidin-1-yl)-2-phenyl-pyrimidine-4-carbonyl]-amino}-4-phosphono-butyryl)-piperazine-1-carboxylic acid ethyl ester;

4-((S)-2-{[6-((S)-3-methoxy-pyrrolidin-1-yl)-2-phenyl-pyrimidine-4-carbonyl]-amino}-4-phosphono-butyryl)-piperazine-1-carboxylic acid butyl ester;

4-((S)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester;

4-{(S)-2-[(2-phenyl-6-pyrazol-1-yl-pyrimidine-4-carbonyl)-amino]-4-phosphono-butyryl}-piperazine-1-carboxylic acid butyl ester;

4-((S)-2-{[6-(4-methyl-pyrazol-1-yl)-2-phenyl-pyrimidine-4-carbonyl]-amino}-4-phosphono-butyryl)-piperazine-1-carboxylic acid butyl ester;

4-[(S)-2-({2-phenyl-6-[(S)-(tetrahydro-furan-3-yl)oxy]-pyrimidine-4-carbonyl}-amino)-4-phosphono-butyryl]-piperazine-1-carboxylic acid butyl ester;

4-{(S)-2-[(2-phenyl-6-pyrrolidin-1-yl-pyrimidine-4-carbonyl)-amino]-4-phosphono-butyryl}-piperazine-1-carboxylic acid butyl ester;

4-{(S)-2-[(6-isopropylamino-2-phenyl-pyrimidine-4-carbonyl)-amino]-4-phosphono-butyryl}-piperazine-1-carboxylic acid butyl ester;

4-{(S)-2-[(6-morpholin-4-yl-2-phenyl-pyrimidine-4-carbonyl)-amino]-4-phosphono-butyryl}-piperazine-1-carboxylic acid butyl ester;

4-((S)-2-{[6-(4-methyl-piperazin-1-yl)-2-phenyl-pyrimidine-4-carbonyl]-amino}-4-phosphono-butyryl)-piperazine-1-carboxylic acid butyl ester;

4-{(R)-2-[(6-methylamino-2-phenyl-pyrimidine-4-carbonyl)-amino]-3-phosphono-propionyl}-piperazine-1-carboxylic acid butyl ester;

4-{(R)-2-[(6-dimethylamino-2-phenyl-pyrimidine-4-carbonyl)-amino]-3-phosphono-propionyl}-piperazine-1-carboxylic acid butyl ester;

4-{(R)-2-[(6-ethylamino-2-phenyl-pyrimidine-4-carbonyl)-amino]-3-phosphono-propionyl}-piperazine-1-carboxylic acid butyl ester;

4-{(R)-2-[(6-isopropylamino-2-phenyl-pyrimidine-4-carbonyl)-amino]-3-phosphono-propionyl}-piperazine-1-carboxylic acid butyl ester;

4-((S)-2-{[2-(4-fluoro-phenyl)-6-((S)-3-methoxy-pyrrolidin-1-yl)-pyrimidine-4-carbonyl]-amino}-4-phosphono-butyryl)-piperazine-1-carboxylic acid butyl ester;

4-((S)-2-{[6-((S)-3-methoxy-pyrrolidin-1-yl)-2-p-tolyl-pyrimidine-4-carbonyl]-amino}-4-phosphono-butyryl)-piperazine-1-carboxylic acid butyl ester;

4-((S)-2-{[2-(2-fluoro-phenyl)-6-((S)-3-methoxy-pyrrolidin-1-yl)-pyrimidine-4-carbonyl]-amino}-4-phosphono-butyryl)-piperazine-1-carboxylic acid butyl ester;

4-((S)-2-{[2-(3-fluoro-phenyl)-6-((S)-3-methoxy-pyrrolidin-1-yl)-pyrimidine-4-carbonyl]-amino}-4-phosphono-butyryl)-piperazine-1-carboxylic acid butyl ester;

4-{(R)-2-[(6-methoxy-2-phenyl-pyrimidine-4-carbonyl)-amino]-3-phosphono-propionyl}-piperazine-1-carboxylic acid butyl ester;

4-{(R)-2-[(6-methyl-2-phenyl-pyrimidine-4-carbonyl)-amino]-3-phosphono-propionyl}-piperazine-1-carboxylic acid butyl ester;

4-{(R)-2-[(6-cyclopropylamino-2-phenyl-pyrimidine-4-carbonyl)-amino]-3-phosphono-propionyl}-piperazine-1-carboxylic acid butyl ester;

4-{(R)-2-[(2-phenyl-6-phenylamino-pyrimidine-4-carbonyl)-amino]-3-phosphono-propionyl}-piperazine-1-carboxylic acid butyl ester;

4-{(R)-2-[(6-benzylamino-2-phenyl-pyrimidine-4-carbonyl)-amino]-3-phosphono-propionyl}-piperazine-1-carboxylic acid butyl ester;

4-[(R)-2-({2-phenyl-6-[(R)-(tetrahydro-furan-3-yl)amino]-pyrimidine-4-carbonyl}-amino)-3-phosphono-propionyl]-piperazine-1-carboxylic acid butyl ester;

4-((R)-2-{[6-(3-hydroxy-pyrrolidin-1-yl)-2-phenyl-pyrimidine-4-carbonyl]-amino}-3-phosphono-propionyl)-piperazine-1-carboxylic acid butyl ester;

4-[(R)-2-({6-[(2-methoxy-ethyl)-methyl-amino]-2-phenyl-pyrimidine-4-carbonyl}-amino)-3-phosphono-propionyl]-piperazine-1-carboxylic acid butyl ester;

4-((R)-2-{[6-(2-ethoxycarbonyl-ethylamino)-2-phenyl-pyrimidine-4-carbonyl]-amino}-3-phosphono-propionyl)-piperazine-1-carboxylic acid butyl ester;

4-((R)-2-{[6-(2-carboxy-ethylamino)-2-phenyl-pyrimidine-4-carbonyl]-amino}-3-phosphono-propionyl)-piperazine-1-carboxylic acid butyl ester;

4-{(R)-2-[(2,6-diphenyl-pyrimidine-4-carbonyl)-amino]-3-phosphono-propionyl}-piperazine-1-carboxylic acid butyl ester;

4-{(R)-2-[(2-phenyl-6-thiophen-3-yl-pyrimidine-4-carbonyl)-amino]-3-phosphono-propionyl}-piperazine-1-carboxylic acid butyl ester;

4-((R)-2-{[6-(4-methoxy-phenyl)-2-phenyl-pyrimidine-4-carbonyl]-amino}-3-phosphono-propionyl)-piperazine-1-carboxylic acid butyl ester;

4-{(R)-2-[(6-cyclopropyl-2-phenyl-pyrimidine-4-carbonyl)-amino]-3-phosphono-propionyl}-piperazine-1-carboxylic acid butyl ester;

4-{(R)-2-[(6-butyl-2-phenyl-pyrimidine-4-carbonyl)-amino]-3-phosphono-propionyl}-piperazine-1-carboxylic acid butyl ester;

4-[(R)-2-({2-phenyl-6-[(S)-(tetrahydro-furan-3-yl)oxy]-pyrimidine-4-carbonyl}-amino)-3-phosphono-propionyl]-piperazine-1-carboxylic acid butyl ester;

4-((R)-2-{[6-((S)-3-methoxy-pyrrolidin-1-yl)-2-phenyl-pyrimidine-4-carbonyl]-amino}-3-phosphono-propionyl)-2-methyl-piperazine-1-carboxylic acid ethyl ester;

4-((R)-2-{[6-((S)-3-methoxy-pyrrolidin-1-yl)-2-phenyl-pyrimidine-4-carbonyl]-amino}-4-phosphono-butyryl)-piperazine-1-carboxylic acid ethyl ester;

4-((R)-2-{[6-((S)-3-methoxy-pyrrolidin-1-yl)-2-phenyl-pyrimidine-4-carbonyl]-amino}-4-phosphono-butyryl)-piperazine-1-carboxylic acid butyl ester;

4-((R)-2-{[6-((1S,2S)-2-methoxymethyl-cyclopropyl)-2-phenyl-pyrimidine-4-carbonyl]-amino}-3-phosphono-propionyl)-piperazine-1-carboxylic acid butyl ester;

4-((R)-2-{[6-((1S,2S)-2-hydroxymethyl-cyclopropyl)-2-phenyl-pyrimidine-4-carbonyl]-amino}-3-phosphono-propionyl)-piperazine-1-carboxylic acid butyl ester;

4-((R)-2-{[6-(2-hydroxy-ethylamino)-2-phenyl-pyrimidine-4-carbonyl]-amino}-3-phosphono-propionyl)-piperazine-1-carboxylic acid butyl ester;

4-((R)-2-{[6-(2-hydroxymethyl-piperidin-1-yl)-2-phenyl-pyrimidine-4-carbonyl]-amino}-3-phosphono-propionyl)-piperazine-1-carboxylic acid butyl ester;

4-((R)-2-{[6-(3-methoxy-propyl)-2-phenyl-pyrimidine-4-carbonyl]-amino}-3-phosphono-propionyl)-piperazine-1-carboxylic acid butyl ester;

4-((R)-2-{[6-(3-hydroxy-butyl)-2-phenyl-pyrimidine-4-carbonyl]-amino}-3-phosphono-propionyl)-piperazine-1-carboxylic acid butyl ester;

4-((S)-2-{[6-((S)-3-methoxy-pyrrolidin-1-yl)-2-(3-trifluoromethyl-phenyl)-pyrimidine-4-carbonyl]-amino}-4-phosphono-butyryl)-piperazine-1-carboxylic acid butyl ester;

4-((S)-4-[bis-(2,2-dimethyl-propionyloxymethoxy)-phosphoryl]-2-{[6-((S)-3-methoxy-pyrrolidin-1-yl)-2-phenyl-pyrimidine-4-carbonyl]-amino}-butyryl)-piperazine-1-carboxylic acid butyl ester;

4-((S)-4-(bis-isobutyryloxymethoxy-phosphoryl)-2-{[6-((S)-3-methoxy-pyrrolidin-1-yl)-2-phenyl-pyrimidine-4-carbonyl]-amino}-butyryl)-piperazine-1-carboxylic acid butyl ester;

4-((S)-4-{bis-[(2,2-dimethyl-propionyloxy)-ethoxy]-phosphoryl}-2-{[6-((S)-3-methoxy-pyrrolidin-1-yl)-2-phenyl-pyrimidine-4-carbonyl]-amino}-butyryl)-piperazine-1-carboxylic acid butyl ester;

4-((R)-3-[bis-(2,2-dimethyl-propionyloxymethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-{bis-[1-(2,2-dimethyl-propionyloxy)-ethoxy]-phosphoryl}-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[bis-(1-isobutyryloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[bis-(1-propionyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(bis-isobutyryloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-(2-{[6-((S)-3-methoxy-pyrrolidin-1-yl)-2-phenyl-pyrimidine-4-carbonyl]-amino}-2-phosphono-acetyl)-piperazine-1-carboxylic acid butyl ester;

wherein it is well understood that any stereogenic center of any above listed compound, which is not explicitly assigned, may be in absolute (R)- or (S)-configuration;

as well as the salts (in particular pharmaceutically acceptable salts) thereof.

56) Further preferred compounds of formula I as defined in embodiment 1) or 2) are selected from the group consisting of:

4-((R)-2-{[6-(2-Hydroxy-ethoxy)-2-phenyl-pyrimidine-4-carbonyl]-amino}-3-phosphono-propionyl)-piperazine-1-carboxylic acid butyl ester;

4-((S)-2-{[6-((S)-3-Methoxy-pyrrolidin-1-yl)-2-phenyl-pyrimidine-4-carbonyl]-amino}-5-phosphono-pentanoyl)-piperazine-1-carboxylic acid butyl ester;

4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid ethyl ester;

4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid butyl ester;

4-[(S)-2-{[6-((S)-3-Methoxy-pyrrolidin-1-yl)-2-phenyl-pyrimidine-4-carbonyl]-amino}-3-(4-phosphonomethyl-phenyl)-propionyl]-piperazine-1-carboxylic acid ethyl ester;

4-[(S)-2-{[6-((S)-3-Methoxy-pyrrolidin-1-yl)-2-phenyl-pyrimidine-4-carbonyl]-amino}-3-(4-phosphonomethyl-phenyl)-propionyl]-piperazine-1-carboxylic acid butyl ester;

4-((R)-2-{[6-((S)-3-Methoxy-pyrrolidin-1-yl)-2-phenyl-pyrimidine-4-carbonyl]-amino}-5-phosphono-pentanoyl)-piperazine-1-carboxylic acid butyl ester;

4-{(R)-2-[(6-Isopropyl-2-phenyl-pyrimidine-4-carbonyl)-amino]-3-phosphono-propionyl}-piperazine-1-carboxylic acid butyl ester;

4-((R)-2-{[6-(3-Methoxymethyl-azetidin-1-yl)-2-phenyl-pyrimidine-4-carbonyl]-amino}-3-phosphono-propionyl)-piperazine-1-carboxylic acid butyl ester;

4-{(R)-2-[(6-Cyclopentyloxy-2-phenyl-pyrimidine-4-carbonyl)-amino]-3-phosphono-propionyl}-piperazine-1-carboxylic acid ethyl ester;

4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid ethyl ester;

4-[2-{[6-((S)-3-Methoxy-pyrrolidin-1-yl)-2-phenyl-pyrimidine-4-carbonyl]-amino}-2-(4-phosphono-phenyl)-acetyl]-piperazine-1-carboxylic acid ethyl ester;

4-[2-{[6-((S)-3-Methoxy-pyrrolidin-1-yl)-2-phenyl-pyrimidine-4-carbonyl]-amino}-2-(4-phosphono-phenyl)-acetyl]-piperazine-1-carboxylic acid butyl ester;

4-[2-{[6-((S)-3-Methoxy-pyrrolidin-1-yl)-2-phenyl-pyrimidine-4-carbonyl]-amino}-2-(3-phosphono-phenyl)-acetyl]-piperazine-1-carboxylic acid ethyl ester;

4-[2-{[6-((S)-3-Methoxy-pyrrolidin-1-yl)-2-phenyl-pyrimidine-4-carbonyl]-amino}-2-(3-phosphono-phenyl)-acetyl]-piperazine-1-carboxylic acid butyl ester;

4-[2-{[6-((S)-3-Methoxy-pyrrolidin-1-yl)-2-phenyl-pyrimidine-4-carbonyl]-amino}-2-(2-phosphono-phenyl)-acetyl]-piperazine-1-carboxylic acid butyl ester;

4-((R)-2-{[6-(4-Methyl-piperazin-1-yl)-2-phenyl-pyrimidine-4-carbonyl]-amino}-3-phosphono-propionyl)-piperazine-1-carboxylic acid butyl ester;

4-{(R)-2-[(6-Morpholin-4-yl-2-phenyl-pyrimidine-4-carbonyl)-amino]-3-phosphono-propionyl}-piperazine-1-carboxylic acid butyl ester;

N,N'-Bis-(ethoxycarbonylmethyl)-3-{(S)-[6-((S)-3-methoxy-pyrrolidin-1-yl)-2-phenyl-pyrimidine-4-carbonyl]-amino}-4-oxo-4-(4-butoxy-carbonyl-piperazin-1-yl)-butyl-phosphonic acid diamide;

4-((R)-3-(Bis-acetoxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(Bis-propionyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(Bis-butyryloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

N,N'-Bis-(ethoxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-ethoxycarbonylethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-(methoxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-methoxycarbonyl-2-methyl-propyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-(tert-butyloxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-methoxycarbonylpropyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-methoxycarbonyl-2,2-dimethyl-propyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-tert-butyloxycarbonylethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-methoxycarbonyl-2-phenyl-ethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-methoxycarbonylphenylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-methoxycarbonylethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-(propyloxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-(isopropyloxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-(2-ethoxycarbonyl-prop-2-yl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

4-((R)-3-(Bis-methoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(Bis-ethoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-(R)-3-(Bis-isopropoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(Bis-tert-butoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[Bis-(1-ethyloxycarbonyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[Bis-(1-isopropyloxycarbonyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[Bis-(1-cyclohexyloxycarbonyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(Diphenoxy-phosphoryl)-2-{[6-((S)-3-methoxy-pyrrolidin-1-yl)-2phenyl-pyrimidine-4-carbonyl]-amino}-propionyl)-piperazine-1-carboxylic acid butyl ester;

4-((R)-3-[Bis-(5-methyl-2-oxo-[1,3]dioxol-4-ylmethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-[(R)-2-{[6-((S)-3-Methoxy-pyrrolidin-1-yl)-2-phenyl-pyrimidine-4-carbonyl]-amino}-3-(2-oxo-4H-2$\lambda^5$-benzo[1,3,2]dioxaphosphinin-2-yl)-propionyl]-piperazine-1-carboxylic acid butyl ester;

4-[(R)-2-{[6-((S)-3-Methoxy-pyrrolidin-1-yl)-2-phenyl-pyrimidine-4-carbonyl]-amino}-3-(2-oxo-1,4-dihydro-2H-2$\lambda^5$-benzo[d][1,3,2]oxazaphosphinin-2-yl)-propionyl]-piperazine-1-carboxylic acid butyl ester;

4-[(R)-2-{[6-((S)-3-Methoxy-pyrrolidin-1-yl)-2-phenyl-pyrimidine-4-carbonyl]-amino}-3-(8-methyl-2-oxo-1,4-dihydro-2H-2$\lambda^5$-benzo[d][1,3,2]oxazaphosphinin-2-yl)-propionyl]-piperazine-1-carboxylic acid butyl ester;

4-((R)-3-[Bis-(3-oxo-1,3-dihydro-isobenzofuran-1-yloxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(Bis-ethoxycarbonylmethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[Bis-((S)-1-ethoxycarbonyl-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

N-[(S)-1-Ethoxycarbonyl-ethyl]-O-phenyl-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid amide;

4-[(R)-2-{[6-((S)-3-Methoxy-pyrrolidin-1-yl)-2-phenyl-pyrimidine-4-carbonyl]-amino}-3-(2-oxo-2$\lambda^5$-[1,3,2]dioxaphosphinan-2-yl)-propionyl]-piperazine-1-carboxylic acid butyl ester;

4-[(R)-2-{[6-((S)-3-Methoxy-pyrrolidin-1-yl)-2-phenyl-pyrimidine-4-carbonyl]-amino}-3-(8-methyl-2-oxo-4H-2$\lambda^5$-benzo[1,3,2]dioxaphosphinin-2-yl)-propionyl]-piperazine-1-carboxylic acid butyl ester;

4-((R)-3-(8-Isopropyl-2-oxo-4H-2$\lambda^5$-benzo[1,3,2]dioxaphosphinin-2-yl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(8-Methoxy-2-oxo-1,4-dihydro-2H-2$\lambda^5$-benzo[d][1,3,2]oxazaphosphinin-2-yl)-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[(5-tert-Butyl-2-oxo-[1,3]dioxol-4-ylmethoxy)-hydroxy-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(Bis-benzyloxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(Acetoxymethoxy-hydroxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((S)-3-(Bis-acetoxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

4-((S)-3-(Bis-butyryloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

N,N'-Bis-((S)-1-ethoxycarbonylethyl)-2-{(S)-[6-((S)-3-methoxy-pyrrolidin-1-yl)-2-phenyl-pyrimidine-4-carbonyl]-amino}-3-oxo-3-(4-ethoxy-carbonyl-piperazin-1-yl)-propyl-phosphonic acid diamide;

4-((S)-3-(Bis-ethoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

4-((R)-3-(Bis-acetoxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

4-((R)-3-(Bis-butyryloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

N,N'-Bis-((S)-1-ethoxycarbonylethyl)-2-{(R)-[6-((S)-3-methoxy-pyrrolidin-1-yl)-2-phenyl-pyrimidine-4-carbonyl]-amino}-3-oxo-3-(4-ethoxy-carbonyl-piperazin-1-yl)-propyl-phosphonic acid diamide;

4-((R)-3-(Bis-ethoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

4-((S)-3-[4-(Bis-butyryloxymethoxy-phosphoryl)-phenyl]-2-{[6-((S)-3-methoxy-pyrrolidin-1-yl)-2-phenyl-pyrimidine-4-carbonyl]-amino}-propionyl)-piperazine-1-carboxylic acid ethyl ester;

N,N'-Bis-((S)-1-ethoxycarbonylethyl)-4-[2-{(S)-[6-((S)-3-methoxy-pyrrolidin-1-yl)-2-phenyl-pyrimidine-4-carbonyl]-amino}-3-oxo-3-(4-ethoxy-carbonyl-piperazin-1-yl)-propyl]-phenyl-phosphonic acid diamide; and 4-((S)-3-[4-(Bis-ethoxycarbonyloxymethoxy-phosphoryl)-phenyl]-2-{[6-((S)-3-methoxy-pyrrolidin-1-yl)-2-phenyl-pyrimidine-4-carbonyl]-amino}-propionyl)-piperazine-1-carboxylic acid ethyl ester;

wherein it is well understood that any stereogenic center of any above listed compound, which is not explicitly assigned, may be in absolute (R)- or (S)-configuration;

as well as the salts (in particular pharmaceutically acceptable salts) thereof.

57) A further object of the invention is the compounds of formula I (or of formula $I_{CE}$) as defined in one of embodiments 1) to 56) above, or their pharmaceutically acceptable salts, as medicaments.

The compounds of formula I and their pharmaceutically acceptable salts can be used as medicaments, e.g. in the form of pharmaceutical compositions for enteral or parental administration.

58) The invention thus also relates to pharmaceutical compositions containing at least one compound according to one of embodiments 1) to 56) above, or a pharmaceutically acceptable salt thereof, and a pharmaceutically acceptable carrier, diluent or excipient. In particular, the invention relates to pharmaceutical compositions containing at least one compound of formula I (or of formula $I_{CE}$) and one or more pharmaceutically acceptable carriers, diluents or excipients.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

59) The compounds according to formula I as defined in embodiments 1) to 56) above and the pharmaceutically acceptable salts thereof may be used for the preparation of a medicament, and are suitable:

for the treatment or prophylaxis of diseases including stable angina, unstable angina, myocardial infarction, embolism (including complications of atherosclerosis, notably embolic stroke), arterial thrombosis (including primary arterial thrombotic complications of atherosclerosis, notably thrombotic stroke), venous thrombosis (notably deep vein thrombosis), thrombosis secondary to vascular damage or to inflammation (including vasculitis, arteritis and glomerulonephritis), venoocclusive diseases, transient ischaemic attacks, peripheral vascular diseases, myocardial infarction with or without thrombolysis, myeloproliferative disease, thrombocythaemia, sickle cell disease, inflammatory bowel disease, thrombotic thrombocytopaenic purpura, haemolytic uraemic syndrome;

for preventing thrombotic complications of septicaemia, adult respiratory distress syndrome, anti-phospholipid syndrome, heparin-induced thrombocytopaenia and pre-eclampsia/eclampsia;

for preventing cardiovascular complications after certain surgery procedures (notably coronary revascularisation like angioplasty (PTCA), other vascular graft surgery, endarterectomy or stent placement) or after accidental trauma;

for preventing organ graft rejection.

60) Therefore, a particular object of this invention is the use of a compound of formula I (or of formula $I_{CE}$) as defined in one of embodiments 1) to 56) above, or of a pharmaceutically acceptable salt thereof, for the manufacture of a medicament for the uses listed in embodiment 59) above, and for the manufacture of a medicament for the treatment of occlusive vascular disorders in general.

61) More generally, the invention relates to the use of a compound of formula I (or of formula $I_{CE}$) as defined in one of embodiments 1) to 56) above, or of a pharmaceutically acceptable salt thereof, for the manufacture of a medicament for the treatment and/or prevention of occlusive vascular disorders as well as to the use of a compound of formula I (or of formula $I_{CE}$) for the manufacture of a medicament for the treatment and/or prevention of peripheral vascular, of visceral-, hepatic- and renal-vascular, of cardiovascular and of cerebrovascular diseases or conditions associated with platelet aggregation, including thrombosis in humans and other mammals.

62) Among the above-mentioned uses of compounds of formula I (or of formula $I_{CE}$) or of pharmaceutically acceptable salts thereof for the manufacture of medicaments according to embodiment 59) above, the uses for manufacturing medicaments for the treatment or prophylaxis of myocardial infarction, arterial thrombosis (notably thrombotic stroke), transient ischaemic attacks, peripheral vascular disease and stable and unstable angina will be preferred.

63) The invention further relates to the use of a compound of formula I (or of formula $I_{CE}$) according to one of embodiments 1) to 56) above, or of a pharmaceutically acceptable salt thereof, for the preservation of blood products in vitro (e.g. the preservation of platelet concentrates), or for the prevention of occlusion in extra-corporeal blood or blood product treatment machines (such as renal dialysis machines or plasmapheresis machines).

64) The invention also relates to methods of treatment for the disorders mentioned in embodiment 59) above, said methods comprising the administration to a patient in need thereof of an effective amount of a compound of formula I (or of formula $I_{CE}$) according to one of embodiments 1) to 56), or of a pharmaceutically acceptable salt of such a compound.

Any reference to a compound of formula I, $I_{CE}$, $I_P$, $I_{CEP}$, $I_{ST1}$, $I_{ST2}$, $I_{PD}$ or $I_{P-PDG}$ in this text is to be understood as referring also to the salts (and especially the pharmaceutically acceptable salts) of such compounds, as appropriate and expedient. The preferences indicated for the compounds of formula I of course apply mutatis mutandis to the compounds of formula $I_{CE}$, the compounds of formula $I_P$, the compounds of formula $I_{CEP}$, the compounds of formula $I_{ST1}$, the compounds of formula $I_{ST2}$, the compounds of formula $I_{PD}$ and the compounds of formula $I_{P-PDG}$, as well as to the salts and pharmaceutically acceptable salts of the compounds of formula I, of formula $I_{CE}$, of formula $I_P$, of formula $I_{CEP}$, of formula $I_{ST1}$, of formula $I_{ST2}$, of formula $I_{PD}$ or of formula $I_{P-PDG}$. The same applies to these compounds as medicaments, to pharmaceutical compositions containing these compounds as active principles or to the uses of these compounds for the manufacture of a medicament for the treatment of the diseases according to this invention.

Preparation of the Compounds of Formula I

Abbreviations:

The following abbreviations are used throughout the specification and the examples:

Ac acetyl
anh. anhydrous
aq. aqueous
Boc tert-butoxycarbonyl
br. broad
Cbz benzyloxycarbonyl
CC column chromatography
cHex cyclohexane
conc. concentrated
Cremophor-EL® compound with the Chemical Abstracts registry No. 61791-12-6
CV column volume
DCC 1,3-dicyclohexylcarbodiimide
DCM dichloromethane
DCMC N,N'-dicyclohexyl-4-morpholinecarboxamidine
DIPEA diisopropylethylamine
DME 1,2-dimethoxyethane
DMF N,N-dimethylformamide
DMPU N,N'-dimethylpropyleneurea
EA ethyl acetate
EDCI N-(3-dimethylaminopropyl)-N'-ethylcarbodiimide
Eq equivalent
Et ethyl
Fmoc 9H-fluoren-9-ylmethoxycarbonyl
HATU 2-(7-aza-1H-benzotriazole-1-yl)-1,1,3,3-tetramethyluronium hexafluorophosphate
Hept heptane
Hex hexane
HOBT 1-hydroxybenzotriazole
Hse L-homoserine
HV high vacuum
LC-MS Liquid Chromatography-Mass Spectrometry
MCPBA meta-chloroperbenzoic acid
Me methyl
n-BuLi n-butyl lithium
NMP N-methylpyrrolidone
org. organic
Pd/C palladium on carbon
PEG400 polyethylene glycol with a molecular weight of 400 g/mol
PG polypropylene glycol
Ph phenyl
PyBOP benzotriazole-1-yl-oxy-tris-pyrrolidino-phosphonium hexafluorophosphate
RT room temperature
sat. saturated
TEA triethylamine
TFA trifluoroacetic acid
THF tetrahydrofuran
TLC thin layer chromatography
$t_R$ retention time
Z benzyloxycarbonyl General Preparation Routes:

A further aspect of the invention is a process for the preparation of compounds of formula (I) (or formula $I_{CE}$). Compounds of formula (I) of the present invention can be prepared according to the general sequence of reactions outlined in the schemes below wherein V, W, $R^1$, $R^2$, $R^3$, $R^4$, $R^5$, $R^6$, $R^7$, $R^8$, $R^9$, $R^{10}$, n, m and q are as defined for formula (I). The compounds obtained may also be converted into pharmaceutically acceptable salts thereof in a manner known per se.

In general, all chemical transformations can be performed according to well-known standard methodologies as described in the literature or as described in the procedures below or in the experimental part.

The various compounds of formula I can be prepared using the general routes summarized in Scheme 1 hereafter.

Scheme 1

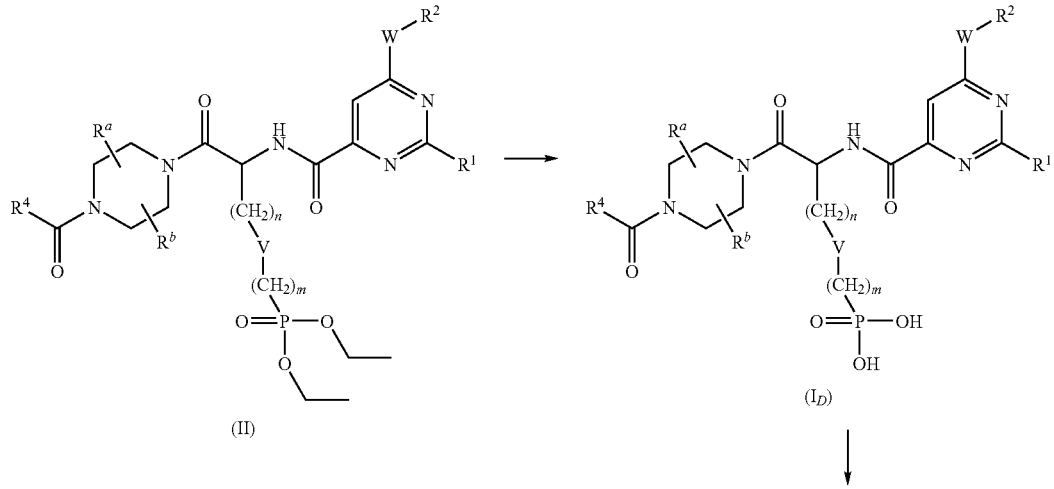

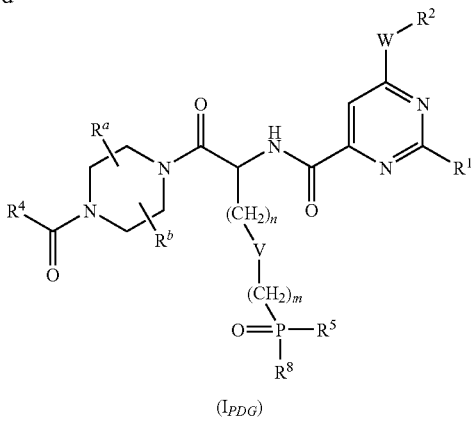

(I_PDG)

The compounds of formula $I_D$ can be prepared by treating the compounds of formula II with HCl optionally in the presence of water, in a suitable organic solvent such as THF, EA, dioxane or Et$_2$O and preferably at a temperature around RT, or with trimethylsilyl bromide or trimethylsilyl iodide in a suitable solvent such as DCM or MeCN and preferably at a temperature around RT.

The compounds of formula $I_{PDG}$ (R$^5$ and R$^8$≠OH) can be prepared by the reaction between a phosphonic acid of formula $I_D$ and an appropriate halide derivative of formula X—(CHR$^6$)—O—C(=O)—R$^7$, X—(CHR$^6$)—O—C(=O)—O—R$^7$, X—(CH$_2$)—C(=O)—O—R$^9$ or 3-bromophthalide, X being chloride, bromide or iodide, in the presence of a suitable base (e.g. NEt$_3$, DIPEA, DCMC) in a suitable solvent such as DMF, NMP or DMPU, optionally in the presence of NaI and preferably at a temperature between 45 and 90° C.

Alternatively, the compounds of formula $I_{PDG}$ (R$^5$ and/or R$^8$≠OH) can be prepared by the reaction between a phosphonic acid of formula $I_D$ and an appropriate α-amino acid alkyl ester of formula NH$_2$—(CHR$^{10}$)—C(=O)—O—R$^9$ or NH$_2$—C(CH$_3$)$_2$—C(=O)—O—R$^9$ in the presence of a suitable base (e.g. NEt$_3$) and an activating mixture of reagents such as a combination of 2,2'-dipyridyl disulfide and PPh$_3$ in a suitable solvent such as anhydrous pyridine and preferably at a temperature of about 60° C.

Alternatively, the compounds of formula $I_{PDG}$ (R$^5$ and/or R$^8$≠OH) can be prepared by the reaction between a phosphonic acid of formula $I_D$ and an appropriate alcohol of formula HO—(CHR$^6$)—C(=O)—O—R$^9$, HO—CH$_2$—(CH$_2$)$_q$—OH, phenol, benzyl alcohol, 4-hydroxymethyl-5-methyl-[1,3]dioxol-2-one, 2-hydroxybenzyl alcohol being unsubstituted or substituted on the phenyl ring, 2-aminobenzyl alcohol being unsubstituted or substituted on the phenyl ring in the presence of a condensing reagent (e.g. PyBOP) and a suitable base (e.g. NEt$_3$, DIPEA) in a suitable solvent such as DMF and preferably at a temperature between RT and 45° C.

Alternatively, when R$^5$ represents phenyloxy and R$^8$ represents a group of formula NH—(CHR$^{10}$)—C(=O)—O—R$^9$ or NH—C(CH$_3$)$_2$—C(=O)—O—R$^9$, the respective compounds of formula $I_{PDG}$ can be prepared in a three-step procedure starting from the respective phosphonic acid of formula $I_D$:
1. a coupling reaction is performed with a phenol in the presence of a condensing reagent (e.g. PyBOP) and a suitable base (e.g. NEt$_3$, DIPEA) in a suitable solvent such as DMF and preferably at a temperature between RT and 45° C.;
2. a saponification reaction is performed using standard conditions such as NaOH in a mixture of water and a suitable organic solvent such as MeOH or EtOH; and finally
3. a coupling reaction is performed with an appropriate α-amino acid alkyl ester of formula NH$_2$—(CHR$^{10}$)—C(=O)—O—R$^9$ or NH$_2$—C(CH$_3$)$_2$—C(=O)—O—R$^9$ in the presence of a suitable base (e.g. NEt$_3$) and an activating mixture of reagents such as a combination of 2,2'-dipyridyl disulfide and PPh$_3$ in a suitable solvent such as anhydrous pyridine and preferably at a temperature of about 60° C.

Alternatively, when R$^5$ represents hydroxy and R$^8$ represents a group —O—(CH$_2$)—O—C(=O)—R$^9$, the compounds of formula $I_{PDG}$ can be prepared in a two-step procedure starting from the respective phosphonic acid of formula $I_D$:
1. a coupling reaction is performed with benzyl alcohol in the presence of a suitable base (e.g. NEt$_3$) and an activating mixture of reagents such as a combination of 2,2'-dipyridyl disulfide and PPh$_3$ in a suitable solvent such as anhydrous pyridine and preferably at a temperature of about 60° C. to give the mono-benzylated intermediate; and
2. a substitution reaction is performed with an appropriate halide derivative of formula X—(CH$_2$)—O—C(=O)—R$^9$, X being chloride, bromide or iodide, in the presence of a suitable base (e.g. NEt$_3$, DIPEA, DCMC) in a suitable solvent such as DMF, NMP or DMPU and preferably at a temperature between 45 and 90° C. The benzyl cleavage occurred simultaneously.

Preparation of the Various Synthesis Intermediates:
Preparation of the Compounds of Formula II The compounds of formula II can be prepared using the routes summarized in Scheme 2 and Scheme 2a hereafter.

Scheme 2

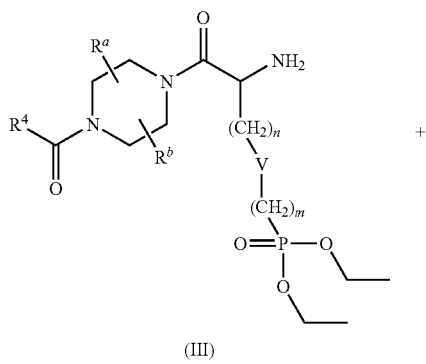

(III)

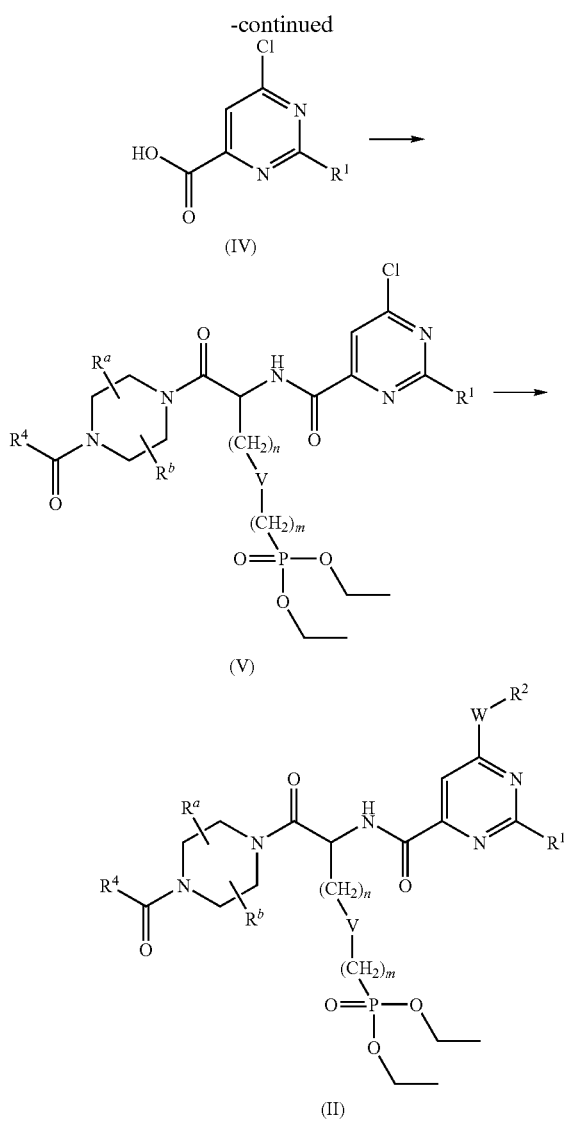

(IV)

(V)

(II)

The compound of formula V can be obtained (Scheme 2) by coupling a compound of formula III with a compound of formula IV using standard peptide coupling methods such as PyBOP, in the presence of a suitable base such as NEt₃, DIPEA or N-methylmorpholine and in a suitable solvent such as DCM, THF or DMF, preferably at a temperature around RT.

The resulting intermediate of formula V can then be converted into a compound of formula II wherein W is —NR³— by aromatic substitution reaction with an amine of formula HNR²R³ optionally in the presence of a suitable base such as NEt₃, DIPEA or N-methylmorpholine, the reaction being carried out in a suitable solvent such as DCM, THF, MeCN or DMF and preferably between RT and 70° C.

The intermediate of formula V can also be converted into a compound of formula II wherein W is —O— by aromatic substitution reaction with an alcohol of formula R²OH in the presence of a suitable base such as NaH, the reaction being carried out in a suitable solvent such as MeOH, THF, MeCN or DMF and preferably around RT.

The intermediate of formula V can furthermore be converted into a compound of formula II wherein W is a bond, using a reagent of formula R²—B(OR)₂, R being hydrogen or alkyl, using standard conditions for a Suzuki reaction, and preferably using a boronic acid or ester derivative R²—B(OR)₂ in the presence of a suitable base such as K₃PO₄ or K₂CO₃, in the presence of a suitable palladium catalyst such as tetrakis(triphenylphosphine)palladium or tris(dibenzylideneacetone)dipalladium, optionally in the presence of a suitable ligand such as triphenylphosphine, in a suitable solvent such as dioxane or a toluene/EtOH mixture, and preferably heating between 80° C. and 100° C. Besides, the intermediate of formula V can also be converted into a compound of formula II wherein W is a bond, using a reagent of formula R²—SnBu₃, using standard conditions for a Stille reaction, and preferably using a tributylstannane derivative R²—SnBu₃ in the presence of a suitable catalyst such as tetrakis(triphenylphosphine)palladium in a suitable solvent such as toluene, and preferably heating at about 110° C. Alternatively, the intermediate of formula V can also be converted into a compound of formula II wherein W is a bond, using a magnesium derivative of formula R²—MgBr, in the presence of a suitable iron catalyst such as iron(III)acetylacetonate, in a suitable solvent such as THF and at a temperature preferably around RT (see Fürstner A. et al. in *J. Am. Chem. Soc.* (2002), 13856-13863).

Alternatively, the intermediate of formula V can also be converted in a two step procedure into a compound of formula II wherein W is a bond, using a reagent of formula R—C≡CH (R² equals RCH₂CH₂), using standard conditions for a Sonogashira reaction, and preferably using an alkyne derivative R—C≡CH in the presence of a suitable base such as NEt₃, in the presence of a suitable palladium catalyst such as bis-(triphenylphosphine)palladium(II)-dichloride, in the presence of a suitable copper catalyst such as copper(I) iodide, in a suitable solvent such as DMF, and at RT. In a second step, the obtained intermediate can be converted into a compound of formula II by reducing the triple bond to the single bond in the presence of a suitable catalyst such as Raney Nickel, in a suitable solvent such as MeOH, at a temperature preferably around RT under a hydrogen atmosphere.

Scheme 2a

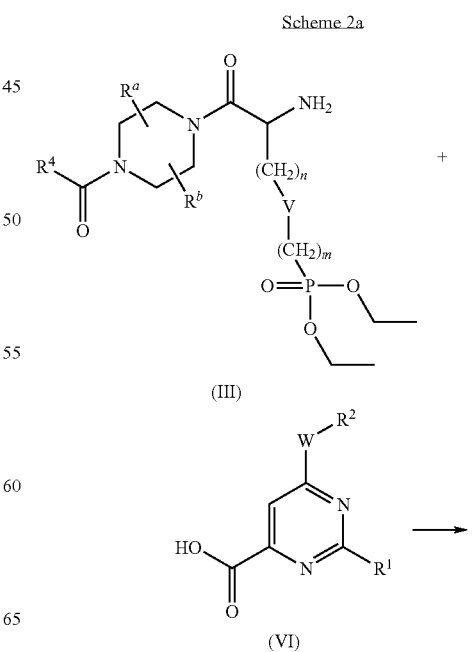

(III)

(VI)

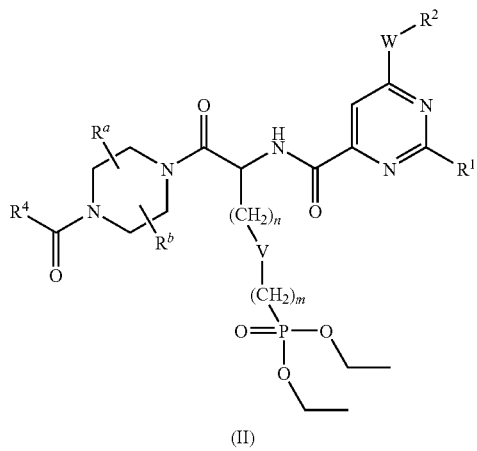

(II)

Alternatively, the compounds of formula II can be prepared as described in Scheme 2a by coupling a compound of formula III with a compound of formula VI using standard peptide coupling methods such as PyBOP, HOBT, EDCI hydrochloride, 1,3-dicyclohexylcarbodiimide, HATU, optionally in the presence of a suitable base such as NEt$_3$, DIPEA or N-methylmorpholine and in a suitable solvent such as DCM, THF or DMF, preferably at a temperature around RT.

Preparation of the Compounds of Formula III

The compounds of formula III wherein n is 1, V represents a bond and m is 0 can be prepared using the route summarized in Scheme 3 hereafter.

Scheme 3

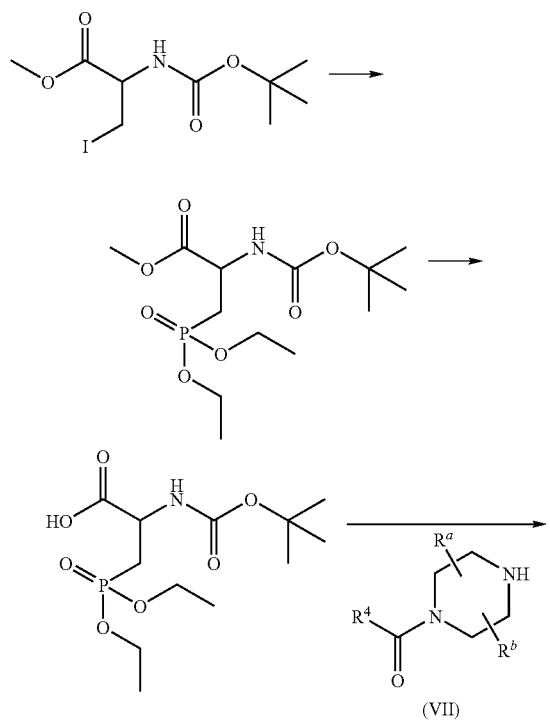

(VII)

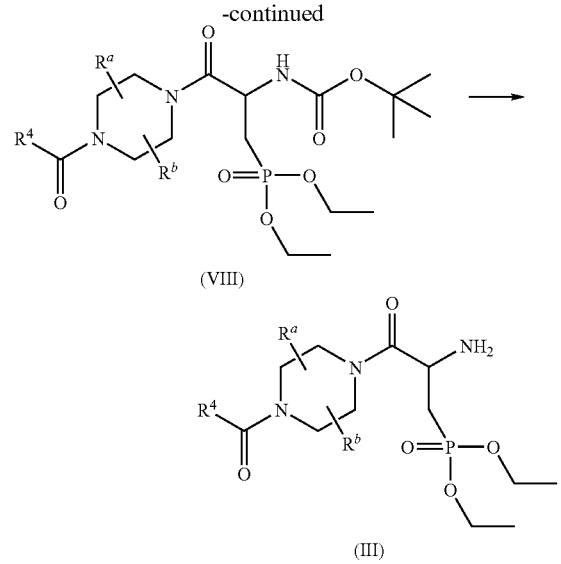

(VIII)

(III)

The compounds of formula VIII can be obtained in three steps starting from Boc-3-iodo-L-Ala-OMe or Boc-3-iodo-D-Ala-OMe: an Arbuzov reaction is performed (e.g. using P(OEt)$_3$ at reflux) followed by a saponification reaction using standard conditions such as NaOH or LiOH in a mixture of water and a suitable organic solvent such as THF, MeOH or EtOH; finally the obtained acid intermediate is coupled with a compound of formula VII using standard peptide coupling methods such as those described for the synthesis of compounds of formula II (see Scheme 2a). The compounds of formula III can then be obtained by standard acidic conditions for the removal of a Boc group that are well known to one skilled in the art.

The compounds of formula III wherein n is 2, V represents a bond and m is 0 can be prepared using the route summarized in Scheme 3a hereafter.

Scheme 3a

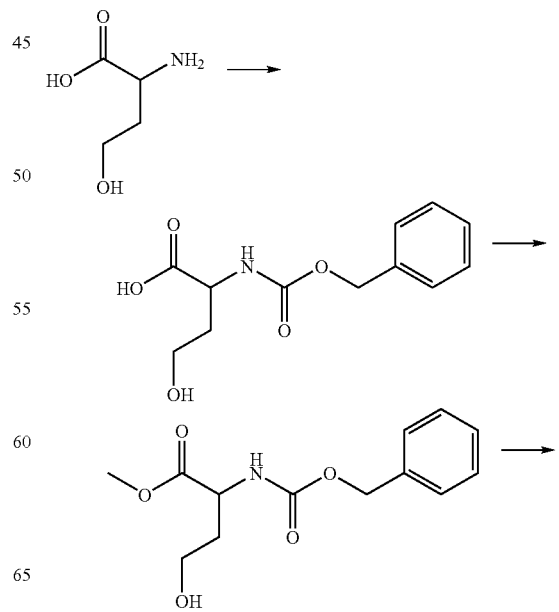

-continued

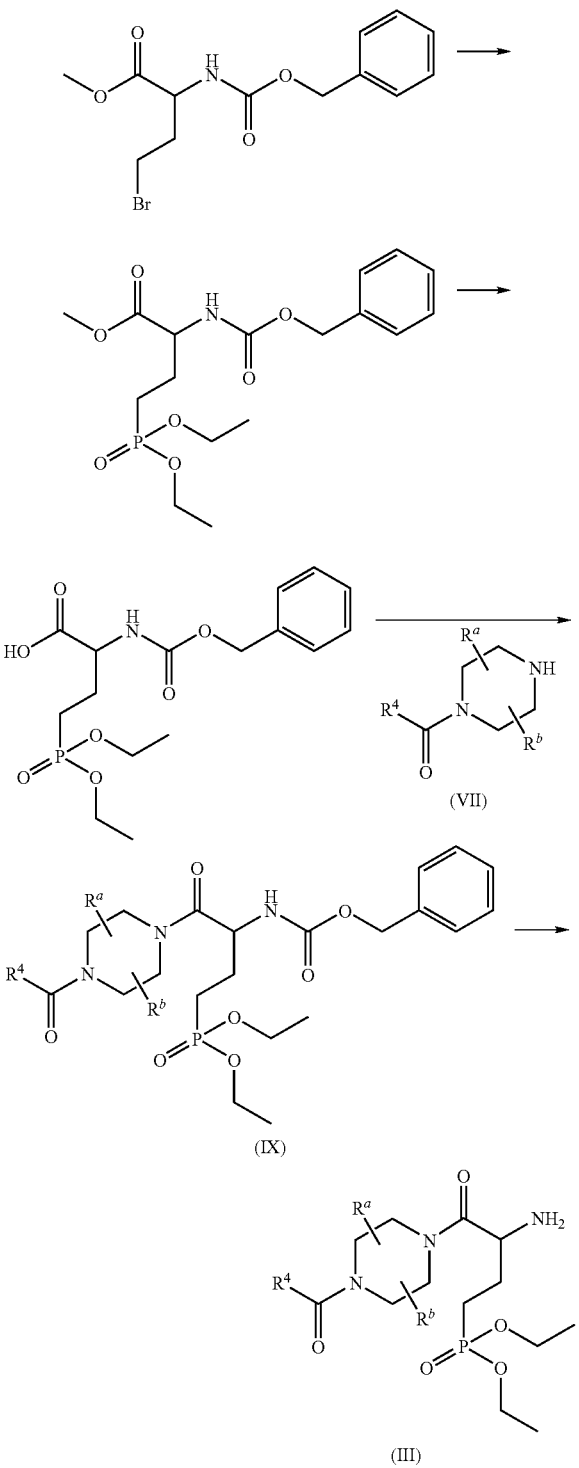

(III)

L-Homoserine or D-homoserine is first protected on the nitrogen atom with a Z group using standard conditions known to one skilled in the art. The dicyclohexylamine salt of the obtained molecule is prepared and the methyl ester is formed using MeI in DMF at a temperature around RT. The hydroxy function is then substituted by a bromide using standard conditions such as PPh₃ and CBr₄, in a suitable solvent such as DCM, preferably between 0° C. and RT. The next three steps leading to the compounds of formula IX are performed using conditions such as those already described for the synthesis of the compounds of formula VIII (see Scheme 3). The compounds of formula III can then be obtained by cleaving the Z protecting group using standard conditions known to one skilled in the art (e.g. hydrogenation with Pd/C in EtOH).

The compounds of formula III wherein n is 0, V represents a bond and m is 0 can be prepared using the route summarized in Scheme 3b hereafter.

Scheme 3b

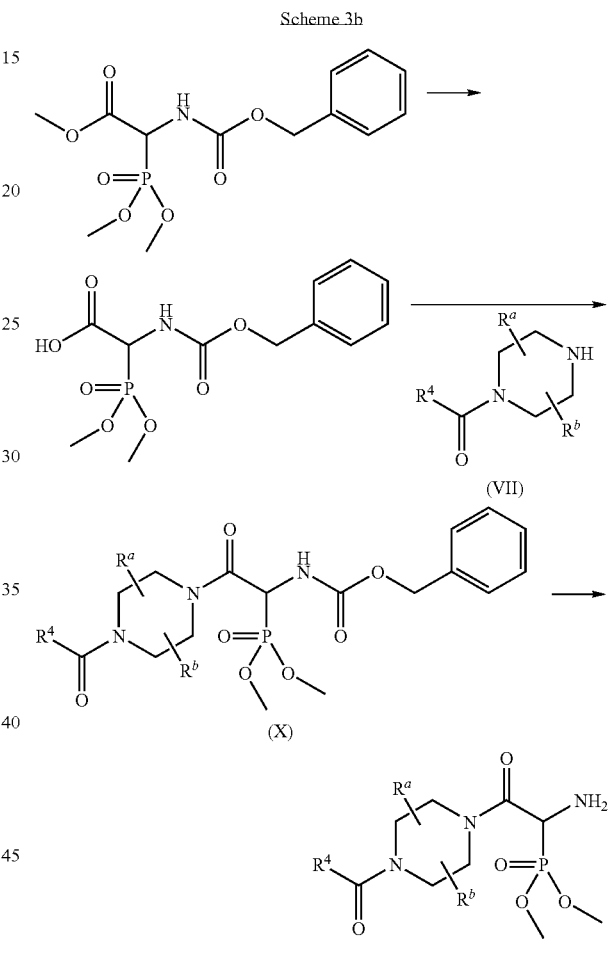

The compounds of formula X can be obtained in two steps starting from commercially available (dl)-Z-α-phosphonoglycine trimethyl ester: a saponification reaction is performed using standard conditions such as NaOH or LiOH in a mixture of water and a suitable organic solvent such as THF, MeOH or EtOH; the obtained acid intermediate is coupled with a compound of formula VII using standard peptide coupling methods such as those described for the synthesis of compounds of formula II (see Scheme 2a). The compounds of formula III can then be obtained by standard conditions for the removal of a Z group that are well known to one skilled in the art (e.g. hydrogenation with Pd/C in EtOH).

The compounds of formula III wherein n is 3, V represents a bond and m is 0 can be prepared using the route summarized in Scheme 3c hereafter.

Scheme 3c

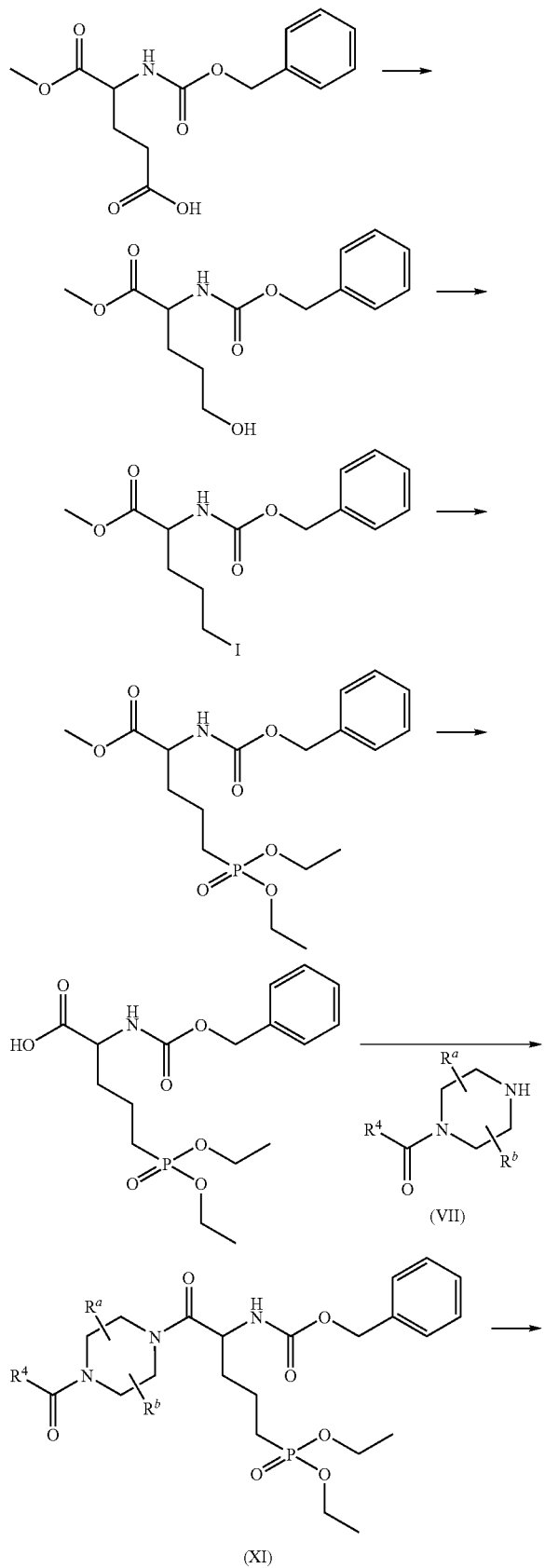

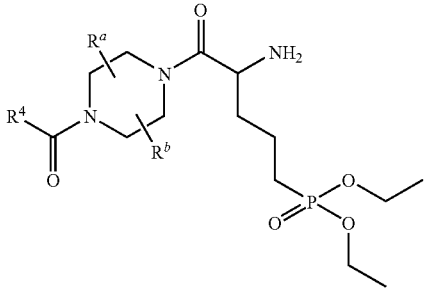

(III)

Cbz-(L)-Glu-OMe or Cbz-(D)-Glu-OMe can be reduced to the respective alcohol by transforming the acid to a mixed anhydride using, for instance, a chloroformate reagent, in the presence of a suitable base such as N-methylmorpholine, in a suitable solvent such as THF, and preferably at about −15° C. and subsequent reduction of the mixed anhydride with a suitable reducing agent such as $NaBH_4$ in presence of MeOH, at a temperature around −15° C. The hydroxy function can be substituted by iodide using standard conditions such as imidazole, $PPh_3$ and $I_2$, in a suitable solvent such as THF, preferably between 0° C. and RT. The next three steps leading to the compounds of formula XI can be performed using conditions such as those already described for the synthesis of the compounds of formula VIII (see Scheme 3). The compounds of formula III can then be obtained by standard conditions for the removal of a Cbz group that are well known to one skilled in the art (e.g. hydrogenation with Pd/C in MeOH).

The compounds of formula III wherein n is 1, V represents phenyl and m is 0 can be prepared using the route summarized in Scheme 3d hereafter.

Scheme 3d

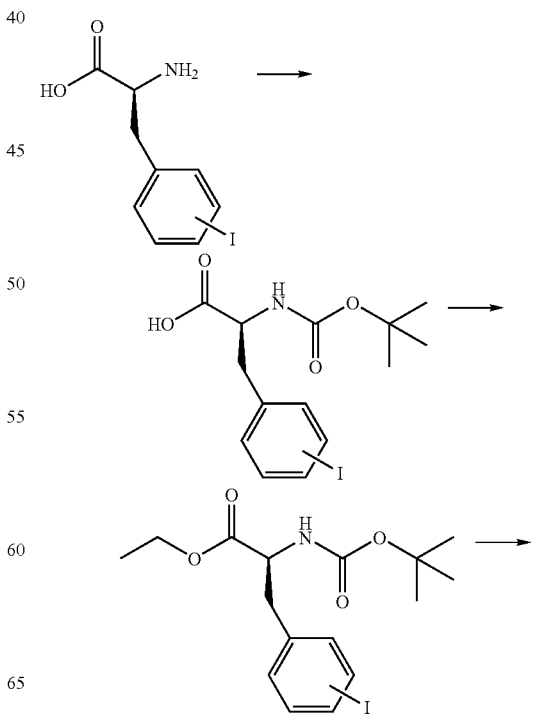

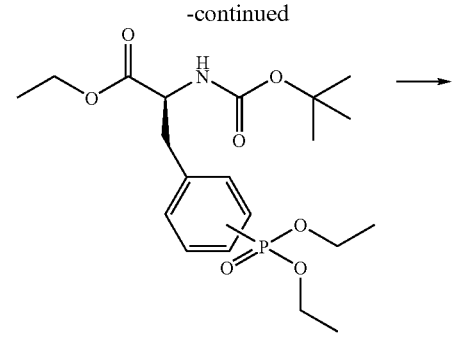

MeCN or toluene, and preferably heating around reflux temperature. The next three steps leading to the compounds of formula III can be performed using conditions such as those already described for the synthesis of the compounds of formula III in Scheme 3.

The compounds of formula III wherein n is 1, V represents phenyl and m is 1 can be prepared using the route summarized in Scheme 3e hereafter.

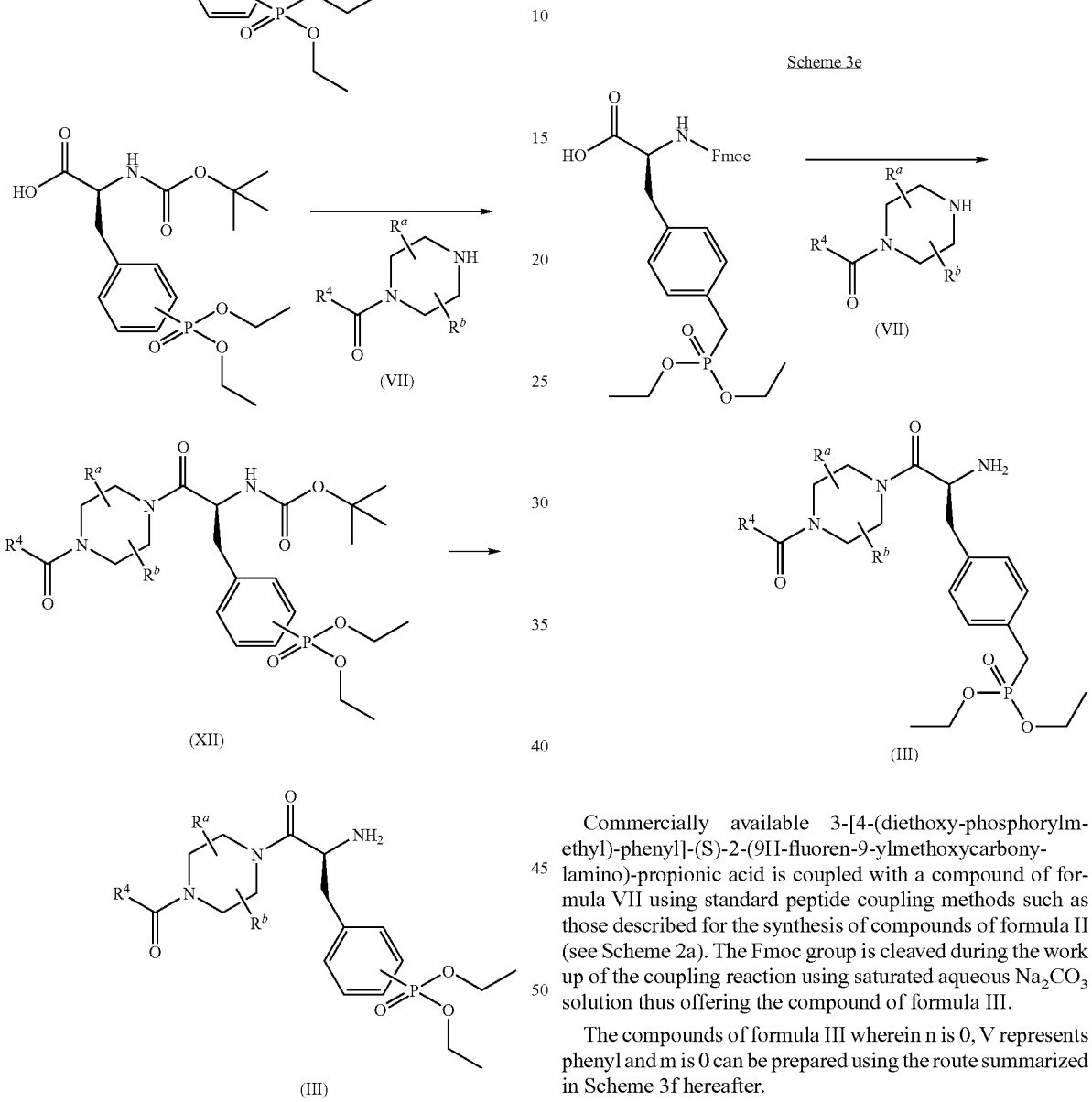

Commercially available 3-[4-(diethoxy-phosphorylmethyl)-phenyl]-(S)-2-(9H-fluoren-9-ylmethoxycarbonylamino)-propionic acid is coupled with a compound of formula VII using standard peptide coupling methods such as those described for the synthesis of compounds of formula II (see Scheme 2a). The Fmoc group is cleaved during the work up of the coupling reaction using saturated aqueous $Na_2CO_3$ solution thus offering the compound of formula III.

The compounds of formula III wherein n is 0, V represents phenyl and m is 0 can be prepared using the route summarized in Scheme 3f hereafter.

The Boc protected (L)-iodophenylalanine derivatives, if not commercially available, can be prepared starting from the (L)-iodophenylalanine compounds using standard conditions known to one skilled in the art. The acid function of the Boc protected (L)-iodophenylalanine derivatives can first be protected by formation of an ethyl ester using standard conditions known to one skilled in the art. The compounds thus obtained can then be converted into the diethyl phosphonate derivatives using diethyl phosphite, in the presence of a suitable base such as $NEt_3$, in the presence of a suitable palladium catalyst such as $Pd(PPh_3)_4$, in a suitable solvent such as

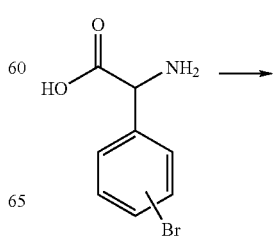

-continued

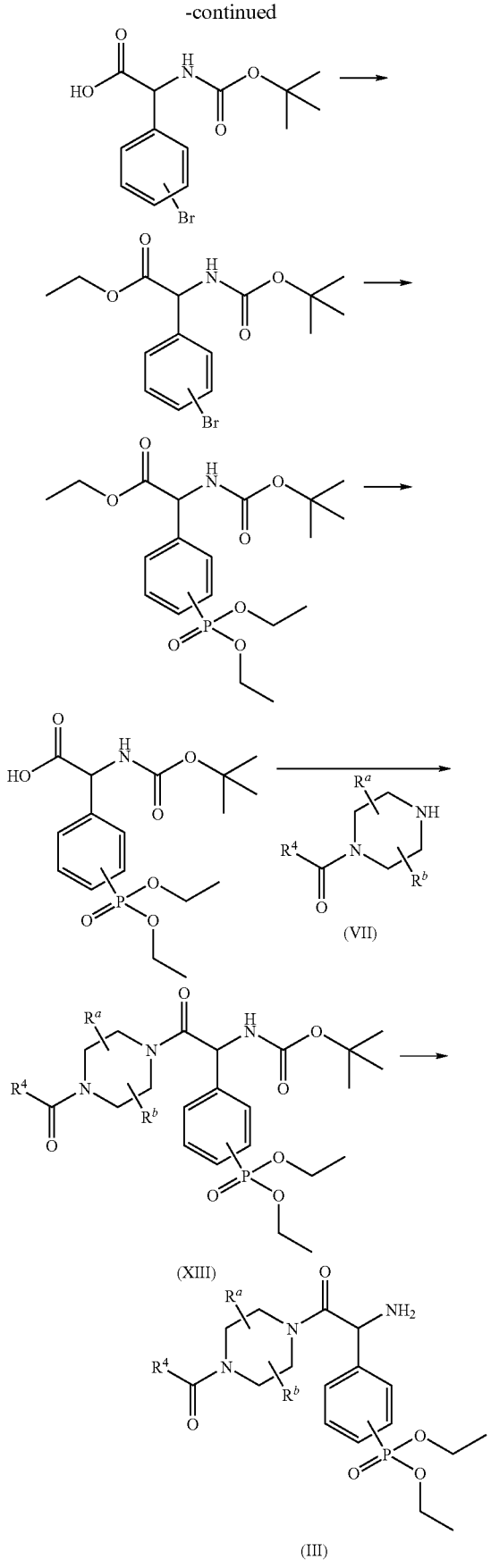

The compounds of formula III can be prepared in six steps starting from the commercially available DL-bromo-phenylglycines using conditions such as those already described for the synthesis of the compounds of formula III in Scheme 3d.

Preparation of the Compounds of Formula IV

The compounds of formula IV can be prepared using the route described in WO 2006/114774 (see general preparation routes, preparation of the compounds of formula IV, Scheme 4a).

Preparation of the Compounds of Formula VI

The compounds of formula VI can be prepared using the reaction shown in Scheme 4 hereafter.

Scheme 4

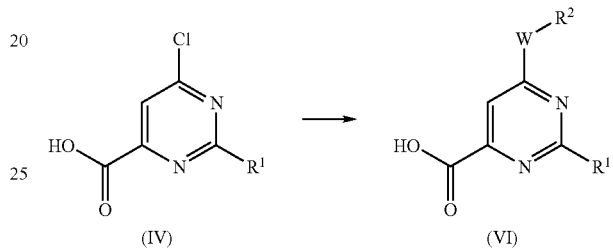

The intermediate of formula IV can be converted into a compound of formula VI wherein W is a bond, using a reagent of formula $R^2$—$B(OR)_2$, R being hydrogen or alkyl, using standard conditions for a Suzuki reaction such as those described for the synthesis of compounds of formula II wherein W is a bond (see Scheme 2). Alternatively, the intermediate of formula IV can be converted into a compound of formula VI wherein W is —$NR^3$— by aromatic substitution reaction with an amine of formula $HNR^2R^3$ using conditions such as those described for the synthesis of compounds of formula II wherein W is —$NR^3$— (see Scheme 2).

Preparation of the Compounds of Formula VII

The compounds of formula VII can be prepared using the route described in WO 2006/114774 (see general preparation routes, preparation of the compounds of formula V, Schemes 5 and 5a).

Particular embodiments of the invention are described in the following Examples, which serve to illustrate the invention in more detail without limiting its scope in any way.

EXAMPLES

Characterization Methods Used:

$^1$H-NMR: The NMR spectra were measured on a 400 MHz Brucker Avance.

The LC-MS retention times have been obtained using the following elution conditions:

LC-MS (A): A Zorbax® column (Agilent SB.Aq 5 μm, 4.6×50 mm) was used. The two elution solvents were as follows: solvent A=water+0.04% TFA; solvent B=MeCN. The eluent flow rate was 4.5 ml/min and the characteristics of the eluting mixture proportion in function of the time t from start of the elution are summarized in the table below (a linear gradient being used between two consecutive time points):

| t (min)       | 0  | 1  | 1.45 | 1.55 |
|---------------|----|----|------|------|
| Solvent A (%) | 95 | 5  | 5    | 95   |
| Solvent B (%) | 5  | 95 | 95   | 5    |

LC-MS (B): A X-terra® column (MS C18 5 µm, 2.1×50 mm) was used. The two elution solvents were as follows: solvent A=water+0.06% formic acid; solvent B=MeCN+0.06% formic acid. The eluent flow rate was 3 ml/min and the characteristics of the eluting mixture proportion in function of the time t from start of the elution are summarized in the table below (a linear gradient being used between two consecutive time points):

| t (min)       | 0  | 1  | 1.25 | 1.30 | 1.80 |
|---------------|----|----|------|------|------|
| Solvent A (%) | 95 | 5  | 5    | 95   | 95   |
| Solvent B (%) | 5  | 95 | 95   | 5    | 5    |

LC-MS (C): A Zorbax® column (Extend-C18 5 µm, 4.6×50 mm) was used. The two elution solvents were as follows: solvent A=water+0.1% conc. aq. ammonia; solvent B=MeCN. The eluent flow rate was 4.5 ml/min and the characteristics of the eluting mixture proportion in function of the time t from start of the elution are summarized in the table below (a linear gradient being used between two consecutive time points):

| t (min)       | 0  | 0.75 | 1.45 | 1.55 | 1.60 |
|---------------|----|------|------|------|------|
| Solvent A (%) | 95 | 5    | 5    | 95   | 95   |
| Solvent B (%) | 5  | 95   | 95   | 5    | 5    |

Preparative LC-MS Methods Used:

The purifications by preparative LC-MS have been performed using a Phenomenex® column unless otherwise specified in the relevant Example description, with the general conditions described hereafter.

A Phenomenex® column (Gemini 10u C18 110A Ax 50×21.2 mm) or a X-Terra® column (Prep MS C18 OBD™ 10u 30×75 mm) was used. The two elution solvents were as follows: solvent A=water+1% formic acid; solvent B=MeCN+1% formic acid. The eluent flow rate was 50 mL/min for the Phenomenex® column and 100 mL/min for the X-Terra® column. The characteristics of the eluting mixture proportion in function of the time t from start of the elution are summarized in the tables below (a linear gradient being used between two consecutive time points):

I) Preparative LC-MS (I):

| t (min)       | 0    | 0.4  | 2.6  | 3    | 3.4  | 3.8  | 3.9  | 5    |
|---------------|------|------|------|------|------|------|------|------|
| Solvent A (%) | 75.1 | 75.1 | 55.1 | 55.1 | 4.5  | 4.5  | 75.1 | 75.1 |
| Solvent B (%) | 24.9 | 24.9 | 44.9 | 44.9 | 95.5 | 95.5 | 24.9 | 24.9 |

II) Preparative LC-MS (II):

| t (min)       | 0    | 0.4  | 2.6  | 3    | 3.4  | 3.8  | 3.9  | 5    |
|---------------|------|------|------|------|------|------|------|------|
| Solvent A (%) | 65.1 | 65.1 | 45   | 45   | 4.5  | 4.5  | 65.1 | 65.1 |
| Solvent B (%) | 34.9 | 34.9 | 55   | 55   | 95.5 | 95.5 | 34.9 | 34.9 |

III) Preparative LC-MS (III):

| t (min)       | 0  | 0.4 | 2.6 | 3  | 3.4  | 3.8  | 3.9 | 5  |
|---------------|----|-----|-----|----|------|------|-----|----|
| Solvent A (%) | 60 | 60  | 40  | 40 | 4.5  | 4.5  | 60  | 60 |
| Solvent B (%) | 40 | 40  | 60  | 60 | 95.5 | 95.5 | 40  | 40 |

IV) Preparative LC-MS (IV):

| t (min)       | 0    | 0.4  | 2.6 | 3  | 3.4  | 3.8  | 3.9  | 5    |
|---------------|------|------|-----|----|------|------|------|------|
| Solvent A (%) | 55.1 | 55.1 | 35  | 35 | 4.5  | 4.5  | 55.1 | 55.1 |
| Solvent B (%) | 44.9 | 44.9 | 65  | 65 | 95.5 | 95.5 | 44.9 | 44.9 |

V) Preparative LC-MS (V):

| t (min)       | 0    | 0.6  | 3.3  | 3.9  | 4.5 | 5.1 | 5.2  | 6    |
|---------------|------|------|------|------|-----|-----|------|------|
| Solvent A (%) | 65.1 | 65.1 | 39.9 | 39.9 | 0   | 0   | 65.1 | 65.1 |
| Solvent B (%) | 34.9 | 34.9 | 60.1 | 60.1 | 100 | 100 | 34.9 | 34.9 |

Stationary Phases Used for CC:

The purifications by CC have been performed using silica gel unless otherwise specified. The reverse phase used is ISOLUTE® C18 from Biotage.

Example 1

4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid ethyl ester 1.1. (R)-2-tert-butoxycarbonylamino-3-(diethoxy-phosphoryl)-propionic acid methyl ester:

Boc-3-iodo-L-Ala-OMe (9.4 g) was dissolved in triethyl phosphite (100 mL). The mixture was heated at 130° C. overnight and evaporated to dryness to give a yellow oil (8.37 g). The compound was used in the next step without further purification.

LC-MS (A): $t_R$=0.85 min; $[M+H]^+$: 340.09.

1.2. (R)-2-tert-butoxycarbonylamino-3-(diethoxy-phosphoryl)-propionic acid:

An aq. solution of lithium hydroxide hydrate (2.07 g in 5 mL) was added to a solution of intermediate 1.1 (8.37 g) in THF (99 mL). The reaction mixture was stirred at RT overnight and DCM and a 1M HCl solution (60 mL) were added. The phases were separated and the aq. phase was extracted three times with DCM. The org. phases were combined, dried ($Na_2SO_4$) and evaporated off to give 5.8 g of the desired product as a white powder.

LC-MS (A): $t_R$=0.77 min; [M+H]$^+$: 326.13.

1.3. 4-[(R)-2-tent-butoxycarbonylamino-3-(diethoxy-phosphoryl)-propionyl]-piperazine-1-carboxylic acid ethyl ester:

HOBT hydrate (98 mg) and EDCI hydrochloride (123 mg) were added to a solution of intermediate 1.2 (200 mg) and DIPEA (0.42 mL) in THF/DCM (0.6 mL/2.4 mL). After stirring at RT for 10 min, 1-ethoxycarbonylpiperazine (97 mg) was added and the stirring was continued overnight at RT. DCM and an aq. NaHCO$_3$ solution were added to the mixture and the phases were separated. The aq. phase was extracted with DCM and the combined org. phases were washed with a NaCl solution, dried (Na$_2$SO$_4$) and evaporated off. The crude was purified by CC (eluent: gradient from EA to EA/MeOH 25/1). After HV drying, the desired compound was obtained as a colourless resin (194 mg).

LC-MS (A): $t_R$=0.86 min; [M+H]$^+$: 466.05.

1.4. 4-[(R)-2-amino-3-(diethoxy-phosphoryl)-propionyl]-piperazine-1-carboxylic acid ethyl ester hydrochloride salt:

Intermediate 1.3 (192 mg) was dissolved in EA (0.2 mL) and a 4M HCl solution in dioxane (0.4 mL). The reaction mixture was stirred at RT for 4.5 h and evaporated off. After HV drying, the desired compound was obtained as a colourless resin (199 mg).

LC-MS (A): $t_R$=0.65 min; [M+H]$^+$: 366.04.

1.5. (S)-3-hydroxypyrrolidine-1-carboxylic acid tert-butyl ester:

Di-tert-butyl-dicarbonate (27.5 g) was added portionwise to a solution of (S)-3-hydroxypyrrolidine (10 g) and NEt$_3$ (32 mL) in DCM (240 mL). The reaction mixture was stirred overnight at RT. Water was added and the org. phase was separated. It was washed with sat. aq. NH$_4$Cl, sat. aq. NaHCO$_3$ and sat. aq. NaCl. The org. phase was dried (Na$_2$SO$_4$) and evaporated off to afford the desired compound (21.4 g).

$^1$H-NMR (CDCl$_3$): β=4.43 (br. s, 1H); 3.40 (m, 4H); 2.70 (m, 1H); 1.93 (m, 2H); 1.46 (s, 9H).

1.6. (S)-3-methoxy-pyrrolidine-1-carboxylic acid tert-butyl ester:

To an ice-cold solution of intermediate 1.5 (22 g) in THF (300 mL) was added NaH (7.7 g, 55% dispersion in mineral oil) portionwise. The reaction mixture was stirred for 30 min at RT, cooled down to 0° C. and MeI (11 mL) was added dropwise. Stirring was continued for additional 2 h at RT. Water and ethanolamine (14 mL) were added to the reaction mixture that was stirred for 15 min. The org. phase was separated and the aq. phase was extracted with DCM three times. The combined org. phases were washed with sat. aq. NaCl, dried (Na$_2$SO$_4$) and evaporated off to afford a yellow oil (27.5 g).

$^1$H-NMR (CDCl$_3$): δ=3.94 (br. s, 1H); 3.44 (m, 4H); 3.35 (s, 3H); 1.99 (m, 2H); 1.48 (s, 9H).

1.7. (S)-3-methoxy-pyrrolidine hydrochloride salt:

Intermediate 1.6 (27.5 g) was dissolved in 1M HCl in EA (300 mL) and 3M HCl in EA (50 mL) was added. The reaction mixture was stirred overnight at RT and the solvent was evaporated off. The residue was taken up in Et$_2$O (500 mL) and the compound precipitated out. The suspension was stirred for 1 h, filtered off and the powder washed with Et$_2$O. HV drying afforded the desired hydrochloride salt (13.9 g).

$^1$H-NMR (CDCl$_3$): δ=9.84 (br. s, 1H); 4.10 (br s, 1H); 3.43 (m, 4H); 3.33 (s, 3H); 2.19 (m, 1H); 2.04 (m, 1H).

1.8. 6-((S)-3-methoxy-pyrrolidin-1-yl)-2-phenyl-pyrimidine-4-carboxylic acid:

6-chloro-2-phenyl-pyrimidine-4-carboxylic acid (14.3 g; prepared as described in WO 2006/114774, Example 24, intermediate 24.3), intermediate 1.7 (10 g) and DIPEA (23 mL) were dissolved in THF (191 mL). The reaction mixture was stirred at 60° C. for 48 h. Water and DCM were added and the phases were separated. The aq. phases were washed with DCM and the combined org. phases were dried (Na$_2$SO$_4$) and evaporated off. CC (DCM/MeOH 9/1) of the crude yielded the desired compound (13.2 g).

LC-MS (A): $t_R$=0.74 min; [M+H]$^+$: 300.42.

1.9. 4-((R)-3-(diethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester:

To a solution of intermediate 1.8 (135 mg) in THF/DCM (0.4 mL/1.6 mL) were sequentially added DIPEA (0.309 mL), HOBT hydrate (83 mg) and EDCI hydrochloride (104 mg). After stirring at RT for 5 min, intermediate 1.4 (194 mg) was added and the stirring was continued overnight at RT. DCM and an aq. NaHCO$_3$ solution were added to the mixture and the phases were separated. The org. phase was dried (Na$_2$SO$_4$) and evaporated off. The crude was purified by CC (eluent: gradient from EA/MeOH 100/1 to EA/MeOH 9/1). After HV drying, the desired compound was obtained as a colourless resin (131 mg).

LC-MS (A): $t_R$=1.00 min; [M+H]$^+$: 646.95.

1.10. 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid ethyl ester:

To an ice-cold solution of intermediate 1.9 (129 mg) in anhydrous MeCN (0.6 mL) was added trimethylsilyl bromide (0.516 mL) dropwise. The reaction mixture was allowed to warm to RT and was stirred at RT until completion. Water (1 mL) was added. After stirring at RT for 3 h, water was added and the mixture was extracted 5 times with DCM. The combined org. phases were dried (Na$_2$SO$_4$) and evaporated off. The crude was purified by CC (reverse phase; eluent: gradient from water/TFA 100/1 to MeCN/TFA 100/1). After HV drying, the desired compound was obtained as a colourless resin (94 mg).

LC-MS (A): $t_R$=0.82 min; [M+H]$^+$: 590.97.

Example 2

4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester 2.1. 4-benzyl-piperazine-1-carboxylic acid butyl ester:

To a solution of 1-benzyl-piperazine (1.97 ml) and NEt$_3$ (1.9 ml) in DCM (100 ml) was added n-butyl chloroformate (1.47 ml). The mixture was stirred at RT for 2 h. Water was added, the org. phase separated, dried (Na$_2$SO$_4$) and evaporated off to give a yellow oil (3.13 g).

LC-MS (A): $t_R$=0.73 min; [M+H]$^+$: 277.42.

2.2. Piperazine-1-carboxylic acid butyl ester:

Intermediate 2.1 (3.1 g) was hydrogenated in EtOH (100 ml) with Pd/C (wet, 5%, 480 mg) for 24 h. The mixture was filtered through celite and evaporated off. HV drying afforded the desired compound as a pale yellow liquid (2.04 g).

LC-MS (A): $t_R$=0.54 min; [M+H+MeCN]$^-$: 226.39.

2.3. 4-[(R)-2-tert-butoxycarbonylamino-3-(diethoxy-phosphoryl)-propionyl]-piperazine-1-carboxylic acid butyl ester:

This compound was prepared using a method analogous to that of Example 1, step 1.3, intermediate 2.2 replacing 1-ethoxycarbonylpiperazine.

LC-MS (A): $t_R$=0.94 min; [M+H]$^+$: 494.18.

2.4. 4-[(R)-2-amino-3-(diethoxy-phosphoryl)-propionyl]-piperazine-1-carboxylic acid butyl ester hydrochloride salt:

This compound was prepared using a method analogous to that of Example 1, step 1.4, intermediate 2.3 replacing intermediate 1.3.

LC-MS (A): $t_R$=0.73 min; [M+H]$^+$: 394.08.

2.5. 4-((R)-3-(diethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester:

This compound was prepared using a method analogous to that of Example 1, step 1.9, intermediate 2.4 replacing intermediate 1.4.

LC-MS (A): $t_R$=1.05 min; [M+H]$^+$: 675.14.

2.6. 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester:

This compound was prepared using a method analogous to that of Example 1, step 1.10, intermediate 2.5 replacing intermediate 1.9.

LC-MS (A): $t_R$=0.88 min; [M+H]$^+$: 618.96.

Example 3

4-((S)-2-{[6-((S)-3-methoxy-pyrrolidin-1-yl)-2-phenyl-pyrimidine-4-carbonyl]-amino}-3-phosphono-propionyl)-piperazine-1-carboxylic acid ethyl ester 3.1. (S)-2-tent-butoxycarbonylamino-3-(diethoxy phosphoryl)-propionic acid methyl ester:

This compound was prepared using a method analogous to that of Example 1, step 1.1, Boc-3-iodo-D-Ala-OMe replacing Boc-3-iodo-L-Ala-OMe.

LC-MS (A): $t_R$=0.84 min; [M+H]$^+$: 340.32.

3.2. (S)-2-tent-butoxycarbonylamino-3-(diethoxy-phosphoryl)-propionic acid:

This compound was prepared using a method analogous to that of Example 1, step 1.2, intermediate 3.1 replacing intermediate 1.1.

LC-MS (A): $t_R$=0.77 min; [M+H]$^+$: 326.29.

3.3. 4-[(S)-2-tert-butoxycarbonylamino-3-(diethoxy-phosphoryl)-propionyl]-piperazine-1-carboxylic acid ethyl ester:

This compound was prepared using a method analogous to that of Example 1, step 1.3, intermediate 3.2 replacing intermediate 1.2.

LC-MS (A): $t_R$=0.85 min; [M+H]$^+$: 466.21.

3.4. 4-[(S)-2-amino-3-(diethoxy-phosphoryl)-propionyl]-piperazine-1-carboxylic acid ethyl ester hydrochloride salt:

This compound was prepared using a method analogous to that of Example 1, step 1.4, intermediate 3.3 replacing intermediate 1.3.

LC-MS (A): $t_R$=0.66 min; [M+H]$^+$: 366.12.

3.5. 4-((S)-3-(diethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester:

This compound was prepared using a method analogous to that of Example 1, step 1.9, intermediate 3.4 replacing intermediate 1.4.

LC-MS (A): $t_R$=0.98 min; [M+H]$^+$: 647.23.

3.6. 4-((S)-2-{[6-((S)-3-methoxy-pyrrolidin-1-yl)-2-phenyl-pyrimidine-4-carbonyl]-amino}-3-phosphono-propionyl)-piperazine-1-carboxylic acid ethyl ester:

This compound was prepared using a method analogous to that of Example 1, step 1.10, intermediate 3.5 replacing intermediate 1.9. The product was however purified by CC (eluent: gradient from CHCl$_3$ to CHCl$_3$/MeOH 1/1).

LC-MS (A): $t_R$=0.81 min; [M+H]$^+$: 591.18.

Example 4

4-((S)-2-{[6-((S)-3-methoxy-pyrrolidin-1-yl)-2-phenyl-pyrimidine-4-carbonyl]-amino}-4-phosphono-butyryl)-piperazine-1-carboxylic acid ethyl ester 4.1. (S)-2-benzyloxycarbonylamino-4-hydroxy-butyric acid:

To an ice-cooled solution of H-Hse-OH (3 g) in dioxane/2M NaOH (100 mL/25 mL) was added benzyl chloroformate (4 mL) dropwise over 15 min. The reaction mixture was allowed to warm to RT and was stirred overnight at RT. The solvent was evaporated off and the aq. residue was extracted with Et$_2$O and acidified with a 2M HCl solution. The aq. phase was extracted with DCM. The DCM layers were combined, dried (Na$_2$SO$_4$) and evaporated off to give the desired product as a white powder (4.13 g).

LC-MS (A): $t_R$=0.72 min; [M+H]$^+$: 254.36.

4.2. (S)-2-benzyloxycarbonylamino-4-hydroxy-butyric acid dicyclohexylamine salt:

To a solution of intermediate 4.1 (8.9 g) in EtOH (77 mL) was added dropwise dicyclohexylamine (7 mL). The solvent was removed and the white powder was suspended in Et$_2$O. The suspension was filtered off and the white solid (12.1 g) was dried in vacuo.

LC-MS (A): $t_R$=0.71 min.

4.3. (S)-2-benzyloxycarbonylamino-4-hydroxy-butyric acid methyl ester:

MeI (2.1 mL) was added dropwise to a suspension of intermediate 4.2 (12.1 g) in anhydrous DMF (196 mL). The reaction mixture was stirred overnight at RT. 1 more equivalent of MeI was added, and after 6 h stirring 2 more equivalents were added. The reaction mixture was stirred overnight and the solvent was removed. The residue was taken up in EA/water and the org. phase was washed with a NaCl solution, dried (Na$_2$SO$_4$) and evaporated off. The crude was purified by CC (Et$_2$O) to give the desired compound as a colourless resin (4.2 g).

LC-MS (A): $t_R$=0.79 min; [M+H]$^+$: 268.30.

4.4. (S)-2-benzyloxycarbonylamino-4-bromo-butyric acid methyl ester:

PPh$_3$ on resin (1.6 mmol/g, 12.4 g) was added to an ice-cooled solution of intermediate 4.3 (2.4 g) and CBr$_4$ (6.7 g) in anhydrous DCM (120 mL). The reaction mixture was stirred at 0° C. for 2 h and was allowed to warm to RT. The resin was filtered off and the solution evaporated off. The crude was purified by CC (EA/Hept 1/3) to give the desired compound as a colourless resin (1.7 g).

LC-MS (A): $t_R$=0.86 min; [M+H]$^+$: 331.89.

4.5. (S)-2-benzyloxycarbonylamino-4-(diethoxy-phosphoryl)-butyric acid methyl ester:

This compound was prepared using a method analogous to that of Example 1, step 1.1, intermediate 4.4 replacing Boc-3-iodo-L-Ala-OMe. The compound was however purified by CC (EA/Hept 1/3 to 1/0).

LC-MS (A): $t_R$=0.90 min; [M+H]$^+$: 388.24.

4.6. (S)-2-benzyloxycarbonylamino-4-(diethoxy-phosphoryl)-butyric acid:

This compound was prepared using a method analogous to that of Example 1, step 1.2, intermediate 4.5 replacing intermediate 1.1.

LC-MS (A): $t_R$=0.83 min; [M+H]$^+$: 374.36.

4.7. 4-[(S)-2-benzyloxycarbonylamino-4-(diethoxy-phosphoryl)-butyryl]-piperazine-1-carboxylic acid ethyl ester:

This compound was prepared using a method analogous to that of Example 1, step 1.9, intermediate 4.6 replacing intermediate 1.8 and 1-ethoxycarbonylpiperazine replacing intermediate 1.4. The compound was however purified twice by CC (EA).

LC-MS (A): $t_R$=0.91 min; [M+H]$^+$: 514.24.

4.8. 4-[(S)-2-amino-4-(diethoxy-phosphoryl)-butyryl]-piperazine-1-carboxylic acid ethyl ester:

This compound was prepared using a method analogous to that of Example 2, step 2.2, intermediate 4.7 replacing intermediate 2.1, however using MeOH instead of EtOH.

LC-MS (A): $t_R$=0.66 min; [M+H]$^+$: 380.32.

4.9. 4-((S)-4-(diethoxy-phosphoryl)-2-{[6-((S)-3-methoxy-pyrrolidin-1-yl)-2-phenyl-pyrimidine-4-carbonyl]-amino}-butyryl)-piperazine-1-carboxylic acid ethyl ester:

This compound was prepared using a method analogous to that of Example 1, step 1.3, intermediate 4.8 replacing 1-ethoxycarbonylpiperazine and intermediate 1.8 replacing intermediate 1.2. The product was however purified by CC (eluent: gradient from Hept to EA followed by gradient from EA to EA/MeOH 1/1), followed by preparative TLC (EA/MeOH 30/1).

LC-MS (A): $t_R$=1.01 min; [M+H]$^+$: 660.304.

4.10. 4-((S)-2-{[6-((S)-3-methoxy-pyrrolidin-1-yl)-2-phenyl-pyrimidine-4-carbonyl]-amino}-4-phosphono-butyryl)-piperazine-1-carboxylic acid ethyl ester:

This compound was prepared using a method analogous to that of Example 1, step 1.10, intermediate 4.9 replacing intermediate 1.9. The crude was purified by CC (eluent: gradient from CHCl$_3$ to CHCl$_3$/MeOH 1/1).

LC-MS (A): $t_R$=0.85 min; [M+H]$^+$: 605.03.

Example 5

4-((S)-2-{[6-((S)-3-methoxy-pyrrolidin-1-yl)-2-phenyl-pyrimidine-4-carbonyl]-amino}-4-phosphono-butyryl)-piperazine-1-carboxylic acid butyl ester 5.1. 4-[(S)-2-benzyloxycarbonylamino-4-(diethoxy-phosphoryl)-butyryl]-piperazine-1-carboxylic acid butyl ester:

This compound was prepared using a method analogous to that of Example 1, step 1.9, intermediate 4.6 replacing intermediate 1.8 and intermediate 2.2 replacing intermediate 1.4. The product was however purified twice by CC (eluent: gradient from EA/MeOH 10/1 to EA/MeOH 1/1, then gradient from EA to EA/MeOH 95/5).

LC-MS (A): $t_R$=0.96 min; [M+H]$^+$: 542.29.

5.2. 4-[(S)-2-amino-4-(diethoxy-phosphoryl)-butyryl]-piperazine-1-carboxylic acid butyl ester:

This compound was prepared using a method analogous to that of Example 2, step 2.2, intermediate 5.1 replacing intermediate 2.1, however using MeOH instead of EtOH.

LC-MS (A): $t_R$=0.69 min; [M+H]$^+$: 408.18.

5.3. 4-((S)-4-(diethoxy-phosphoryl)-2-{[6-((S)-3-methoxy-pyrrolidin-1-yl)-2-phenyl-pyrimidine-4-carbonyl]-amino}-butyryl)-piperazine-1-carboxylic acid butyl ester:

This compound was prepared using a method analogous to that of Example 1 step 1.3, intermediate 5.2 replacing 1-ethoxycarbonylpiperazine and intermediate 1.8 replacing intermediate 1.2. The crude was however purified by CC (eluent: gradient from EA to EA/MeOH 9/1).

LC-MS (A): $t_R$=1.06 min; [M+H]$^+$: 689.24.

5.4. 4-((S)-2-{[6-((S)-3-methoxy-pyrrolidin-1-yl)-2-phenyl-pyrimidine-4-carbonyl]-amino}-4-phosphono-butyryl)-piperazine-1-carboxylic acid butyl ester:

This compound was prepared using a method analogous to that of Example 1, step 1.10, intermediate 5.3 replacing intermediate 1.9.

LC-MS (A): $t_R$=0.91 min; [M+H]$^+$: 633.13.

Example 6

4-((S)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester 6.1. 4-[(S)-2-tert-butoxycarbonylamino-3-(diethoxy-phosphoryl)-propionyl]-piperazine-1-carboxylic acid butyl ester:

This compound was prepared using a method analogous to that of Example 1, step 1.3, intermediate 3.2 replacing intermediate 1.2 and intermediate 2.2 replacing 1-ethoxycarbonylpiperazine.

LC-MS (A): $t_R$=0.94 min; [M+H]$^+$: 494.26.

6.2. 4-[(S)-2-amino-3-(diethoxy-phosphoryl)-propionyl]-piperazine-1-carboxylic acid butyl ester hydrochloride salt:

This compound was prepared using a method analogous to that of Example 1, step 1.4, intermediate 6.1 replacing intermediate 1.3.

LC-MS (A): $t_R$=0.74 min; [M+H]$^+$: 394.18.

6.3. 4-((S)-3-(diethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester:

This compound was prepared using a method analogous to that of Example 1 step 1.9, intermediate 6.2 replacing intermediate 1.4.

LC-MS (A): $t_R$=1.05 min; [M+H]$^+$: 675.13.

6.4. 4-((S)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester:

This compound was prepared using a method analogous to that of Example 1, step 1.10, intermediate 6.3 replacing intermediate 1.9. The crude was purified by CC (eluent: gradient from CHCl$_3$ to CHCl$_3$/MeOH 1/1).

LC-MS (A): $t_R$=0.88 min; [M+H]$^+$: 619.12.

Example 7

4-{(S)-2-[(2-phenyl-6-pyrazol-1-yl-pyrimidine-4-carbonyl)-amino]-4-phosphono-butyryl}-piperazine-1-carboxylic acid butyl ester 7.1. 4-[(S)-2-[(6-chloro-2-phenyl-pyrimidine-4-carbonyl)-amino]-4-(diethoxy-phosphoryl)-butyryl]-piperazine-1-carboxylic acid butyl ester:

To a solution of 6-chloro-2-phenyl-pyrimidine-4-carboxylic acid (334 mg) in DCM (10 mL) was added PyBOP (815 mg), intermediate 5.2 (580 mg) and DIPEA (0.268 mL). The solution was stirred at RT for 24 h. It was diluted with DCM (50 mL) and washed with 2M Na$_2$CO$_3$, 1M NaHSO$_4$ and sat. aq. NaCl. The org. phase was dried (Na$_2$SO$_4$) and evaporated off. The crude was purified by CC (DCM/acetone 1/0 to 6/3) to afford the desired product as brownish foam (680 mg).

LC-MS (A): $t_R$=1.08 min; [M+H]$^+$: 623.96.

7.2. 4-{(S)-4-(diethoxy-phosphoryl)-2-[(2-phenyl-6-pyrazol-1-yl-pyrimidine-4-carbonyl)-amino]-butyryl}-piperazine-1-carboxylic acid butyl ester:

Pyrazole (7 µL) was added to a suspension of NaH (60% dispersion in mineral oil, 5.3 mg) in THF (0.5 mL). The suspension was stirred at RT for 30 min and a solution of intermediate 7.1 (55 mg) in THF (0.5 mL) was added. The reaction mixture was stirred at RT for 48 h. Water and DCM were added, the phases were separated and the org. phase was dried (Na$_2$SO$_4$) and evaporated off to afford the crude compound (30 mg). No further purification was performed.

LC-MS (B): $t_R$=1.17 min; [M+H]$^+$: 656.35.

7.3. 4-{(S)-2-[(2-phenyl-6-pyrazol-1-yl-pyrimidine-4-carbonyl)-amino]-4-phosphono-butyryl}-piperazine-1-carboxylic acid butyl ester:

This compound was prepared using a method analogous to that of Example 1, step 1.10, intermediate 7.2 replacing intermediate 1.9. The crude was purified by preparative LC-MS (I).

LC-MS (A): $t_R$=0.94 min; [M+H]$^+$: 599.96.

Example 8

4-((S)-2-{[6-(4-methyl-pyrazol-1-yl)-2-phenyl-pyrimidine-4-carbonyl]-amino}-4-phosphono-butyryl)-piperazine-1-carboxylic acid butyl ester 8.1. 4-((S)-4-(diethoxy-phosphoryl)-2-{[6-(4-methyl-pyrazol-1-yl)-2-phenyl-pyrimidine-4-carbonyl]-amino}-butyryl)-piperazine-1-carboxylic acid butyl ester:

This compound was prepared using a method analogous to that of Example 7, step 7.2, 4-methylpyrazole replacing pyrazole.

LC-MS (B): $t_R$=1.20 min; [M+H]$^+$: 670.40.

8.2. 4-((S)-2-{[6-(4-methyl-pyrazol-1-yl)-2-phenyl-pyrimidine-4-carbonyl]-amino}-4-phosphono-butyryl)-piperazine-1-carboxylic acid butyl ester:

This compound was prepared using a method analogous to that of Example 1, step 1.10, intermediate 8.1 replacing intermediate 1.9. The crude was purified by preparative LC-MS (I).

LC-MS (A): $t_R$=0.97 min; [M+H]$^+$: 613.94.

Example 9

4-[(S)-2-({2-phenyl-6-[(S)-(tetrahydro-furan-3-yl)oxy]-pyrimidine-4-carbonyl}-amino)-4-phosphono-butyryl]-piperazine-1-carboxylic acid butyl ester 9.1. 4-[(S)-4-(diethoxy-phosphoryl)-2-({2-phenyl-6-[(S)-(tetrahydro-furan-3-yl)oxy]-pyrimidine-4-carbonyl}-amino)-butyryl]-piperazine-1-carboxylic acid butyl ester:

This compound was prepared using a method analogous to that of Example 7, step 7.2, (S)-(+)-3-hydroxytetrahydrofurane replacing pyrazole, however using DMF instead of THF.

LC-MS (A): $t_R$=1.07 min; [M+H]$^+$: 675.91.

9.2. 4-[(S)-2-({2-phenyl-6-[(S)-(tetrahydro-furan-3-yl)oxy]-pyrimidine-4-carbonyl}-amino)-4-phosphono-butyryl]-piperazine-1-carboxylic acid butyl ester:

This compound was prepared using a method analogous to that of Example 1, step 1.10, intermediate 9.1 replacing intermediate 1.9. The crude was purified by preparative LC-MS (I).

LC-MS (A): $t_R$=0.92 min; [M+H]$^+$: 619.97.

Example 10

4-{(S)-2-[(2-phenyl-6-pyrrolidin-1-yl-pyrimidine-4-carbonyl)-amino]-4-phosphono-butyryl}-piperazine-1-carboxylic acid butyl ester 10.1. 4-{(S)-4-(diethoxy-phosphoryl)-2-[(2-phenyl-6-pyrrolidin-1-yl-pyrimidine-4-carbonyl)-amino]-butyryl}-piperazine-1-carboxylic acid butyl ester:

This compound was prepared using a method analogous to that of Example 7, step 7.2, pyrrolidine replacing pyrazole. The compound was however not purified.

LC-MS (A): $t_R$=1.09 min; [M+H]$^+$: 659.05.

10.2. 4-{(S)-2-[(2-phenyl-6-pyrrolidin-1-yl-pyrimidine-4-carbonyl)-amino]-4-phosphono-butyryl}-piperazine-1-carboxylic acid butyl ester:

This compound was prepared using a method analogous to that of Example 1, step 1.10, intermediate 10.1 replacing intermediate 1.9. The crude was purified by preparative LC-MS (I).

LC-MS (A): $t_R$=0.97 min; [M+H]$^+$: 602.95.

Example 11

4-{(S)-2-[(6-isopropylamino-2-phenyl-pyrimidine-4-carbonyl)-amino]-4-phosphono-butyryl}-piperazine-1-carboxylic acid butyl ester 11.1. 4-{(S)-4-(diethoxy-phosphoryl)-2-[(6-isopropylamino-2-phenyl-pyrimidine-4-carbonyl)-amino]-butyryl}-piperazine-1-carboxylic acid butyl ester:

This compound was prepared using a method analogous to that of Example 1, step 1.8, isopropylamine replacing intermediate 1.7 and intermediate 7.1 replacing 6-chloro-2-phenyl-pyrimidine-4-carboxylic acid. The product was however not purified.

LC-MS (A): $t_R$=1.08 min; [M+H]$^+$: 646.99.

11.2. 4-{(S)-2-[(6-isopropylamino-2-phenyl-pyrimidine-4-carbonyl)-amino]-4-phosphono-butyryl}-piperazine-1-carboxylic acid butyl ester:

This compound was prepared using a method analogous to that of Example 1, step 1.10, intermediate 11.1 replacing intermediate 1.9. The crude was purified by preparative LC-MS (I).

LC-MS (A): $t_R$=0.93 min; [M+H]$^+$: 591.05.

Example 12

4-{(S)-2-[(6-morpholin-4-yl-2-phenyl-pyrimidine-4-carbonyl)-amino]-4-phosphono-butyryl}-piperazine-1-carboxylic acid butyl ester 12.1. 4-{(S)-4-(diethoxy-phosphoryl)-2-[(6-morpholin-4-yl-2-phenyl-pyrimidine-4-carbonyl)-amino]-butyryl}-piperazine-1-carboxylic acid butyl ester:

This compound was prepared using a method analogous to that of Example 1 step 1.8, morpholine replacing intermediate 1.7 and intermediate 7.1 replacing 6-chloro-2-phenyl-pyrimidine-4-carboxylic acid. The compound was however not purified.

LC-MS (A): $t_R$=1.06 min; [M+H]$^+$: 674.96.

12.2. 4-{(S)-2-[(6-morpholin-4-yl-2-phenyl-pyrimidine-4-carbonyl)-amino]-4-phosphono-butyryl}-piperazine-1-carboxylic acid butyl ester:

This compound was prepared using a method analogous to that of Example 1, step 1.10, intermediate 12.1 replacing intermediate 1.9. The crude was purified by preparative LC-MS (I).

LC-MS (A): $t_R$=0.91 min; [M+H]$^+$: 618.89.

Example 13

4-((S)-2-{[6-(4-methyl-piperazin-1-yl)-2-phenyl-pyrimidine-4-carbonyl]-amino}-4-phosphono-butyryl)-piperazine-1-carboxylic acid butyl ester 13.1. 4-((S)-4-(diethoxy-phosphoryl)-2-{[6-(4-methyl-piperazin-1-yl)-2-phenyl-pyrimidine-4-carbonyl]-amino}-butyryl)-piperazine-1-carboxylic acid butyl ester:

This compound was prepared using a method analogous to that of Example 1 step 1.8, 1-methylpiperazine replacing intermediate 1.7 and intermediate 7.1 replacing 6-chloro-2-phenyl-pyrimidine-4-carboxylic acid. The compound was however not purified.

LC-MS (A): $t_R$=0.87 min; [M+H]$^+$: 688.04.

13.2. 4-((S)-2-{[6-(4-methyl-piperazin-1-yl)-2-phenyl-pyrimidine-4-carbonyl]-amino}-4-phosphono-butyryl)-piperazine-1-carboxylic acid butyl ester:

This compound was prepared using a method analogous to that of Example 1, step 1.10, intermediate 13.1 replacing intermediate 1.9. The crude was purified by preparative LC-MS (I).

LC-MS (A): $t_R$=0.77 min; [M+H]$^+$: 631.98.

Example 14

4-{(R)-2-[(6-methylamino-2-phenyl-pyrimidine-4-carbonyl)-amino]-3-phosphono-propionyl}-piperazine-1-carboxylic acid butyl ester 14.1. 4-[(R)-2-[(6-chloro-2-phenyl-pyrimidine-4-carbonyl)-amino]-3-(diethoxy-phosphoryl)-propionyl]-piperazine-1-carboxylic acid butyl ester:

This compound was prepared using a method analogous to that of Example 7, step 7.1, intermediate 2.4 replacing intermediate 5.2. The compound was however purified by CC (eluent: gradient from Hept to EA).

LC-MS (A): $t_R$=1.07 min; [M+H]$^+$: 609.88.

14.2. 4-{(R)-3-(diethoxy-phosphoryl)-2-[(6-methylamino-2-phenyl-pyrimidine-4-carbonyl)-amino]propionyl}-piperazine-1-carboxylic acid butyl ester:

Intermediate 14.1 (67 mg) was dissolved in a solution of methylamine in THF (2M, 0.55 mL). The reaction mixture was stirred at 50° C. overnight. It was quenched with sat. aq. NaHCO$_3$ and DCM and sat. aq. NaCl were added. The org. phase was dried (Na$_2$SO$_4$) and evaporated off to afford the desired product as a beige foam (47 mg).

LC-MS (A): $t_R$=1.01 min; [M+H]$^+$: 604.97.

14.3. 4-{(R)-2-[(6-methylamino-2-phenyl-pyrimidine-4-carbonyl)-amino]-3-phosphono-propionyl}-piperazine-1-carboxylic acid butyl ester:

This compound was prepared using a method analogous to that of Example 1 step 1.10, intermediate 14.2 replacing intermediate 1.9. The crude was however purified by CC (reverse phase; eluent: gradient from water/TFA 100/1 to MeCN/TFA 100/1).

LC-MS (A): $t_R$=0.83 min; [M+H]$^+$: 548.98.

Example 15

4-{(R)-2-[(6-dimethylamino-2-phenyl-pyrimidine-4-carbonyl)-amino]-3-phosphono-propionyl}-piperazine-1-carboxylic acid butyl ester 15.1. 4-{(R)-3-(diethoxy-phosphoryl)-2-[(6-dimethylamino-2-phenyl-pyrimidine-4-carbonyl)-amino]-propionyl}-piperazine-1-carboxylic acid butyl ester:

This compound was prepared using a method analogous to that of Example 14, step 14.2, dimethylamine (2M in THF) replacing methylamine (2M in THF).

LC-MS (A): $t_R$=1.05 min; [M+H]$^+$: 618.97.

15.2. 4-{(R)-2-[(6-dimethylamino-2-phenyl-pyrimidine-4-carbonyl)-amino]-3-phosphono-propionyl}-piperazine-1-carboxylic acid butyl ester:

This compound was prepared using a method analogous to that of Example 1, step 1.10, intermediate 15.1 replacing intermediate 1.9. The crude was purified by CC (reverse phase; eluent: gradient from water/TFA 100/1 to MeCN/TFA 100/1).

LC-MS (A): $t_R$=0.86 min; [M+H]$^+$: 562.94.

Example 16

4-{(R)-2-[(6-ethylamino-2-phenyl-pyrimidine-4-carbonyl)-amino]-3-phosphono-propionyl}-piperazine-1-carboxylic acid butyl ester 16.1. 4-{(R)-3-(diethoxy-phosphoryl)-2-[(6-ethylamino-2-phenyl-pyrimidine-4-carbonyl)-amino]-propionyl}-piperazine-1-carboxylic acid butyl ester:

This compound was prepared using a method analogous to that of Example 14, step 14.2, ethylamine (2M in THF) replacing methylamine (2M in THF).

LC-MS (A): $t_R$=1.04 min; [M+H]$^+$: 618.96.

16.2. 4-{(R)-2-[(6-ethylamino-2-phenyl-pyrimidine-4-carbonyl)-amino]-3-phosphono-propionyl}-piperazine-1-carboxylic acid butyl ester:

This compound was prepared using a method analogous to that of Example 1, step 1.10, intermediate 16.1 replacing intermediate 1.9. The crude was purified by CC (reverse phase; eluent: gradient from water/TFA 100/1 to MeCN/TFA 100/1).

LC-MS (A): $t_R$=0.87 min; [M+H]$^+$: 562.80.

Example 17

4-{(R)-2-[(6-isopropylamino-2-phenyl-pyrimidine-4-carbonyl)-amino]-3-phosphono-propionyl}-piperazine-1-carboxylic acid butyl ester 17.1. 4-{(R)-3-(diethoxy-phosphoryl)-2-[(6-isopropylamino-2-phenyl-pyrimidine-4-carbonyl)-amino]-propionyl}-piperazine-1-carboxylic acid butyl ester:

This compound was prepared using a method analogous to that of Example 1, step 1.8, isopropylamine (10 equivalents) replacing intermediate 1.7 and intermediate 7.1 replacing 6-chloro-2-phenyl-pyrimidine-4-carboxylic acid, using no DIPEA and heating at 50° C. instead of 60° C. The compound was however not purified.

LC-MS (A): $t_R$=1.02 min; [M+H]$^+$: 633.25.

17.2. 4-{(R)-2-[(6-isopropylamino-2-phenyl-pyrimidine-4-carbonyl)-amino]-3-phosphono-propionyl}-piperazine-1-carboxylic acid butyl ester:

This compound was prepared using a method analogous to that of Example 1 step 1.10, intermediate 17.1 replacing intermediate 1.9. The crude was purified by CC (reverse phase, eluent A: water/TFA 100/1; eluent B: MeCN/TFA 100/1; gradient: 5% B/1 CV; 5% to 70% B/20 CV; 70% B/4 CV).

LC-MS (A): $t_R$=0.90 min; [M+H]$^+$: 576.59.

Example 18

4-((S)-2-{[2-(4-fluoro-phenyl)-6-((S)-3-methoxy-pyrrolidin-1-yl)-pyrimidine-4-carbonyl]-amino}-4-phosphono-butyryl)-piperazine-1-carboxylic acid butyl ester 18.1. 4-fluoro-benzamidine:

To an ice-cold solution of hexamethyldisilazane (7 mL) in Et$_2$O (40 mL) was added n-BuLi (1.6M in hexanes, 20.6 mL), followed by a solution of 4-fluorobenzonitrile (2 g) in Et$_2$O (10 ml). After stirring at 0° C. for 10 min, the mixture was allowed to warm to RT and was stirred at RT for 20 h. The mixture was acidified to pH 1 by adding a 1M HCl solution and was washed with CHCl$_3$. The aq. layer was then basified to pH 14 by adding Na$_2$CO$_3$ and NaOH and was extracted twice with CHCl₃. The org. layers were dried (Na₂SO₄) and evaporated off to afford the desired compound (1.59 g).

LC-MS (A): $t_R$=0.33 min; [M+H]⁺: 139.21.

18.2. 6-chloro-2-(4-fluoro-phenyl)-pyrimidine-4-carboxylic acid:

This compound was prepared in 4 steps from intermediate 18.1 using methods analog to those described in WO 2006/114774 (see Example 1, step 1.3 and Example 24, steps 24.1, 24.2 and 24.3).

LC-MS (A): $t_R$=0.90 min; [M+H]⁺: 253.24.

18.3. 2-(4-fluoro-phenyl)-6-((S)-3-methoxy-pyrrolidin-1-yl)-pyrimidine-4-carboxylic acid:

This compound was prepared using a method analogous to that of Example 1, step 1.8, intermediate 18.2 replacing 6-chloro-2-phenyl-pyrimidine-4-carboxylic acid. The product was however not purified.

LC-MS (A): $t_R$=0.77 min; [M+H]⁺: 318.16.

18.4. 4-((S)-4-(diethoxy-phosphoryl)-2-{[2-(4-fluoro-phenyl)-6-((S)-3-methoxy-pyrrolidin-1-yl)-pyrimidine-4-carbonyl]-amino}-butyryl)-piperazine-1-carboxylic acid butyl ester:

This compound was prepared using a method analogous to that of Example 7, step 7.1, intermediate 18.3 replacing 6-chloro-2-phenyl-pyrimidine-4-carboxylic acid. The compound was however purified by preparative LC-MS (IV).

LC-MS (A): $t_R$=1.08 min; [M+H]⁺: 706.95.

18.5. 4-((S)-2-{[2-(4-fluoro-phenyl)-6-((S)-3-methoxy-pyrrolidin-1-yl)-pyrimidine-4-carbonyl]-amino}-4-phosphono-butyryl)-piperazine-1-carboxylic acid butyl ester:

This compound was prepared using a method analogous to that of Example 1, step 1.10, intermediate 18.4 replacing intermediate 1.9. The crude was purified by preparative LC-MS (II).

LC-MS (A): $t_R$=0.94 min; [M+H]⁺: 650.94.

Example 19

4-((S)-2-{[6-((S)-3-methoxy-pyrrolidin-1-yl)-2-p-tolyl-pyrimidine-4-carbonyl]amino}-4-phosphono-butyryl)-piperazine-1-carboxylic acid butyl ester 19.1. 6-chloro-2-p-tolyl-pyrimidine-4-carboxylic acid:

This compound was prepared in 4 steps from 4-methyl-benzamidine using methods analog to those described in WO 2006/114774 (see Example 1, step 1.3, Example 24, steps 24.1, 24.2 and 24.3).

LC-MS (A): $t_R$=0.93 min; [M+H]⁺: 249.28.

19.2. 6-((S)-3-methoxy-pyrrolidin-1-yl)-2-p-tolyl-pyrimidine-4-carboxylic acid:

This compound was prepared using a method analogous to that of Example 1, step 1.8, intermediate 19.1 replacing 6-chloro-2-phenyl-pyrimidine-4-carboxylic acid. The product was however not purified.

LC-MS (A): $t_R$=0.79 min; [M+H]⁺: 314.08.

19.3. 4-((S)-4-(diethoxy-phosphoryl)-2-{[6-((S)-3-methoxy-pyrrolidin-1-yl)-2-p-tolyl-pyrimidine-4-carbonyl]-amino}-butyryl)-piperazine-1-carboxylic acid butyl ester:

This compound was prepared using a method analogous to that of Example 7, step 7.1, intermediate 19.2 replacing 6-chloro-2-phenyl-pyrimidine-4-carboxylic acid. The product was however purified by preparative LC-MS (IV).

LC-MS (A): $t_R$=1.08 min; [M+H]⁺: 703.40.

19.4. 4-((S)-2-{[6-((S)-3-methoxy-pyrrolidin-1-yl)-2-p-tolyl-pyrimidine-4-carbonyl]-amino}-4-phosphono-butyryl)-piperazine-1-carboxylic acid butyl ester:

This compound was prepared using a method analogous to that of Example 1, step 1.10, intermediate 19.3 replacing intermediate 1.9. The crude was purified by preparative LC-MS (II).

LC-MS (A): $t_R$=0.93 min; [M+H]⁺: 646.90.

Example 20

4-((S)-2-{[2-(2-fluoro-phenyl)-6-((S)-3-methoxy-pyrrolidin-1-yl)-pyrimidine-4-carbonyl]-amino}-4-phosphono-butyryl)-piperazine-1-carboxylic acid butyl ester 20.1. 2-fluoro-benzamidine:

This compound was prepared using a method analogous to that of Example 18, step 18.1, 2-fluorobenzonitrile replacing 4-fluorobenzonitrile.

LC-MS (A): $t_R$=0.25 min; [M+H+MeCN]⁺: 180.35.

20.2. 6-chloro-2-(2-fluoro-phenyl)-pyrimidine-4-carboxylic acid:

This compound was prepared in 4 steps from intermediate 20.1 using methods analog to those described in WO 2006/114774 (see Example 1, step 1.3 and Example 24, steps 24.1, 24.2 and 24.3).

LC-MS (A): $t_R$=0.88 min; [M+H]⁺: 252.95.

20.3. 2-(4-fluoro-phenyl)-6-((S)-3-methoxy-pyrrolidin-1-yl)-pyrimidine-4-carboxylic acid:

This compound was prepared using a method analogous to that of Example 1, step 1.8, intermediate 20.2 replacing 6-chloro-2-phenyl-pyrimidine-4-carboxylic acid. The product was however not purified.

LC-MS (A): $t_R$=0.74 min; [M+H]⁺: 318.14.

20.4. 4-((S)-4-(diethoxy-phosphoryl)-2-{[2-(2-fluoro-phenyl)-6-((S)-3-methoxy-pyrrolidin-1-yl)-pyrimidine-4-carbonyl]-amino}-butyryl)-piperazine-1-carboxylic acid butyl ester:

This compound was prepared using a method analogous to that of Example 7, step 7.1, intermediate 20.3 replacing 6-chloro-2-phenyl-pyrimidine-4-carboxylic acid. The product was however purified by preparative LC-MS (IV).

LC-MS (A): $t_R$=1.05 min; [M+H]⁺: 706.95.

20.5. 4-((S)-2-{[2-(2-fluoro-phenyl)-6-((S)-3-methoxy-pyrrolidin-1-yl)-pyrimidine-4-carbonyl]-amino}-4-phosphono-butyryl)-piperazine-1-carboxylic acid butyl ester:

This compound was prepared using a method analogous to that of Example 1, step 1.10, intermediate 20.4 replacing intermediate 1.9. The crude was purified by preparative LC-MS (I).

LC-MS (A): $t_R$=0.89 min; [M+H]⁺: 650.98.

Example 21

4-((S)-2-{[2-(3-fluoro-phenyl)-6-((S)-3-methoxy-pyrrolidin-1-yl)-pyrimidine-4-carbonyl]-amino}-4-phosphono-butyryl)-piperazine-1-carboxylic acid butyl ester 21.1. 3-fluoro-benzamidine:

This compound was prepared using a method analogous to that of Example 18, step 18.1, 3-fluorobenzonitrile replacing 4-fluorobenzonitrile.

LC-MS (A): $t_R$=0.30 min; [M+H+MeCN]⁻: 180.35.

21.2. 6-chloro-2-(3-fluoro-phenyl)-pyrimidine-4-carboxylic acid:

This compound was prepared in 4 steps from intermediate 21.1 using methods analog to those described in WO 2006/114774 (see Example 1, step 1.3 and Example 24, steps 24.1, 24.2 and 24.3).

LC-MS (A): $t_R$=0.96 min; [M+H]⁺: 286.05.

21.3. 2-(3-fluoro-phenyl)-6-((S)-3-methoxy-pyrrolidin-1-yl)-pyrimidine-4-carboxylic acid:

This compound was prepared using a method analogous to that of Example 1, step 1.8, intermediate 21.2 replacing 6-chloro-2-phenyl-pyrimidine-4-carboxylic acid. The product was however not purified.

LC-MS (A): $t_R$=0.77 min; [M+H]$^+$: 318.16.

21.4. 4-((S)-4-(diethoxy-phosphoryl)-2-{[2-(3-fluoro-phenyl)-6-((S)-3-methoxy-pyrrolidin-1-yl)-pyrimidine-4-carbonyl]-amino}-butyryl)-piperazine-1-carboxylic acid butyl ester:

This compound was prepared using a method analogous to that of Example 7, step 7.1, intermediate 21.3 replacing 6-chloro-2-phenyl-pyrimidine-4-carboxylic acid. The product was however purified by preparative LC-MS (IV).

LC-MS (A): $t_R$=1.11 min; [M+H]$^+$: 706.94.

21.5. 4-((S)-2-{[2-(3-fluoro-phenyl)-6-((S)-3-methoxy-pyrrolidin-1-yl)-pyrimidine-4-carbonyl]-amino}-4-phosphono-butyryl)-piperazine-1-carboxylic acid butyl ester:

This compound was prepared using a method analogous to that of Example 1, step 1.10, intermediate 21.4 replacing intermediate 1.9. The crude was purified by preparative LC-MS (I).

LC-MS (A): $t_R$=0.89 min; [M+H]$^+$: 650.95.

Example 22

4-{(R)-2-[(6-methoxy-2-phenyl-pyrimidine-4-carbonyl)-amino]-3-phosphono-propionyl}-piperazine-1-carboxylic acid butyl ester 22.1. 4-{(R)-3-(diethoxy-phosphoryl)-2-[(6-methoxy-2-phenyl-pyrimidine-4-carbonyl)-amino]propionyl}-piperazine-1-carboxylic acid butyl ester:

NaH (36 mg, 55% dispersion in mineral oil) was suspended in MeOH (0.5 mL). The resulting sodium methylate solution was added to a solution of intermediate 14.1 (102 mg) in MeOH (0.5 mL). The reaction mixture was stirred at RT for 2 h. Sat. aq. NH$_4$Cl and DCM were added and the phases were separated. The aq. phase was extracted with DCM and the combined org. phases were dried (Na$_2$SO$_4$) and evaporated off to afford the desired compound (71 mg).

LC-MS (A): $t_R$=1.06 min; [M+H]$^+$: 605.97.

22.2. 4-{(R)-2-[(6-methoxy-2-phenyl-pyrimidine-4-carbonyl)-amino]-3-phosphono-propionyl}-piperazine-1-carboxylic acid butyl ester:

This compound was prepared using a method analogous to that of Example 1, step 1.10, intermediate 22.1 replacing intermediate 1.9. The crude was purified by CC (reversed phase; eluent: gradient from water/TFA 100/1 to MeCN/TFA 100/1).

LC-MS (A): $t_R$=0.90 min; [M+H]$^+$: 549.94.

Example 23

4-{(R)-2-[(6-methyl-2-phenyl-pyrimidine-4-carbonyl)-amino]-3-phosphono-propionyl}-piperazine-1-carboxylic acid butyl ester 23.1. 4-{(R)-3-(diethoxy-phosphoryl)-2-[(6-methyl-2-phenyl-pyrimidine-4-carbonyl)-amino]-propionyl}-piperazine-1-carboxylic acid butyl ester:

Intermediate 14.1 (114 mg), methylboronic acid (17 mg), tetrakis(triphenylphosphine)palladium (11 mg) and potassium phosphate (80 mg) were suspended in anhydrous dioxane (1 ml) under argon. The mixture was stirred overnight at RT under argon, then overnight at 50° C. Methylboronic acid (45 mg), tetrakis(triphenylphosphine)palladium (108 mg) and potassium phosphate (198 mg) were added to the mixture and it was further stirred for 4.5 h at 50° C. Water and DCM were added, the aq. phase was extracted with DCM and the combined org. phases were dried (Na$_2$SO$_4$) and evaporated off. The crude was purified by CC three times (CC No. 1: eluent: gradient from EA to EA/MeOH 9/1; CC No. 2: eluent: gradient form EA to EA/MeOH 100/1; CC No. 3: reverse phase, eluent: gradient from water/TFA 100/1 to MeCN/TFA 100/1) to give the desired compound as a colourless resin (22 mg).

LC-MS (A): $t_R$=1.03 min; [M+H]$^+$: 589.95.

23.2. 4-{(R)-2-[(6-methyl-2-phenyl-pyrimidine-4-carbonyl)-amino]-3-phosphono-propionyl}-piperazine-1-carboxylic acid butyl ester:

This compound was prepared using a method analogous to that of Example 1, step 1.10, intermediate 23.1 replacing intermediate 1.9. The crude was purified by CC (reversed phase; eluent: gradient from water/TFA 100/1 to MeCN/TFA 100/1).

LC-MS (A): $t_R$=0.86 min; [M+H]$^+$: 533.96.

Example 24

4-{(R)-2-[(6-cyclopropylamino-2-phenyl-pyrimidine-4-carbonyl)-amino]-3-phosphono-propionyl}-piperazine-1-carboxylic acid butyl ester 24.1. 4-[(R)-2-[(6-cyclopropylamino-2-phenyl-pyrimidine-4-carbonyl)-amino]-3-(diethoxy-phosphoryl)-propionyl]-piperazine-1-carboxylic acid butyl ester:

This compound was prepared using a method analogous to that of Example 1, step 1.8, cyclopropylamine replacing intermediate 1.7, intermediate 14.1 replacing 6-chloro-2-phenyl-pyrimidine-4-carboxylic acid and heating at 70° C. instead of 60° C. The product was however not purified.

LC-MS (A): $t_R$=1.04 min; [M+H]$^+$: 631.04.

24.2. 4-{(R)-2-[(6-cyclopropylamino-2-phenyl-pyrimidine-4-carbonyl)-amino]-3-phosphono-propionyl}-piperazine-1-carboxylic acid butyl ester:

This compound was prepared using a method analogous to that of Example 1, step 1.10, intermediate 24.1 replacing intermediate 1.9. The crude was purified by preparative LC-MS (II).

LC-MS (A): $t_R$=0.88 min; [M+H]$^+$: 574.84.

Example 25

4-{(R)-2-[(2-phenyl-6-phenylamino-pyrimidine-4-carbonyl)-amino]-3-phosphono-propionyl}-piperazine-1-carboxylic acid butyl ester 25.1. 4-{(R)-3-(diethoxy-phosphoryl)-2-[(2-phenyl-6-phenylamino-pyrimidine-4-carbonyl)-amino]propionyl}-piperazine-1-carboxylic acid butyl ester:

This compound was prepared using a method analogous to that of Example 1, step 1.8, aniline (10 equivalents) replacing intermediate 1.7, intermediate 14.1 replacing 6-chloro-2-phenyl-pyrimidine-4-carboxylic acid and heating at 70° C. instead of 60° C. The product was however not purified.

LC-MS (A): $t_R$=1.09 min; [M+H]$^+$: 666.99.

25.2. 4-{(R)-2-[(2-phenyl-6-phenylamino-pyrimidine-4-carbonyl)-amino]-3-phosphono-propionyl}-piperazine-1-carboxylic acid butyl ester:

This compound was prepared using a method analogous to that of Example 1, step 1.10, intermediate 25.1 replacing intermediate 1.9. The crude was purified by preparative LC-MS (III).

LC-MS (A): $t_R$=0.96 min; [M+H]$^+$: 610.88.

Example 26

4-{(R)-2-[(6-benzylamino-2-phenyl-pyrimidine-4-carbonyl)-amino]-3-phosphono-propionyl}-piperazine-1-carboxylic acid butyl ester 26.1. 4-[(R)-2-[(6-benzylamino-2-phenyl-pyrimidine-4-carbonyl)-amino]-3-(diethoxy-phosphoryl)-propionyl]-piperazine-1-carboxylic acid butyl ester:

This compound was prepared using a method analogous to that of Example 1, step 1.8, benzylamine replacing intermediate 1.7, intermediate 14.1 replacing 6-chloro-2-phenyl-pyrimidine-4-carboxylic acid and heating at 70° C. instead of 60° C. The product was however not purified.

LC-MS (A): $t_R$=1.09 min; $[M+H]^+$: 681.01.

26.2. 4-{(R)-2-[(6-benzylamino-2-phenyl-pyrimidine-4-carbonyl)-amino]-3-phosphono-propionyl}-piperazine-1-carboxylic acid butyl ester:

This compound was prepared using a method analogous to that of Example 1, step 1.10, intermediate 26.1 replacing intermediate 1.9. The crude was purified by preparative LC-MS (III).

LC-MS (A): $t_R$=0.95 min; $[M+H]^+$: 624.94.

Example 27

4-[(R)-2-({2-phenyl-6-[(R)-(tetrahydro-furan-3-yl)amino]-pyrimidine-4-carbonyl}-amino)-3-phosphono-propionyl]-piperazine-1-carboxylic acid butyl ester 27.1. 4-[(R)-3-(diethoxy-phosphoryl)-2-({2-phenyl-6-[(R)-(tetrahydro-furan-3-yl)amino]-pyrimidine-4-carbonyl}-amino)-propionyl]-piperazine-1-carboxylic acid butyl ester:

This compound was prepared using a method analogous to that of Example 1, step 1.8, (R)-(+)-3-aminotetrahydrofurane toluene-4-sulfonate replacing intermediate 1.7, intermediate 14.1 replacing 6-chloro-2-phenyl-pyrimidine-4-carboxylic acid and heating at 70° C. instead of 60° C. The product was however not purified.

LC-MS (A): $t_R$=1.01 min; $[M+H]^+$: 661.01.

27.2. 4-[(R)-2-({2-phenyl-6-[(R)-(tetrahydro-furan-3-yl)amino]-pyrimidine-4-carbonyl}-amino)-3-phosphono-propionyl]-piperazine-1-carboxylic acid butyl ester:

This compound was prepared using a method analogous to that of Example 1, step 1.10, intermediate 27.1 replacing intermediate 1.9. The crude was purified by preparative LC-MS (II).

LC-MS (A): $t_R$=0.86 min; $[M+H]^+$: 604.95.

Example 28

4-((R)-2-{[6-(3-hydroxy-pyrrolidin-1-yl)-2-phenyl-pyrimidine-4-carbonyl]-amino}-3-phosphono-propionyl)-piperazine-1-carboxylic acid butyl ester 28.1. 4-((R)-3-(diethoxy-phosphoryl)-2-{[6-(3-hydroxy-pyrrolidin-1-yl)-2-phenyl-pyrimidine-4-carbonyl]-amino}-propionyl)-piperazine-1-carboxylic acid butyl ester:

This compound was prepared using a method analogous to that of Example 1 step 1.8, 3-pyrrolidinol replacing intermediate 1.7, intermediate 14.1 replacing 6-chloro-2-phenyl-pyrimidine-4-carboxylic acid, and heating at 70° C. instead of 60° C. The product was however not purified.

LC-MS (A): $t_R$=0.97 min; $[M+H]^+$: 661.01.

28.2. 4-((R)-2-{[6-(3-hydroxy-pyrrolidin-1-yl)-2-phenyl-pyrimidine-4-carbonyl]-amino}-3-phosphono-propionyl)-piperazine-1-carboxylic acid butyl ester:

This compound was prepared using a method analogous to that of Example 1, step 1.10, intermediate 28.1 replacing intermediate 1.9. The crude was purified by preparative LC-MS (I).

LC-MS (A): $t_R$=0.81 min; $[M+H]^+$: 604.93.

Example 29

4-[(R)-2-({6-[(2-methoxy-ethyl)-methyl-amino]-2-phenyl-pyrimidine-4-carbonyl}-amino)-3-phosphono-propionyl]-piperazine-1-carboxylic acid butyl ester 29.1. 4-[(R)-3-(diethoxy-phosphoryl)-2-({6-[(2-methoxy-ethyl)-methyl-amino]-2-phenyl-pyrimidine-4-carbonyl}-amino)-propionyl]-piperazine-1-carboxylic acid butyl ester:

This compound was prepared using a method analogous to that of Example 1, step 1.8, N-(2-methoxyethyl)methylamine replacing intermediate 1.7, intermediate 14.1 replacing 6-chloro-2-phenyl-pyrimidine-4-carboxylic acid and heating at 70° C. instead of 60° C. The product was however not purified.

LC-MS (A): $t_R$=1.05 min; $[M+H]^+$: 663.01.

29.2. 4-[(R)-2-({6-[(2-methoxy-ethyl)-methyl-amino]-2-phenyl-pyrimidine-4-carbonyl}-amino)-3-phosphono-propionyl]-piperazine-1-carboxylic acid butyl ester:

This compound was prepared using a method analogous to that of Example 1, step 1.10, intermediate 29.1 replacing intermediate 1.9. The crude was purified by preparative LC-MS (II).

LC-MS (A): $t_R$=0.89 min; $[M+H]^+$: 606.81.

Example 30

4-((R)-2-{[6-(2-ethoxycarbonyl-ethylamino)-2-phenyl-pyrimidine-4-carbonyl]-amino}-3-phosphono-propionyl)-piperazine-1-carboxylic acid butyl ester 30.1. 4-((R)-3-(diethoxy-phosphoryl)-2-{[6-(2-ethoxycarbonyl-ethylamino)-2-phenyl-pyrimidine-4-carbonyl]-amino}-propionyl)-piperazine-1-carboxylic acid butyl ester:

This compound was prepared using a method analogous to that of Example 1, step 1.8, ethyl 3-aminopropanoate hydrochloride replacing intermediate 1.7, intermediate 14.1 replacing 6-chloro-2-phenyl-pyrimidine-4-carboxylic acid and heating at 70° C. instead of 60° C. The product was however not purified.

LC-MS (A): $t_R$=1.04 min; $[M+H]^+$: 690.97.

30.2. 4-((R)-2-{[6-(2-ethoxycarbonyl-ethylamino)-2-phenyl-pyrimidine-4-carbonyl]-amino}-3-phosphono-propionyl)-piperazine-1-carboxylic acid butyl ester:

This compound was prepared using a method analogous to that of Example 1, step 1.10, intermediate 30.1 replacing intermediate 1.9. The crude was purified by preparative LC-MS (II).

LC-MS (A): $t_R$=0.90 min; $[M+H]^+$: 634.91.

Example 31

4-((R)-2-{[6-(2-carboxy-ethylamino)-2-phenyl-pyrimidine-4-carbonyl]-amino}-3-phosphono-propionyl)-piperazine-1-carboxylic acid butyl ester The compound of Example 30 (42 mg) and NaOH (26 mg) were dissolved in MeOH (1 mL). After stirring at RT for 2 h, the reaction mixture was acidified with a 1M HCl solution and extracted with EA. The org. layers were dried ($Na_2SO_4$) and evaporated off. The crude was purified by preparative LC-MS (I) to afford the desired compound (0.2 mg).

LC-MS (A): $t_R$=0.80 min; $[M+H]^+$: 606.80.

Example 32

4-{(R)-2-[(2,6-diphenyl-pyrimidine-4-carbonyl)-amino]-3-phosphono-propionyl}-piperazine-1-carboxylic acid butyl ester 32.1. 4-{(R)-3-(diethoxy-phosphoryl)-2-[(2,6-diphenyl-pyrimidine-4-carbonyl)-amino]-propionyl}-piperazine-1-carboxylic acid butyl ester:

Intermediate 14.1 (150 mg), phenylboronic acid (45 mg), tetrakis(triphenylphosphine)palladium (14 mg) and potassium phosphate (104 mg) were dissolved in anhydrous dioxane (1 ml) under argon. The mixture was heated at 80° C. overnight and water was added. The mixture was extracted with EA and the org. phase was dried ($Na_2SO_4$) and evaporated off. The crude was purified by CC (eluent: gradient from Hept to EA, followed by MeOH) to give the desired compound (86 mg).

LC-MS (A): $t_R$=1.12 min; $[M+H]^+$: 651.99.

32.2. 4-{(R)-2-[(2,6-diphenyl-pyrimidine-4-carbonyl)-amino]-3-phosphono-propionyl}-piperazine-1-carboxylic acid butyl ester:

Intermediate 32.1 (86 mg) was dissolved in 3 M HCl in EA (1.5 mL) and $H_2O$ (0.15 mL). After stirring at RT for 2 h, toluene was added and the solvents were evaporated off. The crude was purified by preparative LC-MS (III) to give the desired compound as a white solid (34 mg).

LC-MS (A): $t_R$=0.98 min; $[M+H]^+$: 595.90.

Example 33

4-{(R)-2-[(2-phenyl-6-thiophen-3-yl-pyrimidine-4-carbonyl)-amino]-3-phosphono-propionyl}-piperazine-1-carboxylic acid butyl ester 33.1. 2-phenyl-6-thiophen-3-yl-pyrimidine-4-carboxylic acid:

This compound was prepared using a method analogous to that of Example 32, step 32.1, 6-chloro-2-phenyl-pyrimidine-4-carboxylic acid replacing intermediate 14.1 and thiophene-3-boronic acid replacing phenylboronic acid. The crude was however crystallized (EtOH/$H_2O$ 2/1). LC-MS (A): $t_R$=1.03 min; $[M+H]^+$: 283.03.

33.2. 4-{(R)-3-(diethoxy-phosphoryl)-2-[(2-phenyl-6-thiophen-3-yl-pyrimidine-4-carbonyl)-amino]-propionyl}-piperazine-1-carboxylic acid butyl ester:

This compound was prepared using a method analogous to that of Example 1, step 1.3, intermediate 33.1 replacing intermediate 1.2 and intermediate 2.4 replacing 1-ethoxycarbonylpiperazine. During the work-up, the org. phases were additionally washed with an aq. $NaHSO_4$ solution. The crude was not purified.

LC-MS (A): $t_R$=1.11 min; $[M+H]^+$: 657.93.

33.3. 4-{(R)-2-[(2-phenyl-6-thiophen-3-yl-pyrimidine-4-carbonyl)-amino]-3-phosphono-propionyl}-piperazine-1-carboxylic acid butyl ester:

This compound was prepared using a method analogous to that of Example 32, step 32.2, intermediate 33.2 replacing intermediate 32.1. The product was however purified by preparative LC-MS (V) using a X-Terra® column.

LC-MS (A): $t_R$=0.97 min; $[M+H]^+$: 601.87.

Example 34

4-((R)-2-{[6-(4-methoxy-phenyl)-2-phenyl-pyrimidine-4-carbonyl]-amino}-3-phosphono-propionyl)-piperazine-1-carboxylic acid butyl ester 34.1. 6-(4-methoxy-phenyl)-2-phenyl-pyrimidine-4-carboxylic acid:

This compound was prepared using a method analogous to that of Example 33, step 33.1, 4-methoxyphenylboronic acid replacing thiophene-3-boronic acid.

LC-MS (A): $t_R$=1.04 min; $[M+H]^+$: 307.04.

34.2. 4-((R)-3-(diethoxy-phosphoryl)-2-{[6-(4-methoxy-phenyl)-2-phenyl-pyrimidine-4-carbonyl]-amino}-propionyl)-piperazine-1-carboxylic acid butyl ester:

This compound was prepared using a method analogous to that of Example 33, step 33.2, intermediate 34.1 replacing intermediate 33.1.

LC-MS (A): $t_R$=1.13 min; $[M+H]^+$: 681.96.

34.3. 4-((R)-2-{[6-(4-methoxy-phenyl)-2-phenyl-pyrimidine-4-carbonyl]-amino}-3-phosphono-propionyl)-piperazine-1-carboxylic acid butyl ester:

This compound was prepared using a method analogous to that of Example 32, step 32.2, intermediate 34.2 replacing intermediate 32.1. The product was however purified by preparative LC-MS (V) using a X-Terra® column.

LC-MS (A): $t_R$=0.99 min; $[M+H]^+$: 625.92.

Example 35

4-{(R)-2-[(6-cyclopropyl-2-phenyl-pyrimidine-4-carbonyl)-amino]-3-phosphono-propionyl}-piperazine-1-carboxylic acid butyl ester 35.1. 6-cyclopropyl-2-phenyl-pyrimidine-4-carboxylic acid:

This compound was prepared using a method analogous to that of Example 33, step 33.1, cyclopropylboronic acid replacing thiophene-3-boronic acid.

LC-MS (A): $t_R$=0.98 min; $[M+H]^+$: 241.10.

35.2. 4-[(R)-2-[(6-cyclopropyl-2-phenyl-pyrimidine-4-carbonyl)-amino]-3-(diethoxy-phosphoryl)-propionyl]-piperazine-1-carboxylic acid butyl ester:

This compound was prepared using a method analogous to that of Example 33, step 33.2, intermediate 35.1 replacing intermediate 33.1.

LC-MS (A): $t_R$=1.09 min; $[M+H]^+$: 615.98.

35.3. 4-{(R)-2-[(6-cyclopropyl-2-phenyl-pyrimidine-4-carbonyl)-amino]-3-phosphono-propionyl}-piperazine-1-carboxylic acid butyl ester:

This compound was prepared using a method analogous to that of Example 32, step 32.2, intermediate 35.2 replacing intermediate 32.1. The product was however purified by preparative LC-MS (V) using a X-Terra® column LC-MS (A): $t_R$=0.94 min; $[M+H]^+$: 559.95.

Example 36

4-{(R)-2-[(6-butyl-2-phenyl-pyrimidine-4-carbonyl)-amino]-3-phosphono-propionyl}-piperazine-1-carboxylic acid butyl ester 36.1. 6-butyl-2-phenyl-pyrimidine-4-carboxylic acid:

This compound was prepared using a method analogous to that of Example 33, step 33.1, butylboronic acid replacing thiophene-3-boronic acid.

LC-MS (A): $t_R$=1.04 min; $[M+H]^+$: 257.10.

36.2. 4-[(R)-2-[(6-butyl-2-phenyl-pyrimidine-4-carbonyl)-amino]-3-(diethoxy-phosphoryl)-propionyl]-piperazine-1-carboxylic acid butyl ester:

This compound was prepared using a method analogous to that of Example 33, step 33.2, intermediate 36.1 replacing intermediate 33.1. LC-MS (A): $t_R$=1.12 min; [M+H]$^+$: 632.03.

36.3. 4-{(R)-2-[(6-butyl-2-phenyl-pyrimidine-4-carbonyl)-amino]-3-phosphono-propionyl}-piperazine-1-carboxylic acid butyl ester:

This compound was prepared using a method analogous to that of Example 32, step 32.2, intermediate 36.2 replacing intermediate 32.1. The product was however purified by preparative LC-MS (V) using a X-Terra® column LC-MS (A): $t_R$=0.98 min; [M+H]$^+$: 576.58.

Example 37

4-[(R)-2-({2-phenyl-6-[(S)-(tetrahydro-furan-3-yl)oxy]-pyrimidine-4-carbonyl}-amino)-3-phosphono-propionyl]-piperazine-1-carboxylic acid butyl ester 37.1. 4-[(R)-3-(diethoxy-phosphoryl)-2-({2-phenyl-6-[(S)-(tetrahydro-furan-3-yl)oxy]-pyrimidine-4-carbonyl}-amino)-propionyl]-piperazine-1-carboxylic acid butyl ester:

(S)-(+)-hydroxytetrahydrofurane (108 mg) was added to a suspension of NaH (60% dispersion in mineral oil, 49 mg) in DMF (0.5 mL). The suspension was stirred at RT for 15 min and was added to a solution of intermediate 14.1 (150 mg) in DMF (0.25 mL). The reaction mixture was stirred at RT for 4 h. and DCM were added, the phases were separated and the org. phase was further extracted with DCM. The combined org. phases were washed with a solution of aq. NH$_4$Cl, dried (Na$_2$SO$_4$) and evaporated off. CC of the crude (eluent: gradient from EA to EA/MeOH 100/1) afforded the desired compound (53 mg).

LC-MS (A): $t_R$=1.05 min; [M+H]$^+$: 661.99.

37.2. 4-[(R)-2-({2-phenyl-6-[(S)-(tetrahydro-furan-3-yl)oxy]-pyrimidine-4carbonyl}-amino)-3-phosphono-propionyl]-piperazine-1-carboxylic acid butyl ester:

This compound was prepared using a method analogous to that of Example 1, step 1.10, intermediate 37.1 replacing intermediate 1.9.

LC-MS (A): $t_R$=0.90 min; [M+H]$^+$: 605.95.

Example 38

4-((R)-2-{[6-((S)-3-methoxy-pyrrolidin-1-yl)-2-phenyl-pyrimidine-4-carbonyl]-amino}-3-phosphono-propionyl)-2-methyl-piperazine-1-carboxylic acid ethyl ester 38.1. 4-[(R)-2-tert-butoxycarbonylamino-3-(diethoxy-phosphoryl)-propionyl]-2-methyl-piperazine-1-carboxylic acid ethyl ester:

This compound was prepared using a method analogous to that of Example 1, step 1.3, 2-methyl-piperazine-1-carboxylic acid ethyl ester (prepared as described in WO 2006/114774, Example 46, intermediate 46.3) replacing 1-ethoxycarbonylpiperazine.

LC-MS (A): $t_R$=0.90 min; [M+H]$^+$: 479.68.

38.2. 4-[(R)-2-amino-3-(diethoxy-phosphoryl)-propionyl]-2-methyl-piperazine-1-carboxylic acid ethyl ester:

To a solution of intermediate 38.1 (160 mg) in DCM (4 mL) was added TFA (1 mL). The reaction mixture was stirred overnight at RT, was diluted with toluene and evaporated off. The crude was taken up in DCM, washed with aq. NaHCO$_3$, dried (Na$_2$SO$_4$) and evaporated off to afford 67 mg of the desired product as yellow oil.

LC-MS (A): $t_R$=0.68 min; [M+H]$^+$: 380.06.

38.3. 4-((R)-3-(diethoxy-phosphoryl)-2-{[6-((S)-3-methoxy-pyrrolidin-1-yl)-2-phenyl-pyrimidine-4-carbonyl]-amino}-propionyl)-2-methyl-piperazine-1-carboxylic acid ethyl ester:

This compound was prepared using a method analogous to that of Example 1, step 1.9, intermediate 38.2 replacing intermediate 1.4 and using DCM instead of DCM/THF.

LC-MS (A): $t_R$=1.01 min; [M+H]$^+$: 661.02.

38.4. 4-((R)-2-{[6-((S)-3-methoxy-pyrrolidin-1-yl)-2-phenyl-pyrimidine-4 carbonyl]-amino}-3-phosphono-propionyl)-2-methyl-piperazine-1-carboxylic acid ethyl ester:

This compound was prepared using a method analogous to that of Example 32, step 32.2, intermediate 38.3 replacing intermediate 32.1 and using 4 M HCl in dioxane instead of 3 M HCl in EA.

LC-MS (A): $t_R$=0.83 min; [M+H]$^+$: 604.99.

Example 39

4-((R)-2-{[6-((S)-3-methoxy-pyrrolidin-1-yl)-2-phenyl-pyrimidine-4-carbonyl]-amino}-4-phosphono-butyryl)-piperazine-1-carboxylic acid ethyl ester 39.1. (R)-2-benzyloxycarbonylamino-4-hydroxy-butyric acid:

This compound was prepared using a method analogous to that of Example 4, step 4.1, H-D-Hse-OH replacing H-Hse-OH.

LC-MS (A): $t_R$=0.71 min; [M+H]$^+$: 254.37.

39.2. (R)-2-benzyloxycarbonylamino-4-hydroxy-butyric acid dicyclohexylamine salt:

This compound was prepared using a method analogous to that of Example 4, step 4.2, intermediate 39.1 replacing intermediate 4.1.

LC-MS (A): $t_R$=0.66 min; [M+H]$^+$: 254.07.

39.3. (R)-2-benzyloxycarbonylamino-4-hydroxy-butyric acid methyl ester:

This compound was prepared using a method analogous to that of Example 4, step 4.3, intermediate 39.2 replacing intermediate 4.2.

LC-MS (A): $t_R$=0.79 min; [M+H]$^+$: 268.12.

39.4. (R)-2-benzyloxycarbonylamino-4-bromo-butyric acid methyl ester:

This compound was prepared using a method analogous to that of Example 4, step 4.4, intermediate 39.3 replacing intermediate 4.3.

LC-MS (A): $t_R$=0.99 min; [M+H]$^+$: 330.02.

39.5. (R)-2-benzyloxycarbonylamino-4-(diethoxy-phosphoryl)-butyric acid methyl ester:

This compound was prepared using a method analogous to that of Example 1, step 1.1, intermediate 39.4 replacing Boc-3-iodo-L-Ala-OMe. The compound was however purified by CC (EA/MeOH 9/1).

LC-MS (A): $t_R$=0.91 min; [M+H]$^+$: 387.93.

39.6. (R)-2-benzyloxycarbonylamino-4-(diethoxy-phosphoryl)-butyric acid:

This compound was prepared using a method analogous to that of Example 1, step 1.2, intermediate 39.5 replacing intermediate 1.1.

LC-MS (A): $t_R$=0.83 min; [M+H]$^+$: 374.07.

39.7. 4-[(R)-2-benzyloxycarbonylamino-4-(diethoxy-phosphoryl)-butyryl]-piperazine-1-carboxylic acid ethyl ester:

This compound was prepared using a method analogous to that of Example 1, step 1.9, intermediate 39.6 replacing intermediate 1.8 and 1-ethoxycarbonylpiperazine replacing intermediate 1.4. The compound was however purified twice by CC (EA/Hept. 0/1 to 1/0 followed by EA/EA/MeOH 9/1 1/0 to 0/1).

LC-MS (A): $t_R$=0.90 min; [M+H]$^+$: 514.00.

39.8. 4-[(R)-2-amino-4-(diethoxy-phosphoryl)-butyryl]-piperazine-1-carboxylic acid ethyl ester:

This compound was prepared using a method analogous to that of Example 2, step 2.2, intermediate 39.7 replacing intermediate 2.1.

LC-MS (A): $t_R$=0.65 min; [M+H]$^+$: 380.06.

39.9. 4-((R)-4-(diethoxy-phosphoryl)-2-{[6-((S)-3-methoxy-pyrrolidin-1-yl)-2-phenyl-pyrimidine-4-carbonyl]-amino}-butyryl)-piperazine-1-carboxylic acid ethyl ester:

This compound was prepared using a method analogous to that of Example 1, step 1.3, intermediate 39.8 replacing 1-ethoxycarbonylpiperazine and intermediate 1.8 replacing intermediate 1.2. The crude was however purified by CC (eluent: gradient from EA to EA/MeOH 9/1).

LC-MS (A): $t_R$=1.00 min; [M+H]$^+$: 661.00.

39.10. 4-((R)-2-{[6-((S)-3-methoxy-pyrrolidin-1-yl)-2-phenyl-pyrimidine-4-carbonyl]-amino}-4-phosphono-butyryl)-piperazine-1-carboxylic acid ethyl ester:

This compound was prepared using a method analogous to that of Example 1, step 1.10, intermediate 39.9 replacing intermediate 1.9.

LC-MS (A): $t_R$=0.85 min; [M+H]$^+$: 604.93.

Example 40

4-((R)-2-{[6-((S)-3-methoxy-pyrrolidin-1-yl)-2-phenyl-pyrimidine-4-carbonyl]-amino}-4-phosphono-butyryl)-piperazine-1-carboxylic acid butyl ester 40.1. 4-[(R)-2-benzyloxycarbonylamino-4-(diethoxy-phosphoryl)-butyryl]-piperazine-1-carboxylic acid butyl ester:

This compound was prepared using a method analogous to that of Example 39, step 39.7, intermediate 2.2 replacing 1-ethoxycarbonylpiperazine. The compound was however purified by CC (eluent: gradient from EA to EA/MeOH 95/5).

LC-MS (A): $t_R$=0.97 min; [M+H]$^+$: 542.02.

40.2. 4-[(R)-2-amino-4-(diethoxy-phosphoryl)-butyryl]-piperazine-1-carboxylic acid butyl ester:

This compound was prepared using a method analogous to that of Example 2, step 2.2, intermediate 40.1 replacing intermediate 2.1, however using MeOH instead of EtOH.

LC-MS (A): $t_R$=0.73 min; [M+H]$^+$: 408.04.

40.3. 4-((R)-4-(diethoxy-phosphoryl)-2-{[6-((S)-3-methoxy-pyrrolidin-1-yl)-2-phenyl-pyrimidine-4-carbonyl]-amino}-butyryl)-piperazine-1-carboxylic acid butyl ester:

This compound was prepared using a method analogous to that of Example 1, step 1.3, intermediate 40.2 replacing 1-ethoxycarbonylpiperazine and intermediate 1.8 replacing intermediate 1.2. The crude was however purified by CC (eluent: gradient from EA to EA/MeOH 9/1).

LC-MS (A): $t_R$=1.07 min; [M+H]$^+$: 689.03.

40.4. 4-((R)-2-{[6-((S)-3-methoxy-pyrrolidin-1-yl)-2-phenyl-pyrimidine-4-carbonyl]-amino}-4-phosphono-butyryl)-piperazine-1-carboxylic acid butyl ester:

This compound was prepared using a method analogous to that of Example 1 step 1.10, intermediate 40.3 replacing intermediate 1.9. No purification was performed.

LC-MS (A): $t_R$=0.94 min; [M+H]$^+$: 633.25.

Example 41

4-((R)-2-{[6-((1S,2S)-2-methoxymethyl-cyclopropyl)-2-phenyl-pyrimidine-4-carbonyl]-amino}-3-phosphono-propionyl)-piperazine-1-carboxylic acid butyl ester 41.1. (E)-3-tributylstannanyl-prop-2-en-1-ol:

To neat propargyl alcohol (1 mL) were added tributyltin hydride (5.8 mL) followed by 1,1'-azobis(cyclohexanecarbonitrile) (213 mg). The mixture was heated for 2 h at 80° C., cooled to RT and directly purified by CC (EA/Hept 4/96 to 5/95) to afford the desired compound (2.98 g).

$^1$H-NMR (CDCl$_3$): δ=6.2 (m, 2H); 4.15 (m, 2H); 1.55-1.25 (m, 18H); 0.90 (t, 9H).

41.2. ((1R,2S)-2-tributylstannanyl-cyclopropyl)-methanol:

To a solution of DME (1.8 mL) in anhydrous DCM (70 mL) cooled at −13° C. under argon was slowly added diethylzinc (18.5 mL), followed by diiodomethane (3 mL) in DCM (20 mL) over a 30 min period while keeping the internal temperature around −12.5° C. After completion of the addition, the resulting solution was stirred for 30 min at −10° C. A solution of (4R,5R)-2-butyl-N,N,N',N'-tetramethyl-1,3,2-dioxaborolane-4,5-dicarboxamide (3.2 g) in DCM (25 mL) was added slowly to keep internal temperature below −10° C., immediately followed by a solution of intermediate 41.1 in DCM (25 mL) dropwise (internal temperature between −10° C. and −8° C.). The cooling bath was removed, and the reaction mixture was allowed to warm to RT and was stirred overnight at RT. The reaction was quenched with an aq. NH$_4$Cl solution (10 mL), and a 1M aq. HCl solution (10 mL). The mixture was diluted with H$_2$O, the org. phase separated and the aq. phase was extracted with DCM and Et$_2$O. The combined org. phases were dried over MgSO$_4$ and evaporated off. CC (Hept/EA 100/0 to 95/5) gave the desired compound (3.18 g).

$^1$H-NMR (CDCl$_3$): δ=3.55 (m, 1H); 3.39 (m, 1H); 1.54-1.44 (m, 6H); 1.36-1.24 (m, 6H); 1.14-1.03 (m, 1H); 0.90 (t, 9H); 0.83-0.78 (m, 6H); 0.75-0.69 (m, 1H); 0.55-0.50 (m, 2H); −0.20-−0.30 (m, 1H).

Optical rotation (589 nm, CHCl$_3$, 26.6° C., l=10 cm, 99.6 mg in 10 mL, c=1.0): specific optical rotation=+14.74°.

41.3. Tributyl-((1S,2R)-2-methoxymethyl-cyclopropyl)-stannane:

To a solution of intermediate 41.2 (2.94 g) in THF (60 mL) was added NaH (977 mg, 60% in mineral oil) at RT, and the mixture stirred 30 min at RT. MeI (2.3 mL) was added and stirring was continued at RT overnight. The reaction mixture was diluted with H$_2$O and extracted with DCM. The combined org. phases were dried over MgSO$_4$ and evaporated off. CC (Hept/EA 100/0 to 95:5) gave the desired compound (3.13 g).

$^1$H-NMR (CDCl$_3$): δ=3.45 (dd, 1H); 3.38 (s, 3H); 3.12 (dd, 1H); 1.55-1.47 (m, 6H); 1.37-1.28 (m, 6H); 1.05 (m, 1H); 0.91 (t, 9H); 0.83 (t, 6H); 0.57 (m, 2H); −0.30 (m, 1H).

41.4. 4-((R)-3-(diethoxy-phosphoryl)-2-{[6-((1S,2S)-2-methoxymethyl-cyclopropyl)-2-phenyl-pyrimidine-4-carbonyl]-amino}-propionyl)-piperazine-1-carboxylic acid butyl ester:

A mixture of intermediate 14.1 (80 mg), intermediate 41.3 (54 mg), Pd(PPh$_3$)$_4$ (8 mg) in degassed toluene (2 ml) was heated at 130° C. in a sealed vial until reaction completion. The crude mixture was filtered over Celite, evaporated off and directly purified by preparative TLC (EA/MeOH 9/1) to afford 55 mg of impure desired compound.

LC-MS (A): $t_R$=1.07 min; [M+H]$^+$: 659.99.

41.5. 4-((R)-2-{[6-((1S,2S)-2-methoxymethyl-cyclopropyl)-2-phenyl-pyrimidine-4-carbonyl]-amino}-3-phosphono-propionyl)-piperazine-1-carboxylic acid butyl ester:

This compound was prepared using a method analogous to that of Example 38, step 38.4, intermediate 41.4 replacing intermediate 38.3. The compound was however purified by CC (reverse phase; eluent: H$_2$O/MeCN 95/5 to 10/90).

LC-MS (A): t$_R$=0.92 min; [M+H]$^+$: 603.94.

Example 42

4-((R)-2-{[6-((1S,2S)-2-hydroxymethyl-cyclopropyl)-2-phenyl-pyrimidine-4-carbonyl]-amino}-3-phosphono-propionyl)-piperazine-1-carboxylic acid butyl ester 42.1. 4-((R)-3-(diethoxy-phosphoryl)-2-{[6-((1S,2S)-2-hydroxymethyl-cyclopropyl)-2-phenyl-pyrimidine-4-carbonyl]-amino}-propionyl)-piperazine-1-carboxylic acid butyl ester:

This compound was prepared using a method analogous to that of Example 41, step 41.4, intermediate 41.2 replacing intermediate 41.3.

LC-MS (A): t$_R$=0.99 min; [M+H]$^+$: 645.98.

42.2. 4-((R)-2-{[6-((1S,2S)-2-hydroxymethyl-cyclopropyl)-2-phenyl-pyrimidine-4-carbonyl]-amino}-3-phosphono-propionyl)-piperazine-1-carboxylic acid butyl ester:

This compound was prepared using a method analogous to that of Example 38, step 38.4, intermediate 42.1 replacing intermediate 38.3. The compound was however purified by CC (reverse phase; eluent: H$_2$O/MeCN 95/5 to 10/90).

LC-MS (A): t$_R$=0.86 min; [M+H]$^+$: 589.93.

Example 43

4-((R)-2-{[6-(2-hydroxy-ethylamino)-2-phenyl-pyrimidine-4-carbonyl]-amino}-3-phosphono-propionyl)-piperazine-1-carboxylic acid butyl ester 43.1. 4-((R)-3-(diethoxy-phosphoryl)-2-{[6-(2-hydroxy-ethylamino)-2-phenyl-pyrimidine-4-carbonyl]-amino}-propionyl)-piperazine-1-carboxylic acid butyl ester:

This compound was prepared using a method analogous to that of Example 1, step 1.8, ethanolamine replacing intermediate 1.7 and intermediate 14.1 replacing 6-chloro-2-phenyl-pyrimidine-4-carboxylic acid.

LC-MS (A): t$_R$=0.94 min; [M+H]$^+$: 635.01.

43.2. 4-((R)-2-{[6-(2-hydroxy-ethylamino)-2-phenyl-pyrimidine-4-carbonyl]-amino}-3-phosphono-propionyl)-piperazine-1-carboxylic acid butyl ester:

This compound was prepared using a method analogous to that of Example 38, step 38.4, intermediate 43.1 replacing intermediate 38.3. The compound was however purified by CC (reverse phase; eluent: gradient from H$_2$O+0.1% TFA to MeCN+0.1% TFA).

LC-MS (A): t$_R$=0.79 min; [M+H]$^+$: 578.92.

Example 44

4-((R)-2-{[6-(2-hydroxymethyl-piperidin-1-yl)-2-phenyl-pyrimidine-4-carbonyl]-amino}-3-phosphono-propionyl)-piperazine-1-carboxylic acid butyl ester 44.1. 4-((R)-3-(diethoxy-phosphoryl)-2-{[6-(2-hydroxymethyl-piperidin-1-yl)-2-phenyl-pyrimidine-4-carbonyl]-amino}-propionyl)-piperazine-1-carboxylic acid butyl ester:

This compound was prepared using a method analogous to that of Example 1, step 1.8, 2-(hydroxymethyl)piperidine replacing intermediate 1.7 and intermediate 14.1 replacing 6-chloro-2-phenyl-pyrimidine-4-carboxylic acid.

LC-MS (A): t$_R$=1.02 min; [M+H]$^+$: 689.04.

44.2. 4-((R)-2-{[6-(2-hydroxymethyl-piperidin-1-yl)-2-phenyl-pyrimidine-4-carbonyl]-amino}-3-phosphono-propionyl)-piperazine-1-carboxylic acid butyl ester:

This compound was prepared using a method analogous to that of Example 38, step 38.4, intermediate 44.1 replacing intermediate 38.3. The compound was however purified by CC (reverse phase; eluent: gradient from H$_2$O+0.1% TFA to MeCN+0.1% TFA).

LC-MS (A): t$_R$=0.86 min; [M+H]$^+$: 632.94.

Example 45

4-((R)-2-{[6-(3-methoxy-propyl)-2-phenyl-pyrimidine-4-carbonyl]-amino}-3-phosphono-propionyl)-piperazine-1-carboxylic acid butyl ester 45.1. 4-((R)-3-(diethoxy-phosphoryl)-2-{[6-(3-methoxy-prop-1-ynyl)-2-phenyl-pyrimidine-4-carbonyl]-amino}-propionyl)-piperazine-1-carboxylic acid butyl ester:

NEt$_3$ (0.077 mL) and methylpropargylether (0.048 mL) in DMF (2.5 mL) were syringed into a flask containing copper iodide (5.1 mg), bis-(triphenylphosphine) palladium(II)-dichloride (12.5 mg) and intermediate 14.1 (305 mg) under argon. The mixture was allowed to stir at RT overnight. The solvent was removed and the crude was purified by CC (DCM/MeOH 99/1 to 90/10) to afford the desired compound (311 mg).

LC-MS (A): t$_R$=1.06 min; [M+H]$^+$: 644.19.

45.2. 4-((R)-3-(diethoxy-phosphoryl)-2-{[6-(3-methoxy-propyl)-2-phenyl-pyrimidine-4-carbonyl]-amino}-propionyl)-piperazine-1-carboxylic acid butyl ester:

Raney Nickel in water was decanted, the supernatant was removed and MeOH was added. The process was repeated 3 times and the resulting Raney Nickel in MeOH was added to a solution of intermediate 45.1 (261 mg) in MeOH (15 mL). The mixture was stirred under hydrogen overnight, filtered through Celite and the solution evaporated off. CC (DCM/MeOH 99/1 to 90/10) afforded the desired compound (105 mg).

LC-MS (A): t$_R$=1.05 min; [M+H]$^+$: 648.07.

45.3. 4-((R)-2-{[6-(3-methoxy-propyl)-2-phenyl-pyrimidine-4-carbonyl]-amino}-3-phosphono-propionyl)-piperazine-1-carboxylic acid butyl ester:

This compound was prepared using a method analogous to that of Example 1, step 1.10, intermediate 45.2 replacing intermediate 1.9. The crude was however purified by CC (reverse phase; eluent: gradient from H$_2$O+0.1% TFA to MeCN+0.1% TFA).

LC-MS (A): t$_R$=0.90 min; [M+H]$^+$: 591.94.

Example 46

4-((R)-2-{[6-(3-hydroxy-butyl)-2-phenyl-pyrimidine-4-carbonyl]-amino}-3-phosphono-propionyl)-piperazine-1-carboxylic acid butyl ester 46.1. 4-((R)-3-(diethoxy-phosphoryl)-2-{[6-(3-hydroxy-but-1-ynyl)-2-phenyl-pyrimidine-4-carbonyl]-amino}-propionyl)-piperazine-1-carboxylic acid butyl ester:

This compound was prepared using a method analogous to that of Example 45, step 45.1, 3-butyn-2-ol replacing methylpropargylether.

LC-MS (A): t$_R$=0.99 min; [M+H]$^+$: 643.88.

46.2. 4-((R)-3-(diethoxy-phosphoryl)-2-{[6-(3-hydroxy-butyl)-2-phenyl-pyrimidine-4-carbonyl]-amino}-propionyl)-piperazine-1-carboxylic acid butyl ester:

This compound was prepared using a method analogous to that of Example 45, step 45.2, intermediate 46.1 replacing intermediate 45.1.

LC-MS (A): $t_R$=0.99 min; [M+H]$^+$: 648.09.

46.3. 4-((R)-2-{[6-(3-hydroxy-butyl)-2-phenyl-pyrimidine-4-carbonyl]-amino}-3-phosphono-propionyl)-piperazine-1-carboxylic acid butyl ester:

This compound was prepared using a method analogous to that of Example 1, step 1.10, intermediate 46.2 replacing intermediate 1.9. The crude was however purified by CC (reverse phase; eluent: gradient from H$_2$O+0.1% TFA to MeCN+0.1% TFA).

LC-MS (A): $t_R$=0.84 min; [M+H]$^+$: 591.94.

Example 47

4-((S)-2-{[6-((S)-3-methoxy-pyrrolidin-1-yl)-2-(3-trifluoromethyl-phenyl)-pyrimidine-4-carbonyl]-amino}-4-phosphono-butyryl)-piperazine-1-carboxylic acid butyl ester 47.1. 6-chloro-2-(3-trifluoromethyl-phenyl)-pyrimidine-4-carboxylic acid:

This compound was prepared in 4 steps from 3-trifluoromethylbenzamidine using a method analogous to that described in WO 2006/114774 (see Example 1, step 1.3, Example 24, steps 24.1, 24.2 and 24.3).

LC-MS (A): $t_R$=1.03 min; [M+H]$^+$: 302.69.

47.2. 6-((S)-3-methoxy-pyrrolidin-1-yl)-2-(3-trifluoromethyl-phenyl)-pyrimidine-4-carboxylic acid:

This compound was prepared using a method analogous to that of Example 1, step 1.8, intermediate 47.1 replacing 6-chloro-2-phenyl-pyrimidine-4-carboxylic acid. The compound was however not purified.

LC-MS (A): $t_R$=0.87 min; [M+H]$^+$: 368.02.

47.3. 4-((S)-4-(diethoxy-phosphoryl)-2-{[6-((S)-3-methoxy-pyrrolidin-1-yl)-2-(3-trifluoromethyl-phenyl)-pyrimidine-4-carbonyl]-amino}-butyryl)-piperazine-1-carboxylic acid butyl ester:

This compound was prepared using a method analogous to that of Example 1, step 1.3, intermediate 47.2 replacing intermediate 1.2 and intermediate 5.2 replacing 1-ethoxycarbonylpiperazine. The crude was however purified by CC (DCM/MeOH 97/3 to 80/20).

LC-MS (A): $t_R$=1.14 min; [M+H]$^+$: 756.90.

47.4. 4-((S)-2-{[6-((S)-3-methoxy-pyrrolidin-1-yl)-2-(3-trifluoromethyl-phenyl)-pyrimidine-4-carbonyl]-amino}-4-phosphono-butyryl)-piperazine-1-carboxylic acid butyl ester:

This compound was prepared using a method analogous to that of Example 1, step 1.10, intermediate 47.3 replacing intermediate 1.9. The crude was however purified by CC (reverse phase; eluent: gradient from H$_2$O+0.1% TFA to MeCN+0.1% TFA).

LC-MS (A): $t_R$=1.00 min; [M+H]$^+$: 700.93.

Example 48

4-((S)-4-[bis-(2,2-dimethyl-propionyloxymethoxy)-phosphoryl]-2-{[6-((S)-3-methoxy-pyrrolidin-1-yl)-2-phenyl-pyrimidine-4-carbonyl]-amino}-butyryl)-piperazine-1-carboxylic acid butyl ester To a solution of the compound of Example 5 (100 mg) in anh. DMF (0.7 mL) was added DCMC (95 mg) and chloromethyl pivalate (0.118 ml) under argon. The mixture was stirred for 8 h at 90° C. under argon, cooled down to RT and diluted with toluene. The organic phase was washed with water, dried (Na$_2$SO$_4$) and evaporated off. The crude was purified by CC (eluent: gradient from EA to EA/MeOH 9/1). After freeze-drying, the title compound was obtained as a white solid (53 mg).

LC-MS (A): $t_R$=1.17 min; [M+H]$^+$: 861.12.

Example 49

4-((S)-4-[bis-(isobutyryloxymethoxy)-phosphoryl]-2-{[6-((S)-3-methoxy-pyrrolidin-1-yl)-2-phenyl-pyrimidine-4-carbonyl]-amino}-butyryl)-piperazine-1-carboxylic acid butyl ester This compound was prepared using a method analogous to that of Example 48, chloromethyl isobutyrate (prepared as described in Synth. Commun. (1995), 25(18), 2739-2749) replacing chloromethyl pivalate.

LC-MS (A): $t_R$=1.15 min; [M+H]$^+$: 832.80.

Example 50

4-((S)-4-{bis-[(2,2-dimethyl-propionyloxy)-ethoxy]-phosphoryl}-2-{[6-((S)-3-methoxy-pyrrolidin-1-yl)-2-phenyl-pyrimidine-4-carbonyl]-amino}-butyryl)-piperazine-1-carboxylic acid butyl ester To a solution of the compound of Example 5 (50 mg) in anh. NMP (0.114 mL) was added TEA (0.033 mL) and 1-chloroethyl pivalate (0.063 mL; prepared as described in Synth. Commun. (1995), 25(18), 2739-2749) under argon. The mixture was stirred for 8 h at 60° C. under argon, cooled down on to RT and diluted with toluene. The org. phase was washed with water and brine, dried (Na$_2$SO$_4$) and evaporated off. The crude was purified by CC (solvent A: Hept, solvent B: EA, gradient: 50 to 100% B/15CV, 100% B/5CV) to give the title product as a colourless resin (15 mg; mixture of diastereoisomers).

LC-MS (A): $t_R$=1.22 min; [M+H]$^+$: 889.04.

Example 51

4-((R)-3-[bis-(2,2-dimethyl-propionyloxymethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 50, the compound of Example 2 replacing the compound of Example 5 and chloromethyl pivalate replacing 1-chloroethyl pivalate.

LC-MS (A): $t_R$=1.17 min; [M+H]$^+$: 847.29.

Example 52

4-((R)-3-{bis-[1-(2,2-dimethyl-propionyloxy)-ethoxy]-phosphoryl}-2-{[6-((S)-3-methoxy-pyrrolidin-1-yl)-2-phenyl-pyrimidine-4-carbonyl]-amino}-propionyl)-piperazine-1-carboxylic acid butyl ester To a solution of the compound of Example 2 (200 mg) in anh. DMPU (0.586 mL) was added TEA (0.135 ml) and the mixture was stirred for 10 min under argon. 1-chloroethyl pivalate (0.516 mL; prepared as described in Synth. Commun. (1995), 25(18), 2739-2749) and then NaI (59 mg) were added at RT. The mixture was stirred for 5 h at 60° C. under argon, cooled down to RT and diluted with toluene. The org. phase was washed with water and brine, dried (Na$_2$SO$_4$) and evaporated under reduced pressure. The crude was purified by CC (eluent: gradient from Hept to EA) to give the title product as a yellowish solid (71 mg) after freeze-drying (mixture of diastereoisomers).

LC-MS (A): $t_R$=1.22 min; [M+H]$^+$: 875.08.

Example 53

4-((R)-3-[bis-(1-isobutyryloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 52, 1-chloroethyl isobutyrate (prepared as described in *Synth. Commun.* (1995), 25(18), 2739-2749) replacing 1-chloroethyl pivalate.

LC-MS (A): $t_R$=1.18 min; [M+H]$^+$: 847.01.

Example 54

4-((R)-3-[bis-(1-propionyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 52, 1-chloroethyl propionate (prepared as described in *Synth. Commun.* (1995), 25(18), 2739-2749) replacing 1-chloro ethyl pivalate.

LC-MS (A): $t_R$=1.14 min; [M+H]$^+$: 819.01.

Example 55

4-((R)-3-[bis-(isobutyryloxymethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 52, chloromethyl isobutyrate replacing 1-chloroethyl pivalate.

LC-MS (A): $t_R$=1.15 min; [M+H]$^+$: 818.99.

Example 56

4-(2-{[6-((S)-3-methoxy-pyrrolidin-1-yl)-2-phenyl-pyrimidine-4-carbonyl]-amino}-2-phosphono-acetyl)-piperazine-1-carboxylic acid butyl ester 56.1. Benzyloxycarbonylamino-(dimethoxy-phosphoryl)-acetate lithium salt:

Z-α-phosphonoglycine trimethyl ester (1.6 g) was dissolved in EtOH (5 mL) and treated with a solution of LiOH.H$_2$O (408 mg) in MeOH/H$_2$O (5 mL/2 mL). The mixture was stirred at 0° C. for 30 min and the solvent was removed. The crude (1.5 g) was used directly in the next step.

LC-MS (A): $t_R$=0.75 min; [M+H]$^+$: 318.06.

56.2. 4-[2-Benzyloxycarbonylamino-2-(dimethoxy-phosphoryl)-acetyl]-piperazine-1-carboxylic acid butyl ester:

To a solution of intermediate 56.1 (1.5 g) in DCM (5 mL) was added DIPEA (3.4 mL) and HATU (2.2 g). After stirring at RT for 10 min, intermediate 2.2 (1.1 g) was added. The reaction mixture was stirred overnight at RT and H$_2$O was added. The phases were separated, the org. phase was washed with sat NaCl solution, dried (MgSO$_4$) and evaporated off. The crude was purified by CC (Hept/EA 2/8) to afford the desired compound (1.1 g).

LC-MS (A): $t_R$=0.95 min; [M+H]$^+$: 486.01.

56.3. 4-[2-amino-2-(dimethoxy-phosphoryl)-acetyl]-piperazine-1-carboxylic acid butyl ester:

This compound was prepared using a method analogous to that of Example 2, step 2.2, intermediate 56.2 replacing intermediate 2.1.

LC-MS (A): $t_R$=0.67 min; [M+H]$^+$: 352.55.

56.4. 4-(2-(dimethoxy-phosphoryl)-2-{[6-((S)-3-methoxy-pyrrolidin-1-yl)-2-phenyl-pyrimidine-4-carbonyl]-amino}-acetyl)-piperazine-1-carboxylic acid butyl ester:

This compound was prepared using a method analogous to that of Example 56, step 56.2, intermediate 56.3 replacing intermediate 1.2 and intermediate 1.8 replacing intermediate 56.1. The crude was purified by CC (EA/MeOH 1/0 to 1/9).

LC-MS (A): $t_R$=1.06 min; [M+H]$^+$: 632.98.

56.5. 4-(2-{[6-((S)-3-methoxy-pyrrolidin-1-yl)-2-phenyl-pyrimidine-4-carbonyl]-amino}-2-phosphono-acetyl)-piperazine-1-carboxylic acid butyl ester:

This compound was prepared using a method analogous to that of Example 1, step 1.10, intermediate 56.4 replacing intermediate 1.9. The crude was purified by CC (reverse phase; eluent: gradient from H$_2$O/TFA 100/1 to MeCN/TFA 100/1).

LC-MS (A): $t_R$=0.84 min; [M+H]$^+$: 604.99.

Example 57

4-((R)-2-{[6-(2-Hydroxy-ethoxy)-2-phenyl-pyrimidine-4-carbonyl]-amino}-3-phosphono-propionyl)-piperazine-1-carboxylic acid butyl ester 57.1. 4-((R)-3-(Diethoxy-phosphoryl)-2-{[6-(2-hydroxy-ethoxy)-2-phenyl-pyrimidine-4-carbonyl]-amino}-propionyl)-piperazine-1-carboxylic acid butyl ester:

Ethylene glycol (92 µL) was added to a suspension of NaH (60% dispersion in mineral oil, 65 mg) in DMF (1 mL). The suspension was stirred at RT for 30 min and intermediate 14.1 (200 mg) was added. The reaction mixture was stirred at RT for 3 h. DCM was added and the mixture was washed with a NH$_4$Cl solution and NaCl solution. The aq phases were extracted with DCM. The combined org. layers were dried (MgSO$_4$) and evaporated off. CC (DCM/MeOH 95/5 to 90/10) of the crude offered 209 mg of the desired compound.

LC-MS (A): $t_R$=0.97 min; [M+H]$^+$: 635.97.

57.2. 4-((R)-2-{[6-(2-Hydroxy-ethoxy)-2-phenyl-pyrimidine-4-carbonyl]-amino}-3-phosphono-propionyl)-piperazine-1-carboxylic acid butyl ester:

This compound was prepared using a method analogous to that of Example 38 step 38.4, intermediate 57.1 replacing intermediate 38.3, using no water. The crude was purified by preparative LC-MS (I).

LC-MS (A): $t_R$=0.83 min; [M+H]$^+$: 579.83.

Example 58

4-((S)-2-{[6-((S)-3-Methoxy-pyrrolidin-1-yl)-2-phenyl-pyrimidine-4-carbonyl]-amino}-5-phosphono-pentanoyl)-piperazine-1-carboxylic acid butyl ester 58.1. (S)-2-Benzyloxycarbonylamino-5-hydroxy-pentanoic acid methyl ester:

To a cold (−15° C.) solution of Z-Glu-OMe (1.5 g) in THF (70 mL) was added N-methylmorpholine (0.616 mL) followed by isobutyl chloroformate (0.731 mL) dropwise. After 30 min stirring at −15° C., NaBH₄ (576 mg) was added, followed by MeOH dropwise. The reaction mixture was stirred at −10° C. for 15 min and quenched by the addition of 1M KHSO₄ solution. The mixture was extracted with EA. The org. phase was washed with water, dried (Na₂SO₄) and evaporated off to give 1.5 g of the crude product as colorless oil.

LC-MS (A): $t_R$=0.82 min; [M+H]⁺: 282.11.

58.2. (S)-2-Benzyloxycarbonylamino-5-iodo-pentanoic acid methyl ester:

To a solution of intermediate 58.1 (1.4 g) in THF (40 mL) were added imidazole (545 mg) and triphenylphosphine (1.97 g). The mixture was cooled down to 0° C. and iodine (1.9 g) was added portion wise. After 10 min, the reaction mixture was allowed to warm to RT and was stirred at RT for 4 h. An aq. solution of Na₂S₂O₃ was added to the mixture that was further diluted with Et₂O. The phases were separated and the org. phase was washed with water, dried (MgSO₄) and evaporated off to afford 3.5 g of the crude compound as yellow oil.

LC-MS (A): $t_R$=1.04 min; [M+H]⁺: 391.87.

58.3. (S)-2-Benzyloxycarbonylamino-5-(diethoxy-phosphoryl)-pentanoic acid methyl ester:

This compound was prepared using a method analogous to that of Example 1 step 1.1, intermediate 58.2 replacing Boc-3-iodo-L-Ala-OMe.

LC-MS (A): $t_R$=0.92 min; [M+H]⁺: 402.02.

58.4. (S)-2-Benzyloxycarbonylamino-5-(diethoxy-phosphoryl)-pentanoic acid:

This compound was prepared using a method analogous to that of Example 56 step 56.1, intermediate 58.3 replacing Z-α-phosphinoglycine trimethyl ester.

LC-MS (A): $t_R$=0.80 min; [M+H]⁺: 388.19.

58.5. 4-[(S)-2-Benzyloxycarbonylamino-5-(diethoxy-phosphoryl)-pentanoyl]-piperazine-1-carboxylic acid butyl ester:

This compound was prepared using a method analogous to that of Example 1 step 1.3, intermediate 58.4 replacing intermediate 1.2 and intermediate 2.2 replacing 1-ethoxycarbonylpiperazine.

LC-MS (A): $t_R$=0.97 min; [M+H]⁺: 555.98.

58.6. 4-[(S)-2-Amino-5-(diethoxy-phosphoryl)-pentanoyl]-piperazine-1-carboxylic acid butyl ester:

This compound was prepared using a method analogous to that of Example 2 step 2.2, intermediate 58.5 replacing intermediate 2.1.

LC-MS (A): $t_R$=0.74 min; [M+H]⁺: 422.12.

58.7. 4-((S)-5-(Diethoxy-phosphoryl)-2-{[6-((S)-3-methoxy-pyrrolidin-1-yl)-2-phenyl-pyrimidine-4-carbonyl]-amino}-pentanoyl)-piperazine-1-carboxylic acid butyl ester:

This compound was prepared using a method analogous to that of Example 56 step 56.2, intermediate 58.6 replacing intermediate 2.2 and intermediate 1.8 replacing intermediate 56.1. The compound was purified by CC (EA to EA/MeOH 9/1).

LC-MS (A): $t_R$=1.07 min; [M+H]⁺: 703.53.

58.8. 4-((S)-2-{[6-((S)-3-Methoxy-pyrrolidin-1-yl)-2-phenyl-pyrimidine-4-carbonyl]-amino}-5-phosphono-pentanoyl)-piperazine-1-carboxylic acid butyl ester:

This compound was prepared using a method analogous to that of Example 1 step 1.10, intermediate 58.7 replacing intermediate 1.9. The compound was purified by CC (reverse phase, water/MeCN 1/0 to 0/1).

LC-MS (A): $t_R$=0.95 min; [M+H]⁺: 647.05.

Example 59

4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid ethyl ester 59.1 (S)-2-tent-Butoxycarbonylamino-3-(4-iodo-phenyl)-propionic acid ethyl ester:

To a solution of Boc-Phe(4-I)-OH (3 g), DMAP (187 mg) and DIPEA (3.94 mL) in EtOH (38 mL) was added PyBOP (6 g) and the reaction mixture was stirred at RT overnight. EA and water were added, the org. phase was washed with 10% citric acid solution, sat. Na₂CO₃ solution, dried (MgSO₄) and evaporated off. The crude was purified by CC (eluant A: Hept, eluant B: EA, 0 to 100% B) to afford 3.07 g of the desired compound as white powder.

LC-MS (A): $t_R$=1.10 min; [M+H]⁺: 419.78.

59.2 2-(S)-tent-Butoxycarbonylamino-3-[4-(diethoxy-phosphoryl)-phenyl]-propionic acid ethyl ester:

To a solution of intermediate 59.1 (3.07 g) and Pd(PPh₃)₄ (254 mg) in MeCN (128 mL) was added diethylphosphite (1.4 mL) followed by NEt₃ (2 mL). The reaction mixture was stirred overnight at 70° C., then refluxed for 20 h. Pd(PPh₃)₄ (846 mg) was added and the mixture was further refluxed for 20 h. The solvent was evaporated off. The oily brown residue was dissolved in EA and washed with a 10% citric acid solution, sat. Na₂CO₃ solution, water, sat. NaCl solution, dried (MgSO₄) and evaporated off. The crude was purified by CC (eluant A: Hept, eluant B: EA, 10 to 100% B; 3 batches were obtained; batch n° 2 was repurified: eluant A: Hept, eluant B: EA, 40 to 60% B; batch n° 3 was repurified: eluant A: DCM, eluant B: DCM/MeOH 20/1, 0 to 100% B) to afford 2.79 g of the desired product.

LC-MS (A): $t_R$=0.98 min; [M+H]⁺: 430.05.

59.3. (S)-2-tert-Butoxycarbonylamino-3-[4-(diethoxy-phosphoryl)-phenyl]-propionic acid:

This compound was prepared using a method analogous to that of Example 1 step 1.2, intermediate 59.2 replacing intermediate 1.1.

LC-MS (A): $t_R$=0.86 min; [M+H]⁺: 402.01.

59.4. 4-{(S)-2-tert-Butoxycarbonylamino-3-[4-(diethoxy-phosphoryl)-phenyl]-propionyl}-piperazine-1-carboxylic acid ethyl ester:

This compound was prepared using a method analogous to that of Example 56 step 56.2, intermediate 59.3 replacing intermediate 56.1, 1-ethoxycarbonylpiperazine replacing intermediate 2.2 and using DCM/THF 4/1 instead of DCM. The compound was purified by CC (First purification: Hept/EA 1/0 to 3/1; followed by: eluant A: EA, eluant B: EA/MeOH 9/1, 0 to 100% B; second purification: eluant A: EA, eluant B: EA/MeOH 40/1, 0 to 100% B).

LC-MS (A): $t_R$=0.93 min; [M+H]⁺: 542.01.

59.5. 4-{(S)-2-Amino-3-[4-(diethoxy-phosphoryl)-phenyl]-propionyl}-piperazine-1-carboxylic acid ethyl ester hydrochloride salt:

This compound was prepared using a method analogous to that of Example 1 step 1.4, intermediate 59.4 replacing intermediate 1.3.

LC-MS (A): $t_R$=0.69 min; [M+H]⁺: 442.11.

59.6. 4-((S)-3-[4-(Diethoxy-phosphoryl)-phenyl]-2-{[6-((S)-3-methoxy-pyrrolidin-1-yl)-2-phenyl-pyrimidine-4-carbonyl]-amino}-propionyl)-piperazine-1-carboxylic acid ethyl ester:

This compound was prepared using a method analogous to that of Example 56 step 56.2, intermediate 59.5 replacing intermediate 2.2, intermediate 1.8 replacing intermediate 56.1 and using DCM/THF 4/1 instead of DCM. The compound was purified by CC (EA to EA/MeOH 1/1).

LC-MS (A): $t_R$=1.06 min; [M+H]$^+$: 722.99.

59.7. 4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid ethyl ester:

This compound was prepared using a method analogous to that of Example 1 step 1.10, intermediate 59.6 replacing intermediate 1.9. The compound was purified by CC (reverse phase; eluant A: H$_2$O+1% TFA; eluant B: MeCN+1% TFA; gradient: 5 to 80% B).

LC-MS (A): $t_R$=0.89 min; [M+H]$^+$: 667.20.

Example 60

4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid butyl ester 60.1. 4-{(S)-2-tert-Butoxycarbonylamino-3-[4-(diethoxy-phosphoryl)-phenyl]-propionyl}-piperazine-1-carboxylic acid butyl ester:

This compound was prepared using a method analogous to that of Example 56 step 56.2, intermediate 59.3 replacing intermediate 56.1 and using DCM/THF 4/1 instead of DCM. The compound was purified by CC (First purification: eluant A: EA, eluant B: EA/MeOH 9/1, 0 to 40% B; second purification: eluant A: EA, eluant B: EA/MeOH 40/1, 0 to 100% B).

LC-MS (A): $t_R$=1.00 min; [M+H]$^+$: 569.98.

60.2. 4-{(S)-2-Amino-3-[4-(diethoxy-phosphoryl)-phenyl]-propionyl}-piperazine-1-carboxylic acid butyl ester hydrochloride salt:

This compound was prepared using a method analogous to that of Example 1 step 1.4, intermediate 60.1 replacing intermediate 1.3.

LC-MS (A): $t_R$=0.76 min; [M+H]$^+$: 470.11.

60.3. 4-((S)-3-[4-(Diethoxy-phosphoryl)-phenyl]-2-{[6-((S)-3-methoxy-pyrrolidin-1-yl)-2-phenyl-pyrimidine-4-carbonyl]-amino}-propionyl)-piperazine-1-carboxylic acid butyl ester:

This compound was prepared using a method analogous to that of Example 56 step 56.2, intermediate 60.2 replacing intermediate 2.2, intermediate 1.8 replacing intermediate 56.1 and using DCM/THF 4/1 instead of DCM. The compound was purified by CC (eluant A: EA, eluant B: EA/MeOH 25/1, 0 to 100% B).

LC-MS (A): $t_R$=1.11 min; [M+H]$^+$: 751.00.

60.4. 4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid butyl ester:

This compound was prepared using a method analogous to that of Example 1 step 1.10, intermediate 60.3 replacing intermediate 1.9. The compound was purified by CC (reverse phase; eluant A: H$_2$O+1% TFA; eluant B: MeCN+1% TFA; gradient: 5 to 80% B).

LC-MS (A): $t_R$=0.95 min; [M+H]$^+$: 695.35.

Example 61

4-[(S)-2-{[6-((S)-3-Methoxy-pyrrolidin-1-yl)-2-phenyl-pyrimidine-4-carbonyl]-amino}-3-(4-phosphonomethyl-phenyl)-propionyl]-piperazine-1-carboxylic acid ethyl ester 61.1. 4-{(S)-2-Amino-3-[4-(diethoxy-phosphorylmethyl)-phenyl]-propionyl}-piperazine-1-carboxylic acid ethyl ester:

This compound was prepared using a method analogous to that of Example 1 step 1.3, Fmoc-p(CH$_2$—PO$_3$Et$_2$)-L-Phe-OH replacing intermediate 1.2. The Fmoc group was cleaved during the reaction. The compound was purified by CC (eluant A: EA/NEt$_3$ 100/1, eluant B: EA/MeOH/NEt$_3$ 50/50/1, 0 to 100% B, followed by elution with MeOH) to afford 448 mg of the desired compound.

LC-MS (A): $t_R$=0.71 min; [M+H]$^+$: 456.08.

61.2. 4-((S)-3-[4-(Diethoxy-phosphorylmethyl)-phenyl]-2-{[6-((S)-3-methoxy-pyrrolidin-1-yl)-2-phenyl-pyrimidine-4-carbonyl]-amino}-propionyl)-piperazine-1-carboxylic acid ethyl ester:

This compound was prepared using a method analogous to that of Example 56 step 56.2, intermediate 61.1 replacing intermediate 2.2, intermediate 1.8 replacing intermediate 56.1 and using DCM/THF 4/1 instead of DCM. The compound was purified by CC (eluant A: EA, eluant B: EA/MeOH 9/1, 0 to 100% B).

LC-MS (A): $t_R$=1.06 min; [M+H]$^+$: 737.24.

61.3. 4-[(S)-2-{[6-((S)-3-Methoxy-pyrrolidin-1-yl)-2-phenyl-pyrimidine-4-carbonyl]-amino}-3-(4-phosphonomethyl-phenyl)-propionyl]-piperazine-1-carboxylic acid ethyl ester:

This compound was prepared using a method analogous to that of Example 1 step 1.10, intermediate 61.2 replacing intermediate 1.9. The compound was purified by CC (reverse phase; eluant A: H$_2$O+1% TFA; eluant B: MeCN+1% TFA; gradient: 5 to 90% B).

LC-MS (A): $t_R$=0.91 min; [M+H]$^+$: 681.06.

Example 62

4-[(S)-2-{[6-((S)-3-Methoxy-pyrrolidin-1-yl)-2-phenyl-pyrimidine-4-carbonyl]-amino}-3-(4-phosphonomethyl-phenyl)-propionyl]-piperazine-1-carboxylic acid butyl ester 62.1. 4-{(S)-2-Amino-3-[4-(diethoxy-phosphorylmethyl)-phenyl]-propionyl}-piperazine-1-carboxylic acid butyl ester:

This compound was prepared using a method analogous to that of Example 1 step 1.3, Fmoc-p(CH$_2$—PO$_3$Et$_2$)-L-Phe-OH replacing intermediate 1.2 and intermediate 2.2 replacing 1-ethoxy-carbonylpiperazine. The Fmoc group was cleaved during the reaction. The compound was purified by CC (eluant A: EA/NEt$_3$ 100/1, eluant B: EA/MeOH/NEt$_3$ 50/50/1, 0 to 100% B) to afford 448 mg of the desired compound.

LC-MS (A): $t_R$=0.77 min; [M+H]$^+$: 484.00.

62.2. 4-((S)-3-[4-(Diethoxy-phosphorylmethyl)-phenyl]-2-{[6-((S)-3-methoxy-pyrrolidin-1-yl)-2-phenyl-pyrimidine-4-carbonyl]-amino}-propionyl)-piperazine-1-carboxylic acid butyl ester:

This compound was prepared using a method analogous to that of Example 56 step 56.2, intermediate 62.1 replacing intermediate 2.2, intermediate 1.8 replacing intermediate 56.1 and using DCM/THF 4/1 instead of DCM. The compound was purified by CC (eluant A: EA, eluant B: EA/MeOH 9/1, first purification: 0 to 100% B; second purification: 20 to 100% B).

LC-MS (A): $t_R$=1.12 min; [M+H]$^+$: 765.02.

62.3. 4-[(S)-2-{[6-((S)-3-Methoxy-pyrrolidin-1-yl)-2-phenyl-pyrimidine-4-carbonyl]-amino}-3-(4-phosphonomethyl-phenyl)-propionyl]-piperazine-1-carboxylic acid butyl ester:

This compound was prepared using a method analogous to that of Example 1 step 1.10, intermediate 62.2 replacing intermediate 1.9. The compound was purified by CC (reverse phase; eluant A: H$_2$O+1% TFA; eluant B: MeCN+1% TFA; gradient: 5 to 90% B).

LC-MS (A): t$_R$=0.97 min; [M+H]$^+$: 709.15.

Example 63

4-((R)-2-{[6-((S)-3-Methoxy-pyrrolidin-1-yl)-2-phenyl-pyrimidine-4-carbonyl]-amino}-5-phosphono-pentanoyl)-piperazine-1-carboxylic acid butyl ester 63.1. (R)-2-Benzyloxycarbonylamino-5-hydroxy-pentanoic acid methyl ester:
This compound was prepared using a method analogous to that of Example 58 step 58.1, Z-D-Glu-OMe replacing Z-Glu-OMe.
LC-MS (A): t$_R$=0.82 min; [M+H]$^+$: 282.11.

63.2. (R)-2-Benzyloxycarbonylamino-5-iodo-pentanoic acid methyl ester:
This compound was prepared using a method analogous to that of Example 58 step 58.2, intermediate 63.1 replacing intermediate 58.1.
LC-MS (A): t$_R$=1.04 min; [M+H]$^+$: 391.84.

63.3. (R)-2-Benzyloxycarbonylamino-5-(diethoxy-phosphoryl)-pentanoic acid methyl ester:
This compound was prepared using a method analogous to that of Example 1 step 1.1, intermediate 63.2 replacing Boc-3-iodo-L-Ala-OMe.
LC-MS (A): t$_R$=0.92 min; [M+H]$^+$: 402.02.

63.4. (R)-2-Benzyloxycarbonylamino-5-(diethoxy-phosphoryl)-pentanoic acid:
This compound was prepared using a method analogous to that of Example 56 step 56.1, intermediate 63.3 replacing Z-α-phosphinoglycine trimethyl ester.
LC-MS (A): t$_R$=0.80 min; [M+H]$^+$: 388.09.

63.5. 4-[(R)-2-Benzyloxycarbonylamino-5-(diethoxy-phosphoryl)-pentanoyl]-piperazine-1-carboxylic acid butyl ester:
This compound was prepared using a method analogous to that of Example 56 step 56.2, intermediate 63.4 replacing intermediate 56.1. The compound was purified by CC (Hept/EA 2/8, then EA/MeOH 10/1).
LC-MS (A): t$_R$=0.98 min; [M+H]$^+$: 556.02.

63.6. 4-[(R)-2-Amino-5-(diethoxy-phosphoryl)-pentanoyl]-piperazine-1-carboxylic acid butyl ester:
This compound was prepared using a method analogous to that of Example 2 step 2.2, intermediate 63.5 replacing intermediate 2.1.
LC-MS (A): t$_R$=0.74 min; [M+H]$^+$: 422.13.

63.7. 4-((R)-5-(Diethoxy-phosphoryl)-2-{[6-((S)-3-methoxy-pyrrolidin-1-yl)-2-phenyl-pyrimidine-4-carbonyl]-amino}-pentanoyl)-piperazine-1-carboxylic acid butyl ester:
This compound was prepared using a method analogous to that of Example 56 step 56.2, intermediate 63.6 replacing intermediate 2.2 and intermediate 1.8 replacing intermediate 56.1. The compound was purified by CC (EA/MeOH 8/2, then EA/MeOH 9/1).
LC-MS (A): t$_R$=1.08 min; [M+H]$^+$: 703.04.

63.8. 4-((R)-2-{[6-((S)-3-Methoxy-pyrrolidin-1-yl)-2-phenyl-pyrimidine-4-carbonyl]-amino}-5-phosphono-pentanoyl)-piperazine-1-carboxylic acid butyl ester:
This compound was prepared using a method analogous to that of Example 1 step 1.10, intermediate 63.7 replacing intermediate 1.9. The compound was purified by CC (reverse phase, water/MeCN 1/0 to 0/1).
LC-MS (A): t$_R$=0.95 min; [M+H]$^+$: 647.04.

Example 64

4-{(R)-2-[(6-Isopropyl-2-phenyl-pyrimidine-4-carbonyl)-amino]-3-phosphono-propionyl}-piperazine-1-carboxylic acid butyl ester 64.1. 4-{(S)-2-Amino-3-[4-(diethoxy-phosphorylmethyl)-phenyl]-propionyl}-piperazine-1-carboxylic acid butyl ester:
Isopropylmagnesium bromide (1M in THF, 0.164 mL) was added to an orange solution of intermediate 14.1 (100 mg) and iron(III) acetylacetonate (3 mg) in anhydrous THF (1.6 ml) under argon. After stirring at RT for 48 h, isopropylmagnesium bromide (1M in THF, 0.820 mL) was added and the mixture was further stirred for 35 min A 1M HCl solution (1 mL) was added and it was allowed to stir for 1.5 h. EA was added, the phases were separated, the org. phase was dried (Na$_2$SO$_4$) and evaporated off. CC (EA to EA/MeOH 100/1; followed by: Hept/EA 1/0 to 0/1; finally: DCM to DCM/MeOH 20/1) offered 40 mg of the desired compound.
LC-MS (A): t$_R$=1.10 min; [M+H]$^+$: 618.03.

64.2. 4-{(R)-2-[(6-Isopropyl-2-phenyl-pyrimidine-4-carbonyl)-amino]-3-phosphono-propionyl}-piperazine-1-carboxylic acid butyl ester:
This compound was prepared using a method analogous to that of Example 1 step 1.10, intermediate 64.1 replacing intermediate 1.9. The compound was purified by CC (reverse phase; eluant A: H$_2$O+1% TFA; eluant B: MeCN+1% TFA; gradient: 5 to 80% B).
LC-MS (A): t$_R$=0.95 min; [M+H]$^±$: 561.98.

Example 65

4-((R)-2-{[6-(3-Methoxymethyl-azetidin-1-yl)-2-phenyl-pyrimidine-4-carbonyl]-amino}-3-phosphono-propionyl)-piperazine-1-carboxylic acid butyl ester 65.1. (1-Benzhydryl-azetidin-3-yl)-methanol:
1-Benzhydrylazetane-3-carboxylic acid (101 mg) was dissolved in THF (2 mL) and lithium aluminium hydride (27 mg) was added. The mixture was stirred overnight at RT. Water, sodium potassium tartrate solution and EA were added. The phases were separated, the org. phase was dried (Na$_2$SO$_4$) and evaporated off to afford 93 mg of the desired product.
LC-MS (A): t$_R$=0.67 min; [M+H]$^+$: 254.16.

65.2. 1-Benzhydryl-3-methoxymethyl-azetidine:
To an ice-cold solution of intermediate 65.1 (91 mg) in THF (1 mL) was added NaH (60% in mineral oil, 17 mg). The mixture was allowed to warm to RT and was stirred for 30 min at RT. Methyl iodide (45 µL) was added and the mixture was stirred at RT for 4 h. Sat. Na$_2$CO$_3$ solution was added, the organic phase was washed with brine, dried (Na$_2$SO$_4$) and evaporated off to afford 96 mg of the desired product.
LC-MS (A): t$_R$=0.78 min; [M+H]$^+$: 268.16.

65.3. 3-Methoxymethyl-azetidine:
This compound was prepared using a method analogous to that of Example 2 step 2.2, a mixture of MeOH/1M HCl 1/0.1 replacing EtOH.
$^1$H-NMR (CD$_3$OD): δ=4.15 (br. s, 2H); 3.98 (br. s, 2H); 3.54 (s, 2H); 3.44 (s, 3H); 3.11 (s, 1H).

65.4. 4-((R)-3-(Diethoxy-phosphoryl)-2-{[6-(3-methoxymethyl-azetidin-1-yl)-2-phenyl-pyrimidine-4-carbonyl]-amino}-propionyl)-piperazine-1-carboxylic acid butyl ester:
This compound was prepared using a method analogous to that of Example 1 step 1.8, intermediate 65.3 replacing intermediate 1.7.
LC-MS (A): t$_R$=1.05 min; [M+H]$^+$: 675.25.

65.5. 4-((R)-2-{[6-(3-Methoxymethyl-azetidin-1-yl)-2-phenyl-pyrimidine-4-carbonyl]-amino}-3-phosphono-propionyl)-piperazine-1-carboxylic acid butyl ester:

This compound was prepared using a method analogous to that of Example 38 step 38.4, intermediate 65.4 replacing intermediate 38.3. The compound was purified by CC (reverse phase; eluant A: H$_2$O+0.1% TFA; eluant B: MeCN+0.1% TFA; gradient: 5 to 90% B).

LC-MS (A): t$_R$=0.90 min; [M+H]$^+$: 619.65.

Example 66

4-{(R)-2-[(6-Cyclopentyloxy-2-phenyl-pyrimidine-4-carbonyl)-amino]-3-phosphono-propionyl}-piperazine-1-carboxylic acid ethyl ester 66.1. 4-[(R)-2-[(6-Cyclopentyloxy-2-phenyl-pyrimidine-4-carbonyl)-amino]-3-(diethoxy-phosphoryl)-propionyl]-piperazine-1-carboxylic acid ethyl ester:

This compound was prepared using a method analogous to that of Example 1 step 1.9, 6-cyclopentyloxy-2-phenyl-pyrimidine-4-carboxylic acid (prepared as described in WO06114774, Example 1, intermediate 1.7) replacing intermediate 1.8.

LC-MS (A): t$_R$=1.09 min; [M+H]$^+$: 632.72.

66.2. 4-{(R)-2-[(6-Cyclopentyloxy-2-phenyl-pyrimidine-4-carbonyl)-amino]-3-phosphono-propionyl}-piperazine-1-carboxylic acid ethyl ester:

This compound was prepared using a method analogous to that of Example 38 step 38.4, intermediate 66.1 replacing intermediate 38.3. The compound was purified by preparative LC-MS (IV).

LC-MS (A): t$_R$=0.97 min; [M+H]$^+$: 576.72.

Example 67

4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid ethyl ester 67.1. (S)-3-(3-Bromo-phenyl)-2-tert-butoxycarbonylamino-propionic acid ethyl ester:

This compound was prepared using a method analogous to that of Example 59 step 59.1, (S)-N-Boc-3-bromophenylalanine replacing Boc-Phe(4-I)-OH. The compound was purified by CC (eluant A: EA, eluant B: MeOH, 0 to 20% B).

LC-MS (A): t$_R$=1.09 min; [M+H]$^+$: 372.20.

67.2. (S)-2-tert-Butoxycarbonylamino-3-[3-(diethoxy-phosphoryl)-phenyl]-propionic acid ethyl ester:

To a solution of NEt$_3$ (1.32 mL), diethylphosphite (0.83 mL) and Pd(PPh$_3$)$_4$ (428 mg) in toluene (10 mL) was added a solution of intermediate 67.1 (741 mg) in toluene (2 mL). The reaction mixture was stirred overnight at 105° C. under nitrogen. After cooling down, Et$_2$O (60 mL) was added and the mixture was filtered and evaporated off. The crude oil was purified by CC (EA/Hept 1/1 to 2/1) to afford 898 mg of the desired product as yellow oil.

LC-MS (A): t$_R$=0.99 min; [M+H]$^+$: 430.42.

67.3. (S)-2-tert-Butoxycarbonylamino-3-[3-(diethoxy-phosphoryl)-phenyl]-propionic acid:

This compound was prepared using a method analogous to that of Example 1 step 1.2, intermediate 67.2 replacing intermediate 1.1.

LC-MS (A): t$_R$=0.88 min; [M+H]$^+$: 402.40.

67.4. 4-{(S)-2-tert-Butoxycarbonylamino-3-[3-(diethoxy-phosphoryl)-phenyl]-propionyl}-piperazine-1-carboxylic acid ethyl ester:

This compound was prepared using a method analogous to that of Example 56 step 56.2, intermediate 67.3 replacing intermediate 56.1, 1-ethoxycarbonylpiperazine replacing intermediate 2.2 and using DCM/THF 4/1 instead of DCM. The compound was purified by CC (first purification: eluant A: EA, eluant B: EA/MeOH 9/1, 0 to 100% B; second purification: eluant A: Hept, eluant B: EA, 50 to 100% B).

LC-MS (A): t$_R$=0.94 min; [M+H]$^+$: 542.38.

67.5. 4-{(S)-2-Amino-3-[3-(diethoxy-phosphoryl)-phenyl]-propionyl}-piperazine-1-carboxylic acid ethyl ester hydrochloride salt:

This compound was prepared using a method analogous to that of Example 1 step 1.4, intermediate 67.4 replacing intermediate 1.3.

LC-MS (A): t$_R$=0.70 min; [M+H]$^+$: 442.38.

67.6. 4-((S)-3-[3-(Diethoxy-phosphoryl)-phenyl]-2-{[6-((S)-3-methoxy-pyrrolidin-1-yl)-2-phenyl-pyrimidine-4-carbonyl]-amino}-propionyl)-piperazine-1-carboxylic acid ethyl ester:

This compound was prepared using a method analogous to that of Example 56 step 56.2, intermediate 67.5 replacing intermediate 2.2, intermediate 1.8 replacing intermediate 56.1 and using DCM/THF 4/1 instead of DCM. The compound was purified by CC (eluant A: EA, eluant B: EA/MeOH 9/1, 0 to 50% B).

LC-MS (A): t$_R$=1.06 min; [M+H]$^+$: 732.82.

67.7. 4-[(S)-2-{[6-((S)-3-Methoxy-pyrrolidin-1-yl)-2-phenyl-pyrimidine-4-carbonyl]-amino}-3-(3-phosphono-phenyl)-propionyl]-piperazine-1-carboxylic acid ethyl ester:

This compound was prepared using a method analogous to that of Example 1 step 1.10, intermediate 67.6 replacing intermediate 1.9. The compound was purified by CC (reverse phase; eluant A: H$_2$O+1% TFA; eluant B: MeCN+1% TFA; gradient: 5 to 80% B).

LC-MS (A): t$_R$=0.90 min; [M+H]$^+$: 667.64.

Example 68

4-[2-{[6-((S)-3-Methoxy-pyrrolidin-1-yl)-2-phenyl-pyrimidine-4-carbonyl]-amino}-2-(4-phosphono-phenyl)-acetyl]-piperazine-1-carboxylic acid ethyl ester 68.1. rac-(4-Bromo-phenyl)-tert-butoxycarbonylamino-acetic acid:

To an ice-cold solution of amino-(4-bromo-phenyl)-acetic acid (3 g) in dioxane (13 mL) and NaOH solution (1M, 19.6 mL) was added di-tert-butyl-dicarbonate (3.4 g). The mixture was allowed to warm to RT and was stirred overnight at RT. The white suspension was partitioned between DCM and citric acid (10%). The aqueous phase was extracted twice with DCM. The combined org. phases were dried (Na$_2$SO$_4$) and evaporated off to afford 5 g of the desired product as white solid.

LC-MS (A): t$_R$=0.96 min; [M+H]$^+$: 330.08.

68.2. rac-(4-Bromo-phenyl)-tert-butoxycarbonylamino-acetic acid ethyl ester:

This compound was prepared using a method analogous to that of Example 59 step 59.1, intermediate 68.1 replacing Boc-Phe(4-I)-OH. The compound was purified by CC (Hept/EA, 1/0 to 0/1).

LC-MS (A): t$_R$=1.08 min; [M+H]$^+$: 399.24.

68.3. rac-tert-Butoxycarbonylamino-[4-(diethoxy-phosphoryl)-phenyl]-acetic acid ethyl ester:

To Pd(PPh$_3$)$_4$ (2.44 g) degassed and put under argon was added NEt$_3$ (8.6 mL) and diethylphosphite (5.3 mL). A solution of intermediate 68.2 (4.26 g) in anhydrous toluene (123 mL) was added and the mixture was heated up at 105° C. overnight under a constant flow of argon. After cooling down, the reaction mixture was washed with citric acid (10%), sat. aq. NaHCO$_3$ solution, dried (Na$_2$SO$_4$) and evaporated off. The crude oil was purified by CC (Hept/EA 1/0 to 0/1) to afford 3.76 g of the desired product as colorless resin.

LC-MS (A): t$_R$=0.99 min; [M+H]$^+$: 415.84.

68.4. rac-tert-Butoxycarbonylamino-[4-(diethoxy-phosphoryl)-phenyl]-acetic acid:

This compound was prepared using a method analogous to that of Example 1 step 1.2, intermediate 68.3 replacing intermediate 1.1.

LC-MS (A): t$_R$=0.87 min; [M+H]$^+$: 429.18.

68.5. rac-4-{2-tert-Butoxycarbonylamino-2-[4-(diethoxy-phosphoryl)-phenyl]-acetyl}-piperazine-1-carboxylic acid ethyl ester:

This compound was prepared using a method analogous to that of Example 56 step 56.2, 1-ethoxycarbonylpiperazine replacing intermediate 2.2, intermediate 68.4 replacing intermediate 56.1 and using DCM/THF 4/1 instead of DCM. The crude was purified by CC (eluant A: EA, eluant B: EA/MeOH 40/1, 0 to 20% B).

LC-MS (A): t$_R$=0.95 min; [M+H]$^+$: 528.64.

68.6. rac-4-{2-Amino-2-[4-(diethoxy-phosphoryl)-phenyl]-acetyl}-piperazine-1-carboxylic acid ethyl ester, hydrochloride salt:

This compound was prepared using a method analogous to that of Example 1 step 1.4, intermediate 68.5 replacing intermediate 1.3.

LC-MS (A): t$_R$=0.69 min; [M+H]$^+$: 428.24.

68.7. 4-(2-[4-(Diethoxy-phosphoryl)-phenyl]-2-{[6-((S)-3-methoxy-pyrrolidin-1-yl)-2-phenyl-pyrimidine-4-carbonyl]-amino}-acetyl)-piperazine-1-carboxylic acid ethyl ester:

This compound was prepared using a method analogous to that of Example 56 step 56.2, intermediate 68.6 replacing intermediate 2.2, intermediate 1.8 replacing intermediate 56.1 and using DCM/THF 4/1 instead of DCM. The compound was purified by CC (eluant A: EA, eluant B: EA/MeOH 9/1, 0 to 100% B).

LC-MS (A): t$_R$=1.08 min; [M+H]$^+$: 709.74.

68.8. 4-[2-{[6-((S)-3-Methoxy-pyrrolidin-1-yl)-2-phenyl-pyrimidine-4-carbonyl]-amino}-2-(4-phosphono-phenyl)-acetyl]-piperazine-1-carboxylic acid ethyl ester:

This compound was prepared using a method analogous to that of Example 1 step 1.10, intermediate 68.7 replacing intermediate 1.9. The compound was purified by CC (reverse phase; eluant A: H$_2$O; eluant B: MeCN; gradient: 5 to 80% B).

LC-MS (A): t$_R$=0.89 min; [M+H]$^+$: 653.67.

Example 69

4-[2-{[6-((S)-3-Methoxy-pyrrolidin-1-yl)-2-phenyl-pyrimidine-4-carbonyl]-amino}-2-(4-phosphono-phenyl)-acetyl]-piperazine-1-carboxylic acid butyl ester 69.1. rac-4-{2-tert-Butoxycarbonylamino-2-[4-(diethoxy-phosphoryl)-phenyl]-acetyl}-piperazine-1-carboxylic acid butyl ester:

This compound was prepared using a method analogous to that of Example 56 step 56.2, intermediate 68.4 replacing intermediate 56.1 and using DCM/THF 4/1 instead of DCM. The crude was purified by CC (eluant A: EA, eluant B: EA/MeOH 40/1, 0 to 100% B).

LC-MS (A): t$_R$=1.02 min; [M+H]$^+$: 556.69.

69.2. rac-4-{2-Amino-2-[4-(diethoxy-phosphoryl)-phenyl]-acetyl}-piperazine-1-carboxylic acid butyl ester, hydrochloride salt:

This compound was prepared using a method analogous to that of Example 1 step 1.4, intermediate 69.1 replacing intermediate 1.3.

LC-MS (A): t$_R$=0.76 min; [M+H]$^+$: 456.08.

69.3. 4-(2-[4-(Diethoxy-phosphoryl)-phenyl]-2-{[6-((S)-3-methoxy-pyrrolidin-1-yl)-2-phenyl-pyrimidine-4-carbonyl]-amino}-acetyl)-piperazine-1-carboxylic acid butyl ester:

This compound was prepared using a method analogous to that of Example 56 step 56.2, intermediate 69.2 replacing intermediate 2.2, intermediate 1.8 replacing intermediate 56.1 and using DCM/THF 4/1 instead of DCM. The compound was purified by CC (eluant A: EA, eluant B: EA/MeOH 9/1, 0 to 100% B).

LC-MS (A): t$_R$=1.13 min; [M+H]$^+$: 737.78.

69.4. 4-[2-{[6-((S)-3-Methoxy-pyrrolidin-1-yl)-2-phenyl-pyrimidine-4-carbonyl]-amino}-2-(4-phosphono-phenyl)-acetyl]-piperazine-1-carboxylic acid butyl ester:

This compound was prepared using a method analogous to that of Example 1 step 1.10, intermediate 69.3 replacing intermediate 1.9. The compound was purified by CC (reverse phase; eluant A: H$_2$O; eluant B: MeCN; gradient: 5 to 80% B).

LC-MS (A): t$_R$=0.96 min; [M+H]$^+$: 681.69.

Example 70

4-[2-{[6-((S)-3-Methoxy-pyrrolidin-1-yl)-2-phenyl-pyrimidine-4-carbonyl]-amino}-2-(3-phosphono-phenyl)-acetyl]-piperazine-1-carboxylic acid ethyl ester 70.1. rac-(3-Bromo-phenyl)-tert-butoxycarbonylamino-acetic acid:

This compound was prepared using a method analogous to that of Example 68 step 68.1, amino-(3-bromo-phenyl)-acetic acid replacing amino-(4-bromo-phenyl)-acetic acid.

LC-MS (A): t$_R$=0.96 min; [M+H]$^+$: 332.26.

70.2. rac-(3-Bromo-phenyl)-tert-butoxycarbonylamino-acetic acid ethyl ester:

This compound was prepared using a method analogous to that of Example 59 step 59.1, intermediate 70.1 replacing Boc-Phe(4-I)-OH. The compound was purified by CC (Hept/EA, 1/0 to 1/1).

LC-MS (A): t$_R$=1.08 min; [M+H]$^+$: 358.27.

70.3. rac-tert-Butoxycarbonylamino-[3-(diethoxy-phosphoryl)-phenyl]-acetic acid ethyl ester:

This compound was prepared using a method analogous to that of Example 68 step 68.3, intermediate 70.2 replacing intermediate 68.2.

LC-MS (A): t$_R$=0.99 min; [M+H]$^+$: 416.00.

70.4. rac-tert-Butoxycarbonylamino-[3-(diethoxy-phosphoryl)-phenyl]-acetic acid:

This compound was prepared using a method analogous to that of Example 1 step 1.2, intermediate 70.3 replacing intermediate 1.1.

LC-MS (A): t$_R$=0.89 min; [M+H]$^+$: 388.17.

70.5. rac-4-{2-tert-Butoxycarbonylamino-2-[3-(diethoxy-phosphoryl)-phenyl]-acetyl}-piperazine-1-carboxylic acid ethyl ester:

This compound was prepared using a method analogous to that of Example 56 step 56.2, 1-ethoxycarbonylpiperazine replacing intermediate 2.2, intermediate 70.4 replacing intermediate 56.1 and using DCM/THF 4/1 instead of DCM. The crude was purified by CC (EA).

LC-MS (A): $t_R$=0.95 min; [M+H]$^+$: 528.63.

70.6. rac-4-{2-Amino-2-[3-(diethoxy-phosphoryl)-phenyl]-acetyl}-piperazine-1-carboxylic acid ethyl ester, hydrochloride salt:

This compound was prepared using a method analogous to that of Example 1 step 1.4, intermediate 70.5 replacing intermediate 1.3.

LC-MS (A): $t_R$=0.70 min; [M+H]$^+$: 428.40.

70.7. 4-(2-[3-(Diethoxy-phosphoryl)-phenyl]-2-{[6-((S)-3-methoxy-pyrrolidin-1-yl)-2-phenyl-pyrimidine-4-carbonyl]-amino}-acetyl)-piperazine-1-carboxylic acid ethyl ester:

This compound was prepared using a method analogous to that of Example 56 step 56.2, intermediate 70.6 replacing intermediate 2.2, intermediate 1.8 replacing intermediate 56.1 and using DCM/THF 4/1 instead of DCM. The compound was purified by CC (eluant A: EA, eluant B: EA/MeOH 9/1, 0 to 100% B).

LC-MS (A): $t_R$=1.09 min; [M+H]$^+$: 709.80.

70.8. 4-[2-{[6-((S)-3-Methoxy-pyrrolidin-1-yl)-2-phenyl-pyrimidine-4-carbonyl]-amino}-2-(3-phosphono-phenyl)-acetyl]-piperazine-1-carboxylic acid ethyl ester:

This compound was prepared using a method analogous to that of Example 1 step 1.10, intermediate 70.7 replacing intermediate 1.9. The compound was purified by CC (reverse phase; eluant A: H$_2$O; eluant B: MeCN; gradient: 5 to 80% B).

LC-MS (A): $t_R$=0.90 min; [M+H]$^+$: 653.24.

Example 71

4-[2-{[6-((S)-3-Methoxy-pyrrolidin-1-yl)-2-phenyl-pyrimidine-4-carbonyl]-amino}-2-(3-phosphono-phenyl)-acetyl]-piperazine-1-carboxylic acid butyl ester 71.1. rac-4-{2-tert-Butoxycarbonylamino-2-[3-(diethoxy-phosphoryl)-phenyl]-acetyl}-piperazine-1-carboxylic acid butyl ester:

This compound was prepared using a method analogous to that of Example 56 step 56.2, intermediate 69.4 replacing intermediate 56.1 and using DCM/THF 4/1 instead of DCM. The crude was purified by CC (EA).

LC-MS (A): $t_R$=1.02 min; [M+H]$^+$: 556.62.

71.2. rac-4-{2-Amino-2-[3-(diethoxy-phosphoryl)-phenyl]-acetyl}-piperazine-1-carboxylic acid butyl ester, hydrochloride salt:

This compound was prepared using a method analogous to that of Example 1 step 1.4, intermediate 71.1 replacing intermediate 1.3.

LC-MS (A): $t_R$=0.77 min; [M+H]$^+$: 456.51.

71.3. 4-(-2-[3-(Diethoxy-phosphoryl)-phenyl]-2-{[6-((S)-3-methoxy-pyrrolidin-1-yl)-2-phenyl-pyrimidine-4-carbonyl]-amino}-acetyl)-piperazine-1-carboxylic acid butyl ester:

This compound was prepared using a method analogous to that of Example 56 step 56.2, intermediate 71.2 replacing intermediate 2.2, intermediate 1.8 replacing intermediate 56.1 and using DCM/THF 4/1 instead of DCM. The compound was purified by CC (First CC: eluant A: EA, eluant B: EA/MeOH 9/1, 0 to 100% B; second CC: reverse phase, eluant A: H$_2$O; eluant B: MeCN; gradient: 5 to 90% B).

LC-MS (A): $t_R$=1.15 min; [M+H]$^+$: 737.78.

71.4. 4-[2-{[6-((S)-3-Methoxy-pyrrolidin-1-yl)-2-phenyl-pyrimidine-4-carbonyl]-amino}-2-(3-phosphono-phenyl)-acetyl]-piperazine-1-carboxylic acid butyl ester:

This compound was prepared using a method analogous to that of Example 1 step 1.10, intermediate 71.3 replacing intermediate 1.9. The compound was purified by CC (reverse phase; eluant A: H$_2$O; eluant B: MeCN; gradient: 5 to 80% B).

LC-MS (A): $t_R$=0.96 min; [M+H]$^+$: 681.22.

Example 72

4-[2-{[6-((S)-3-Methoxy-pyrrolidin-1-yl)-2-phenyl-pyrimidine-4-carbonyl]-amino}-2-(2-phosphono-phenyl)-acetyl]-piperazine-1-carboxylic acid butyl ester 72.1. rac-(2-Bromo-phenyl)-tert-butoxycarbonylamino-acetic acid:

This compound was prepared using a method analogous to that of Example 68 step 68.1, amino-(2-bromo-phenyl)-acetic acid replacing amino-(4-bromo-phenyl)-acetic acid.

LC-MS (A): $t_R$=0.93 min; [M+H]$^+$: 330.21.

72.2. rac-(2-Bromo-phenyl)-tert-butoxycarbonylamino-acetic acid ethyl ester:

This compound was prepared using a method analogous to that of Example 59 step 59.1, intermediate 72.1 replacing Boc-Phe(4-I)-OH. The compound was purified twice by CC (Hept/EA, 1/0 to 0/1).

LC-MS (A): $t_R$=1.06 min; [M+H]$^+$: 358.29.

72.3. rac-tert-Butoxycarbonylamino-[2-(diethoxy-phosphoryl)-phenyl]-acetic acid ethyl ester:

This compound was prepared using a method analogous to that of Example 68 step 68.3, intermediate 72.2 replacing intermediate 68.2.

LC-MS (A): $t_R$=0.98 min; [M+H]$^+$: 416.00.

72.4. rac-tert-Butoxycarbonylamino-[2-(diethoxy-phosphoryl)-phenyl]-acetic acid:

This compound was prepared using a method analogous to that of Example 1 step 1.2, intermediate 72.3 replacing intermediate 1.1.

LC-MS (A): $t_R$=0.84 min; [M+H]$^+$: 388.02.

72.5. rac-4-{2-tert-Butoxycarbonylamino-2-[2-(diethoxy-phosphoryl)-phenyl]-acetyl}-piperazine-1-carboxylic acid butyl ester:

This compound was prepared using a method analogous to that of Example 56 step 56.2, intermediate 72.4 replacing intermediate 56.1 and using DCM/THF 4/1 instead of DCM. The crude was purified by CC (Hept/EA, 1/0 to 0/1).

LC-MS (A): $t_R$=1.01 min; [M+H]$^+$: 556.65.

72.6. rac-4-{2-Amino-2-[2-(diethoxy-phosphoryl)-phenyl]-acetyl}-piperazine-1-carboxylic acid butyl ester, hydrochloride salt:

This compound was prepared using a method analogous to that of Example 1 step 1.4, intermediate 72.5 replacing intermediate 1.3.

LC-MS (A): $t_R$=0.80 min; [M+H]$^+$: 455.21.

72.7. 4-(2-[2-(Diethoxy-phosphoryl)-phenyl]-2-{[6-((S)-3-methoxy-pyrrolidin-1-yl)-2-phenyl-pyrimidine-4-carbonyl]-amino}-acetyl)-piperazine1-carboxylic acid butyl ester:

This compound was prepared using a method analogous to that of Example 56 step 56.2, intermediate 72.6 replacing intermediate 2.2, intermediate 1.8 replacing intermediate 56.1 and using DCM/THF 4/1 instead of DCM. The compound was purified by CC (eluant A: EA, eluant B: EA/MeOH 100/1, 0 to 100% B).

LC-MS (A): $t_R$=1.11 min; [M+H]$^+$: 737.81.

72.8. 4-[2-{[6-((S)-3-Methoxy-pyrrolidin-1-yl)-2-phenyl-pyrimidine-4-carbonyl]-amino}-2-(2-phosphono-phenyl)-acetyl]-piperazine-1-carboxylic acid butyl ester:

This compound was prepared using a method analogous to that of Example 1 step 1.10, intermediate 72.7 replacing intermediate 1.9. The compound was purified by CC (reverse phase; eluant A: H$_2$O; eluant B: MeCN; gradient: 5 to 80% B).

LC-MS (A): t$_R$=1.00 min; [M+H]$^+$: 681.22.

Example 73

4-((R)-2-{[6-(4-Methyl-piperazin-1-yl)-2-phenyl-pyrimidine-4-carbonyl]-amino}-3-phosphono-propionyl)-piperazine-1-carboxylic acid butyl ester 73.1. 4-((R)-3-(Diethoxy-phosphoryl)-2-{[6-(4-methyl-piperazin-1-yl)-2-phenyl-pyrimidine-4-carbonyl]-amino}-propionyl)-piperazine-1-carboxylic acid butyl ester:

This compound was prepared using a method analogous to that of Example 1 step 1.8, 1-methylpiperazine replacing intermediate 1.7 and intermediate 14.1 replacing 6-chloro-2-phenyl-pyrimidine-4-carboxylic acid. The compound was however not purified.

LC-MS (A): t$_R$=0.82 min; [M+H]$^+$: 674.23.

73.2. 4-((R)-2-{[6-(4-Methyl-piperazin-1-yl)-2-phenyl-pyrimidine-4-carbonyl]-amino}-3-phosphono-propionyl)-piperazine-1-carboxylic acid butyl ester:

This compound was prepared using a method analogous to that of Example 1 step 1.10, intermediate 73.1 replacing intermediate 1.9. The crude was purified by CC (reverse phase; eluant A: H$_2$O; eluant B: MeCN; gradient: 5 to 80% B) followed by preparative TLC (EA/MeOH 1/1 then EA/MeOH 1/2).

LC-MS (A): t$_R$=0.70 min; [M+H]$^+$: 618.16.

Example 74

4-{(R)-2-[(6-Morpholin-4-yl-2-phenyl-pyrimidine-4-carbonyl)-amino]-3-phosphono-propionyl}-piperazine-1-carboxylic acid butyl ester 74.1. 4-{(R)-3-(Diethoxy-phosphoryl)-2-[(6-morpholin-4-yl-2-phenyl-pyrimidine-4-carbonyl)-amino]-propionyl}-piperazine-1-carboxylic acid butyl ester:

This compound was prepared using a method analogous to that of Example 1 step 1.8, morpholine replacing intermediate 1.7 and intermediate 14.1 replacing 6-chloro-2-phenyl-pyrimidine-4-carboxylic acid. The compound was however not purified.

LC-MS (A): t$_R$=1.00 min; [M+H]$^+$: 661.24.

74.2. 4-{(R)-2-[(6-Morpholin-4-yl-2-phenyl-pyrimidine-4-carbonyl)-amino]-3-phosphono-propionyl}-piperazine-1-carboxylic acid butyl ester:

This compound was prepared using a method analogous to that of Example 1 step 1.10, intermediate 74.1 replacing intermediate 1.9. The crude was purified by CC (reverse phase; eluant A: H$_2$O; eluant B: MeCN; gradient: 5 to 80% B).

LC-MS (A): t$_R$=0.84 min; [M+H]$^+$: 605.14.

Example 75

N,N'-Bis-(ethoxycarbonylmethyl)-3-{(S)-[6-((S)-3-methoxy-pyrrolidin-1-yl)-2-phenyl-pyrimidine-4-carbonyl]-amino}-4-oxo-4-(4-butoxy-carbonyl-piperazin-1-yl)-butyl-phosphonic acid diamide A mixture of intermediate 5.4 (47 mg), glycine ethyl ester hydrochloride (62 mg), TEA (0.124 ml) in anh. pyridine (0.250 ml) was heated to 60° C. for 5 min. A freshly prepared yellow solution of 2,2'-dipyridyl disulfide (115 mg) and triphenylphosphine (136 mg) in anh. pyridine (0.250 ml) was added to the above mixture. The reaction mixture was stirred at 60° C. overnight, cooled to RT and concentrated. The residue was partitioned between DCM and sat. —NaHCO$_3$. The organic phase was washed with brine, dried (Na$_2$SO$_4$) and evaporated under reduced pressure. The crude was purified by CC (solvent A: DCM, solvent B: DCM:MeOH (10:1), gradient: 0 to 100% B/12CV, 100% B/3CV) to give 19 mg of titled product as a yellowish lyophilisate after freeze-drying.

LC-MS (A): t$_R$=1.03 min; [M+H]$^+$: 802.86.

Example 76

4-((R)-3-(Bis-acetoxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 52, bromomethyl acetate replacing 1-chloroethyl pivalate.

LC-MS (A): t$_R$=1.05 min; [M+H]$^+$: 763.66

Example 77

4-((R)-3-(Bis-propionyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 52, chloromethyl propionate (prepared as described in Synth. Commun. (1995), 25(18), 2739-2749) replacing 1-chloroethyl pivalate.

LC-MS (A): t$_R$=1.06 min; [M+H]$^+$: 791.31

Example 78

4-((R)-3-(Bis-butyryloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 52, chloromethyl butyrate replacing 1-chloroethyl pivalate.

LC-MS (A): t$_R$=1.14 min; [M+H]$^+$: 819.04

Example 79

N,N'-Bis-(ethoxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide This compound was prepared using a method analogous to that of Example 75, intermediate 2.6 replacing intermediate 5.4.

LC-MS (A): t$_R$=1.02 min; [M+H]$^+$: 788.97.

Example 80

N,N'-Bis-((S)-1-ethoxycarbonylethyl)-2-{(R)-[6-
((S)-3-methoxy-pyrrolidin-1-yl)-2-phenyl-pyrimi-
dine-4-carbonyl]-amino}-3-oxo-3-(4-butoxy-carbo-
nyl-piperazin-1-yl)-propyl-phosphonic acid diamide This compound was prepared using a method analogous to that of Example 75, intermediate 2.6 replacing intermediate 5.4 and L-alanine ethyl ester hydrochloride replacing glycine ethyl ester hydrochloride.
LC-MS (A): $t_R$=1.06 min; [M+H]$^+$: 816.99.

Example 81

N,N'-Bis-(methoxycarbonylmethyl)-2-{(R)-[6-((S)-
3-methoxy-pyrrolidin-1-yl)-2-phenyl-pyrimidine-4-
carbonyl]-amino}-3-oxo-3-(4-butoxy-carbonyl-pip-
erazin-1-yl)-propyl-phosphonic acid diamide This compound was prepared using a method analogous to that of Example 75, intermediate 2.6 replacing intermediate 5.4 and glycine methyl ester hydrochloride replacing glycine ethyl ester hydrochloride.
LC-MS (A): $t_R$=0.98 min; [M+H]$^+$: 760.92.

Example 82

N,N'-Bis-((S)-1-methoxycarbonyl-2-methyl-propyl)-
2-{(R)-[6-((S)-3-methoxy-pyrrolidin-1-yl)-2-phenyl-
pyrimidine-4-carbonyl]-amino}-3-oxo-3-(4-butoxy-
carbonyl-piperazin-1-yl)-propyl-phosphonic acid
diamide This compound was prepared using a method analogous to that of Example 75, intermediate 2.6 replacing intermediate 5.4 and valine methyl ester hydrochloride replacing glycine ethyl ester hydrochloride.
LC-MS (A): $t_R$=1.11 min; [M+H]$^+$: 845.02.

Example 83

N,N'-Bis-(tert-butyloxycarbonylmethyl)-2-{(R)-[6-
((S)-3-methoxy-pyrrolidin-1-yl)-2-phenyl-pyrimi-
dine-4-carbonyl]-amino}-3-oxo-3-(4-butoxy-carbo-
nyl-piperazin-1-yl)-propyl-phosphonic acid diamide This compound was prepared using a method analogous to that of Example 75, intermediate 2.6 replacing intermediate 5.4 and glycine tert-butyl ester hydrochloride replacing glycine ethyl ester hydrochloride.
LC-MS (A): $t_R$=1.12 min; [M+H]$^+$: 845.01.

Example 84

N,N'-Bis-((S)-1-methoxycarbonylpropyl)-2-{(R)-[6-
((S)-3-methoxy-pyrrolidin-1-yl)-2-phenyl-pyrimi-
dine-4-carbonyl]-amino}-3-oxo-3-(4-butoxy-carbo-
nyl-piperazin-1-yl)-propyl-phosphonic acid diamide This compound was prepared using a method analogous to that of Example 75, intermediate 2.6 replacing intermediate 5.4 and 2-aminobutyric acid methyl ester hydrochloride replacing glycine ethyl ester hydrochloride.
LC-MS (A): $t_R$=1.07 min; [M+H]$^+$: 817.05.

Example 85

N,N'-Bis-((S)-1-methoxycarbonyl-2,2-dimethyl-
propyl)-2-{(R)-[6-((S)-3-methoxy-pyrrolidin-1-yl)-
2-phenyl-pyrimidine-4-carbonyl]-amino}-3-oxo-3-
(4-butoxy-carbonyl-piperazin-1-yl)-propyl-
phosphonic acid diamide This compound was prepared using a method analogous to that of Example 75, intermediate 2.6 replacing intermediate 5.4 and tert-leucine methyl ester hydrochloride replacing glycine ethyl ester hydrochloride.
LC-MS (A): $t_R$=1.15 min; [M+H]$^+$: 873.09.

Example 86

N,N'-Bis-((S)-1-tert-butyloxycarbonyl-ethyl)-2-{(R)-
[6-((S)-3-methoxy-pyrrolidin-1-yl)-2-phenyl-pyrimi-
dine-4-carbonyl]-amino}-3-oxo-3-(4-butoxy-carbo-
nyl-piperazin-1-yl)-propyl-phosphonic acid diamide This compound was prepared using a method analogous to that of Example 75, intermediate 2.6 replacing intermediate 5.4 and alanine tert-butyl ester hydrochloride replacing glycine ethyl ester hydrochloride.
LC-MS (A): $t_R$=1.16 min; [M+H]$^+$: 873.11.

Example 87

N,N'-Bis-((S)-1-methoxycarbonyl-2-phenyl-ethyl)-2-
{(R)-[6-((S)-3-methoxy-pyrrolidin-1-yl)-2-phenyl-
pyrimidine-4-carbonyl]-amino}-3-oxo-3-(4-butoxy-
carbonyl-piperazin-1-yl)-propyl-phosphonic acid
diamide This compound was prepared using a method analogous to that of Example 75, intermediate 2.6 replacing intermediate 5.4 and phenylalanine methyl ester hydrochloride replacing glycine ethyl ester hydrochloride.
LC-MS (A): $t_R$=1.15 min; [M+H]$^+$: 941.02.

Example 88

N,N'-Bis-((S)-1-methoxycarbonyl-1-phenyl-methyl)-
2-{(R)-[6-((S)-3-methoxy-pyrrolidin-1-yl)-2-phenyl-
pyrimidine-4-carbonyl]-amino}-3-oxo-3-(4-butoxy-
carbonyl-piperazin-1-yl)-propyl-phosphonic acid
diamide This compound was prepared using a method analogous to that of Example 75, intermediate 2.6 replacing intermediate 5.4 and phenylglycine methyl ester hydrochloride replacing glycine ethyl ester hydrochloride.
LC-MS (A): $t_R$=1.12 min; [M+H]$^+$: 913.08.

Example 89

N,N'-Bis-((S)-1-methoxycarbonyl-ethyl)-2-{(R)-[6-
((S)-3-methoxy-pyrrolidin-1-yl)-2-phenyl-pyrimi-
dine-4-carbonyl]-amino}-3-oxo-3-(4-butoxy-carbo-
nyl-piperazin-1-yl)-propyl-phosphonic acid diamide This compound was prepared using a method analogous to that of Example 75, intermediate 2.6 replacing intermediate 5.4 and alanine methyl ester hydrochloride replacing glycine ethyl ester hydrochloride.
LC-MS (A): $t_R$=1.02 min; [M+H]$^+$: 789.76.

Example 90

N,N'-Bis-(propyloxycarbonyl-methyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide This compound was prepared using a method analogous to that of Example 75, intermediate 2.6 replacing intermediate 5.4 and glycine propyl ester hydrochloride replacing glycine ethyl ester hydrochloride.

LC-MS (C): $t_R$=0.97 min; $[M+H]^+$: 817.21.

Example 91

N,N'-Bis-(isopropyloxycarbonyl-methyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide This compound was prepared using a method analogous to that of Example 75, intermediate 2.6 replacing intermediate 5.4 and glycine isopropyl ester hydrochloride replacing glycine ethyl ester hydrochloride.

LC-MS (C): $t_R$=0.97 min; $[M+H]^+$: 817.17.

Example 92

N,N'-Bis-(2-ethoxycarbonyl-prop-2-yl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide This compound was prepared using a method analogous to that of Example 75, intermediate 2.6 replacing intermediate 5.4 and α-amino isobutyric acid ethyl ester hydrochloride replacing glycine ethyl ester hydrochloride.

LC-MS (C): $t_R$=1.49 min; $[M+H]^+$: 845.21

Example 93

4-((R)-3-[Bis-(methoxycarbonyloxy-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester To a solution of intermediate 2.6 (126 mg) in anh. DMPU (0.37 mL) was added TEA (0.085 mL) and the solution was stirred for 10 min at RT. NaI (37 mg) and chloromethyl methyl carbonate (0.46 mL prepared as described in WO2004092189) were added. The mixture was stirred for 18 h at 40° C. under argon. Further amount of methyl chloromethyl carbonate (0.23 mL), TEA (0.085 mL) and NaI (31 mg) were added. The mixture was further stirred for 4 h at 40° C., cooled down to RT and diluted with toluene. The org. phase was washed with water and brine, dried ($Na_2SO_4$) and evaporated off. The crude was purified by CC (solvent A: Hept, solvent B: EA, gradient: 0 to 50% B/8CV, 50 to 100% B/16CV, 100% B/24CV) to give the title product as white powder after freeze-drying (60 mg).

LC-MS (A): $t_R$=1.07 min; $[M+H]^+$: 795.69.

Example 94

4-((R)-3-[Bis-(ethoxycarbonyloxymethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 93, chloromethyl ethyl carbonate (prepared as described in WO2004092189) replacing chloromethyl methyl carbonate.

LC-MS (A): $t_R$=1.11 min; $[M+H]^+$: 822.97.

Example 95

4-((R)-3-[Bis-(isopropoxycarbonyloxy-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 93, chloromethyl isopropyl carbonate (prepared as described in WO2004092189) replacing chloromethyl methyl carbonate.

LC-MS (A): $t_R$=1.15 min; $[M+H]^+$: 850.98.

Example 96

4-((R)-3-[Bis-(tert-butoxycarbonyloxy-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 93, tert-butyl chloromethyl carbonate (prepared as described in WO2004092189) replacing chloromethyl methyl carbonate.

LC-MS (A): $t_R$=1.18 min; $[M+H]^+$: 879.02.

Example 97

4-((R)-3-[Bis-(1-ethyloxycarbonyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 93, 1-chloroethyl ethyl carbonate replacing chloromethyl methyl carbonate and was isolated as mixture of diastereoisomers.

LC-MS (A): $t_R$=1.14 min; $[M+H]^+$: 850.98.

Example 98

4-((R)-3-[Bis-(1-isopropyloxycarbonyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 93, 1-chloroethyl isopropyl carbonate replacing chloromethyl methyl carbonate and was isolated as mixture of diastereoisomers.

LC-MS (A): $t_R$=1.18 min; $[M+H]^+$: 879.01.

Example 99

4-((R)-3-[Bis-(1-cyclohexyloxycarbonyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 93, 1-chloroethyl cyclohexyl carbonate replacing chloromethyl methyl carbonate and was isolated as mixture of diastereoisomers.

LC-MS (A): $t_R$=1.25 min; [M+H]$^+$: 959.27

Example 100

4-((R)-3-(Diphenoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester To a solution of intermediate 2.6 (100 mg), PhOH (152 mg) and PyBOP (841 mg) in anh. DMF (0.3 mL) was added DIPEA (0.22 mL) and the solution was stirred for 18 h at 45° C. under argon. A further amount of PyBOP (420 mg) and DIPEA (0.22 mL) was added and the mixture further stirred for 48 h at 45° C. DMF was evaporated off and the residue taken up in EA. The org. phase was washed with 10% aq. solution of citric acid, sat. —NaHCO$_3$ and brine, dried (Na$_2$SO$_4$) and evaporated off. The crude was purified twice by CC (1. solvent A: Hept, solvent B: EA, gradient: 10 to 100% B/12CV, 100% B/5CV then 2. solvent A: DCM, solvent B: EA, gradient: 10 to 100% B/12CV, 100% B/5CV) to give the title product as a beige foam (49 mg).

LC-MS (A): $t_R$=1.11 min; [M+H]$^+$: 771.29.

Example 101

4-((R)-3-[Bis-(5-methyl-2-oxo-[1,3]dioxol-4-yl-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester To a solution of intermediate 2.6 (100 mg), 4-hydroxymethyl-5-methyl-[1,3]dioxol-2-one (0.14 mL; prepared as described in *Synthetic Communications* (1984), 22(9), 1277-1282) and PyBOP (421 mg) in anh. DMF (0.32 mL) was added DIPEA (0.22 mL) and the solution was stirred for 18 h at 45° C. under argon. The mixture was diluted with DCM, washed with 10% aq. solution of citric acid, sat. —NaHCO$_3$ and brine, dried (Na$_2$SO$_4$) and evaporated off. The crude was purified by CC (solvent A: EA, solvent B: EA:MeOH (8:2), gradient: 10 to 100% B/15CV, 100% B/2CV; then reverse phase, solvent A: H$_2$0, solvent B: MeCN, gradient: 5 to 95% B/15CV, 95% B/2CV) to give the title product as a white powder after freeze-drying (45 mg).

LC-MS (A): $t_R$=1.07 min; [M+H]$^+$: 842.93.

Example 102

4-[(R)-2-{[6-((S)-3-Methoxy-pyrrolidin-1-yl)-2-phenyl-pyrimidine-4-carbonyl]-amino}-3-(2-oxo-4H-2λ$^5$-benzo[1,3,2]dioxaphosphinin-2-yl)-propionyl]-piperazine-1-carboxylic acid butyl ester To a solution of intermediate 2.6 (50 mg), 2-hydroxybenzyl alcohol (40 mg) and PyBOP (336 mg) in anh. DMF (0.2 mL) was added DIPEA (0.11 mL) and the solution was stirred for 2 h at 45° C. under argon. The mixture was diluted with DCM, washed with brine, dried (Na$_2$SO$_4$) and evaporated off. The crude was purified by CC (solvent A: Hept, solvent B: EA, solvent C: EA:MeOH (9:1), gradient A/B: 50 to 100% B/5CV, 100% B/5CV then gradient B/C: 0 to 100% B/10CV; followed by reverse phase, solvent A: H$_2$O, solvent B: MeCN, gradient: 5 to 95% B/15CV, 95% B/5CV) to give the title product as a white powder after freeze-drying (4 mg; mixture of diastereoisomers).

LC-MS (A): $t_R$=1.07 min; [M+H]$^+$: 706.89.

Example 103

4-[(R)-2-{[6-((S)-3-Methoxy-pyrrolidin-1-yl)-2-phenyl-pyrimidine-4-carbonyl]-amino}-3-(2-oxo-1,4-dihydro-2H-2λ$^5$-benzo[d][1,3,2]oxazaphosphinin-2-yl)-propionyl]-piperazine-1-carboxylic acid butyl ester This compound was prepared using a method analogous to that of Example 102, 2-aminobenzyl alcohol replacing 2-hydroxybenzyl alcohol and was isolated as mixture of diastereoisomers.

LC-MS (A): $t_R$=1.03/1.04 min; [M+H]$^+$: 705.97.

Example 104

4-[(R)-2-{[6-((S)-3-Methoxy-pyrrolidin-1-yl)-2-phenyl-pyrimidine-4-carbonyl]-amino}-3-(8-methyl-2-oxo-1,4-dihydro-2H-2λ$^5$-benzo[d][1,3,2]oxazaphosphinin-2-yl)-propionyl]-piperazine-1-carboxylic acid butyl ester This compound was prepared using a method analogous to that of Example 102, 2-aminobenzyl alcohol replacing 2-hydroxybenzyl alcohol and was isolated as mixture of diastereoisomers.

LC-MS (A): $t_R$=1.05/1.07 min; [M+H]$^+$: 720.04.

Example 105

4-((R)-3-[Bis-(3-oxo-1,3-dihydro-isobenzofuran-1-yloxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester To a solution of intermediate 2.6 (100 mg) in anh. NMP (0.48 mL) was added TEA (0.067 mL) and the solution was stirred for 10 min at RT. NaI (29 mg) and 3-bromophtalide (344 mg) were added. The mixture was stirred for 3 h at 65° C. under argon, cooled down to RT and diluted with toluene. The org. phase was washed with water and brine, dried (Na$_2$SO$_4$) and evaporated off. The crude was purified by CC (solvent A: Hept, solvent B: EA, gradient: 50 to 100% B/34CV, 100% B/16CV; then reverse phase, solvent A: H$_2$0, solvent B: MeCN, gradient: 5 to 95% B/12CV, 95% B/2CV) to give the title product as white powder after freeze-drying (16 mg ; mixture of diastereoisomers).

LC-MS (A): $t_R$=1.13 min; [M+H]$^+$: 883.02.

Example 106

4-((R)-3-[Bis-(ethoxycarbonyl-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 105, ethyl bromoacetate replacing 3-bromophtalide.

LC-MS (A): $t_R$=1.08 min; [M+H]$^+$: 791.04

Example 107

4-((R)-3-[Bis-((S)-1-ethoxycarbonyl-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 101, L-lactic acid ethyl ester replacing 4-hydroxymethyl-5-methyl-[1,3]dioxol-2-one.
LC-MS (A): $t_R$=1.11 min; [M+H]$^+$: 819.33.

Example 108

N-[(S)-1-Ethoxycarbonyl-ethyl]-O-phenyl-(2R)-2-{[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid amide 108.1: 4-((R)-3-(Hydroxy-phenyloxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester:

To a solution of the compound of Example 100 (518 mg) in EtOH (0.4 mL) was added a 1M-NaOH solution (0.3 mL) and the mixture was stirred for 18 h at RT. EtOH was evaporated off and the aq. residue was diluted with water and extracted twice with Et$_2$O. The aq. phase was acidified to pH 2 with a 1M HCl solution and extracted three times with DCM. The combined org. phases were dried (Na$_2$SO$_4$) and evaporated off. The crude was purified by CC (reverse phase, solvent A: H$_2$O, solvent B: MeCN, gradient: 5 to 95% B/20CV, 95% B/5CV) to give the title product as a white powder after freeze-drying (64 mg; mixture of diastereoisomers).
LC-MS (A): $t_R$=0.91 min; [M+H]$^+$: 695.40.

108.2. N-[(S)-1-Ethoxycarbonyl-ethyl]-O-phenyl-(2R)-2-{[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid amide:

This compound was prepared using a method analogous to that of Example 75, intermediate 108.1 replacing intermediate 5.4 and L-alanine ethyl ester hydrochloride (3 eq) replacing glycine ethyl ester hydrochloride (6 eq) and was isolated as mixture of diastereoisomers.
LC-MS (A): $t_R$=1.12 min; [M+H]$^+$: 794.46.

Example 109

4-[(R)-2-{[6-((S)-3-Methoxy-pyrrolidin-1-yl)-2-phenyl-pyrimidine-4-carbonyl]-amino}-3-(2-oxo-2λ$^5$-[1,3,2]dioxaphosphinan-2-yl)-propionyl]piperazine-1-carboxylic acid butyl ester This compound was prepared using a method analogous to that of Example 101, 1,3-propandiol (4 eq) replacing 4-hydroxymethyl-5-methyl-[1,3]dioxol-2-one (10 eq).
LC-MS (A): $t_R$=1.00 min; [M+H]$^+$: 659.82.

Example 110

4-[(R)-2-{[6-((S)-3-Methoxy-pyrrolidin-1-yl)-2-phenyl-pyrimidine-4-carbonyl]-amino}-3-(8-methyl-2-oxo-4H-2λ$^5$-benzo[1,3,2]dioxaphosphinin-2-yl)-propionyl]-piperazine-1-carboxylic acid butyl ester 110.1: 2-Hydroxy-3-methyl-benzoic acid methyl ester
To a solution of 2-hydroxy-3-methyl-benzoic acid (10 g) in anh. MeOH (80 mL) was added dropwise H$_2$SO$_4$ (10.8 mL). The mixture was refluxed for 24 h and partitioned between DCM and water. The org. phase was separated, dried (Na$_2$SO$_4$) and evaporated off. The crude was purified by solid phase extraction to give the title product as a yellowish liquid (9.8 g).
$^1$H-NMR (CDCl$_3$): δ=11.03 (s, 1 H), 7.71 (d, 1 H), 7.34 (d, 1 H), 6.80 (dd, 1H), 3.96 (s, 3 H), 2.29 (s, 3 H).

110.2: 2-Hydroxymethyl-6-methyl-phenol
To a solution of intermediate 110.1 (1 g) in anh. THF (5.6 mL) was added dropwise at 0° C. a 2M solution of LiAlH$_4$ in THF (5.6 mL). The mixture was stirred for 2 h at 0° C. and quenched sequentially at 0° C. by adding ice-water (0.34 mL), a 1M solution of NaOH (0.34 mL) and ice-water (1.1 mL). The suspension was stirred for 10 min, filtered over a pad of celite and the filtrate concentrated in vacuo. The crude was purified by CC (solvent A: Hept, solvent B: EA, gradient: 0 to 100% B/20CV, 100% B/2CV) to give the title product as a colourless oil (292 mg).
$^1$H-NMR (CDCl$_3$): δ=7.40 (s, 1 H), 7.12 (d, 1 H), 6.90 (d, 1 H), 6.79 (dd, 1 H), 4.87 (d, 2 H), 2.28 (s, 3 H).

110.3. 4-[(R)-2-{[6-((S)-3-Methoxy-pyrrolidin-1-yl)-2-phenyl-pyrimidine-4-carbonyl]-amino}-3-(8-methyl-2-oxo-4H-2λ$^5$-benzo[1,3,2]dioxaphosphinin-2-yl)-propionyl]-piperazine-1-carboxylic acid butyl ester This compound was prepared using a method analogous to that of Example 102, intermediate 110.2 replacing 2-hydroxybenzyl alcohol and was isolated as mixture of diastereoisomers.
LC-MS (A): $t_R$=1.09 min; [M+H]$^+$: 721.79.

Example 111

4-((R)-3-(8-Isopropyl-2-oxo-4H-2λ$^5$-benzo[1,3,2]dioxaphosphinin-2-yl)-2-{[6-((S)-3-methoxy-pyrrolidin-1-yl)-2-phenyl-pyrimidine-4-carbonyl]-amino}-propionyl)-piperazine-1-carboxylic acid butyl ester 111.1: 2-Hydroxy-3-isopropyl-benzoic acid methyl ester
This compound was prepared using a method analogous to that of Example 110, step 110.1, 2-hydroxy-3-isopropyl-benzoic acid replacing 2-hydroxy-3-methyl-benzoic acid.
$^1$H-NMR (CDCl$_3$): δ=11.14 (s, 1 H), 7.72 (d, 1 H), 7.42 (d, 1 H), 6.87 (dd, 1H), 3.97 (s, 3 H), 3.41 (m, 1H), 1.27 (d, 6 H).

111.2: 2-Hydroxymethyl-6-isopropyl-phenol
This compound was prepared using a method analogous to that of Example 110, step 110.2, intermediate 111.1 replacing intermediate 110.1.
$^1$H-NMR (CDCl$_3$): δ=7.50 (s, 1 H), 7.21 (d, 1 H), 6.88 (m, 2 H), 4.89 (d, 2 H), 3.37 (m, 1 H), 1.28 (d, 6 H).

111.3. 4-((R)-3-(8-Isopropyl-2-oxo-4H-2λ$^5$-benzo[1,3,2]dioxaphosphinin-2-yl)-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 102, intermediate 111.2 replacing 2-hydroxybenzyl alcohol and was isolated as mixture of diastereoisomers.
LC-MS (A): $t_R$=1.13 min; [M+H]$^+$: 749.78.

Example 112

4-((R)-3-(8-Methoxy-2-oxo-1,4-dihydro-2H-2λ$^5$-benzo[d][1,3,2]oxazaphosphinin-2-yl)-2-{[6-((S)-3-methoxy-pyrrolidin-1-yl)-2-phenyl-pyrimidine-4-carbonyl]-amino}-propionyl)-piperazine-1-carboxylic acid butyl ester 112.1: 2-Amino-3-methoxy-benzoic acid methyl ester
This compound was prepared using a method analogous to that of Example 110, step 110.1, 2-amino-3-methoxy-benzoic acid replacing 2-hydroxy-3-methyl-benzoic acid.
LC-MS (A): $t_R$=0.92 min; [M+H]$^+$: 182.48.

112.2: (2-Amino-3-methoxy-phenyl)-methanol

This compound was prepared using a method analogous to that of Example 110, step 110.2, intermediate 112.1 replacing intermediate 110.1.

LC-MS (A): $t_R$=0.36 min; [M+H]$^+$: 154.16.

112.3. 4-((R)-3-(8-Methoxy-2-oxo-1,4-dihydro-2H-2λ$^5$-benzo[d][1,3,2]oxazaphosphinin-2-yl)-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 102, intermediate 112.2 replacing 2-hydroxybenzyl alcohol and was isolated as mixture of diastereoisomers.

LC-MS (A): $t_R$=1.04/1.07 min; [M+H]$^+$: 736.41.

Example 113

4-((R)-3-[(5-tert-Butyl-2-oxo-[1,3]dioxol-4-yl-methoxy)-hydroxy-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 101, 4-hydroxymethyl-5-tert-butyl-[1,3]dioxol-2-one (prepared as described in *Tetrahedron Letters* (2002), 43, 1161-1164) replacing 4-hydroxymethyl-5-methyl-[1,3]dioxol-2-one. Only the monoester was isolated as mixture of diastereoisomers.

LC-MS (A): $t_R$=0.98 min; [M+H]$^+$: 773.92.

Example 114

4-((R)-3-(Bis-benzyloxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 101, benzyl alcohol replacing 4-hydroxymethyl-5-methyl[1,3]dioxol-2-one.

LC-MS (A): $t_R$=1.15 min; [M+H]$^+$: 799.22.

Example 115

4-((R)-3-(Acetoxymethoxy-hydroxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester 115.1: 4-((R)-3-(Benzyloxy-hydroxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 75, intermediate 2.6 replacing intermediate 5.4 and benzyl alcohol (3 eq) replacing glycine ethyl ester hydrochloride (6 eq) and was isolated as mixture of diastereoisomers.

LC-MS (A): $t_R$=0.97 min; [M+H]$^+$: 709.45.

115.2. 4-((R)-3-(Acetoxymethoxy-hydroxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester This compound was prepared using a method analogous to that of Example 52, bromomethyl acetate replacing 1-chloroethyl pivalate, intermediate 115.1 replacing intermediate 2.6 and the mixture was stirred on at 45° C. and was isolated as mixture of diastereoisomers.

LC-MS (A): $t_R$=0.89 min; [M+H]$^+$: 691.19

Example 116

4-((S)-3-[Bis-(acetoxy-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid ethyl ester This compound was prepared using a method analogous to that of Example 52, intermediate 3.6 replacing intermediate 2.6 and bromomethyl acetate replacing 1-chloroethyl pivalate.

LC-MS (A): $t_R$=0.99 min; [M+H]$^+$: 735.62

Example 117

4-((S)-3-[Bis-(butyryloxy-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid ethyl ester This compound was prepared using a method analogous to that of Example 52, intermediate 3.6 replacing intermediate 2.6 and chloromethyl butyrate replacing 1-chloroethyl pivalate.

LC-MS (A): $t_R$=1.10 min; [M+H]$^+$: 791.64

Example 118

N,N'-Bis-((S)-1-ethoxycarbonylethyl)-2-{(S)-[6-((S)-3-methoxy-pyrrolidin-1-yl)-2-phenyl-pyrimidine-4-carbonyl]-amino}-3-oxo-3-(4-ethoxy-carbonyl-piperazin-1-yl)-propyl-phosphonic acid diamide This compound was prepared using a method analogous to that of Example 75, intermediate 3.6 replacing intermediate 5.4 and L-alanine ethyl ester hydrochloride replacing glycine ethyl ester hydrochloride.

LC-MS (A): $t_R$=1.02 min; [M+H]$^+$: 789.84.

Example 119

4-((S)-3-[Bis-(ethoxycarbonyloxy-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid ethyl ester This compound was prepared using a method analogous to that of Example 93, intermediate 3.6 replacing intermediate 2.6 and chloromethyl ethyl carbonate replacing methyl chloromethyl carbonate.

LC-MS (A): $t_R$=1.06 min; [M+H]$^+$: 795.68.

Example 120

4-((R)-3-[Bis-(acetoxy-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid ethyl ester This compound was prepared using a method analogous to that of Example 52, intermediate 1.10 replacing intermediate 2.6 and bromomethyl acetate replacing 1-chloroethyl pivalate.

LC-MS (A): $t_R$=1.00 min; [M+H]$^+$: 735.64

Example 121

4-((R)-3-[Bis-(butyryloxy-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid ethyl ester This compound was prepared using a method analogous to that of Example 52, intermediate 1.10 replacing intermediate 2.6 and chloromethyl butyrate replacing 1-chloroethyl pivalate.
LC-MS (A): $t_R$=1.10 min; [M+H]$^+$: 791.59

Example 122

N,N'-Bis-((S)-1-ethoxycarbonylethyl)-2-{(R)-[6-((S)-3-methoxy-pyrrolidin-1-yl)-2-phenyl-pyrimidine-4-carbonyl]-amino}-3-oxo-3-(4-ethoxy-carbonyl-piperazin-1-yl)-propyl-phosphonic acid diamide This compound was prepared using a method analogous to that of Example 75, intermediate 1.10 replacing intermediate 5.4 and L-alanine ethyl ester hydrochloride replacing glycine ethyl ester hydrochloride.
LC-MS (A): $t_R$=1.01 min; [M+H]$^+$: 789.92

Example 123

4-((R)-3-[Bis-(ethoxycarbonyloxy-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid ethyl ester This compound was prepared using a method analogous to that of Example 93, intermediate 1.10 replacing intermediate 2.6 and chloromethyl ethyl carbonate replacing chloromethyl methyl carbonate.
LC-MS (A): $t_R$=1.06 min; [M+H]$^+$: 795.68

Example 124

4-((S)-3-[4-(Bis-(butyryloxy-methoxy)-phosphoryl)-phenyl]-2-{[6-((S)-3-methoxy-pyrrolidin-1-yl)-2-phenyl-pyrimidine-4-carbonyl]-amino}-propionyl)-piperazine-1-carboxylic acid ethyl ester This compound was prepared using a method analogous to that of Example 52, intermediate 59.7 replacing intermediate 2.6 and chloromethyl butyrate replacing 1-chloroethyl pivalate.
LC-MS (A): $t_R$=1.14 min; [M+H]$^+$: 867.40

Example 125

N,N'-Bis-((S)-1-ethoxycarbonylethyl)-4-[2-{(S)-[6-((S)-3-methoxy-pyrrolidin-1-yl)-2-phenyl-pyrimidine-4-carbonyl]-amino}-3-oxo-3-(4-ethoxy-carbonyl-piperazin-1-yl)-propyl]-phenyl-phosphonic acid diamide This compound was prepared using a method analogous to that of Example 75, intermediate 59.7 replacing intermediate 5.4 and L-alanine ethyl ester hydrochloride replacing glycine ethyl ester hydrochloride.
LC-MS (A): $t_R$=1.04 min; [M+H]$^+$: 865.36

Example 126

4-((S)-3-[4-(Bis-(ethoxycarbonyloxy-methoxy)-phosphoryl)-phenyl]-2-{[6-((S)-3-methoxy-pyrrolidin-1-yl)-2-phenyl-pyrimidine-4-carbonyl]-amino}-propionyl)-piperazine-1-carboxylic acid ethyl ester This compound was prepared using a method analogous to that of Example 93, intermediate 59.7 replacing intermediate 2.6 and chloromethyl ethyl carbonate replacing chloromethyl methyl carbonate.
LC-MS (A): $t_R$=1.06 min; [M+H]$^+$: 871.47

BIOLOGICAL TESTS

P2Y$_{12}$ Receptor Binding Assay
Procedure

Chinese Hamster Ovary (CHO) cells with recombinant expression of the human P2Y$_{12}$ receptor were cultured in 24 well cell-culture plates. Cells were washed three times with binding buffer (50 mM Tris pH 7.4, 100 mM NaCl, mM EDTA, 0.5% BSA). The cells were then incubated with 0.5 ml per well binding buffer containing tritium-labeled 2-methyl-thio-adenosine 5'-diphosphate (2-methyl-S-ADP) (between 100,000 and 300,000 dpm per well) and various concentrations of test compounds. After incubation at RT for 2 hours, cells were washed three times with binding buffer. Then, cells were solubilized by addition of 0.5 ml solubilization buffer (SDS, NaOH, EDTA). The content of each well was then transferred into beta-counter vials and 2.0 ml of Ultima Gold Scintillation liquid was added. After quantification of the cell-associated signal, extent of inhibition was calculated relative to maximal possible inhibition demonstrated by addition of excess of cold 2-methyl-S-ADP.

Results Obtained for the Compounds of Formula I

Using the procedure described above for the P2Y$_{12}$ receptor binding assay, IC$_{50}$ values ranging from 1.3 nM to 888 nM, with an arithmetic mean value of about 37 nM (geometric mean value of about 10 nM), were measured for the example compounds corresponding to formula I (R$^5$=R$^8$=OH), i.e. the compounds of Examples 1 to 47 and 56 to 74.

For example, the following results could be obtained for the Example compounds of formula I (R$^5$=R$^8$=OH) using the procedure described above for the P2Y$_{12}$ receptor binding assay:

| Example No. | IC$_{50}$ at P2Y$_{12}$ receptor binding assay (nM) |
|---|---|
| 7 | 3.2 |
| 12 | 5.9 |
| 16 | 4.5 |
| 21 | 78 |
| 34 | 13 |
| 35 | 14 |
| 37 | 78 |
| 38 | 61 |
| 45 | 5.5 |
| 56 | 162 |
| 61 | 7.5 |
| 63 | 69 |
| 67 | 13 |
| 71 | 4.5 |
| 73 | 3.0 |

Compounds of formula I, wherein at least one of the substituents R$^5$ or R$^8$ is not hydroxy are expected to be cleaved under physiological conditions to the respective compounds of formula I, wherein $R^5$ and $R^8$ are both represented by hydroxy (see below). For these compounds (examples 48-55 and 75-126), the procedure described above for the $P2Y_{12}$ receptor binding assay resulted in $IC_{50}$ values ranging from 2.1 nM to 4601 nM, with an arithmetic mean value of about 270 nM (geometric mean value of about 47 nM). $IC_{50}$ values of selected examples are given in the following table:

| Example No. | $IC_{50}$ at $P2Y_{12}$ receptor binding assay (nM) |
|---|---|
| 48 | 49 |
| 75 | 308 |
| 78 | 7 |
| 87 | 11 |
| 88 | 22 |
| 89 | 162 |
| 92 | 42 |
| 93 | 3.5 |
| 95 | 34 |
| 101 | 3.2 |
| 103 | 3.1 |
| 107 | 153 |
| 109 | 208 |
| 110 | 2.8 |
| 115 | 5.0 |
| 120 | 7.0 |
| 124 | 36 |

Pharmacokinetics in Rats

Principle

In view of their structure, the compounds of formula I, wherein at least one of the substituents $R^5$ or $R^8$ is not represented by hydroxy, are expected to be rapidly converted into the corresponding acid derivatives of formula I ($R^5=R^8=$OH) when they are submitted to physiological conditions. The following pharmacokinetic assays in rats are designed to show this conversion.

Procedure (Assay 1)

Rats were delivered from RCC Ltd, Biotechnology and Animal Breeding Division, Füllinsdorf, Switzerland, and used for pharmacokinetic experiments after an acclimatization period of at least 7 days. All animals were housed under conditions in accordance with the NIH guidelines and as approved by the cantonal veterinary office (license no. 169). Two days prior to an intravenous dosing, rats were anesthetized with isoflurane. A catheter was implanted into the jugular vein under aseptic conditions to allow for multiple blood sampling. After recovery from general anesthesia, animals were housed individually under standard laboratory conditions in Makrolon type-3 cages with wire mesh tops and standardized softwood bedding.

The compound of formula I ($R^5$ and/or $R^8 \neq$OH) to be tested is administered intravenously to two male Wistar rats (body weights of 200 to 220 g) as a clear solution of 1 mg/mL in water with PEG400 (7.5%), PG (7.5%) and Cremophor-EL® (5%). The rats received a dose of 1 mg/kg. 20 min after the intravenous administration, a blood sample was taken from the two rats, and the concentration of corresponding compound of formula I ($R^5=R^8=$OH) was quantified by LC-MS-MS.

Results Obtained for a Compound of Formula I

The following results were obtained in rats following the administration of the compound of Example 48 pursuant to the procedure described above:

| Rat | Rat No. 1 | Rat No. 2 |
|---|---|---|
| Concentration of compound of Example 5 found 20 min post intravenous administration (ng/mL) | 69.9 | 60.7 |

These results show that the compound of Example 48, when administered to rats, is rapidly converted in vivo into the compound of Example 5 (the corresponding compound of formula I with $R^5=R^8=$OH).

Procedure (Assay 2)

The compound of formula I ($R^5$ and/or $R^8 \neq$OH) to be tested is administered orally to three male Wistar rats (body weights of 200 to 220 g) as a clear solution of 2 mg/mL in water with PEG400 (7.5%), PG (7.5%) and Cremophor-EL® (5%). The rats received a dose of 5 mL/kg. 5 h after the oral administration, a blood sample was taken sublingually under isoflurane anesthesia from the three rats, and the concentration of corresponding compound of formula I ($R^5=R^8=$OH) was quantified by LC-MS-MS.

Results Obtained for Compounds of Formula I

The following results were obtained in rats following the oral administration of the respective compound pursuant to the procedure described above:

| Administered compound of formula I ($R^5$ and/or $R^8 \neq$ OH) | compound of formula I ($R^5=R^8=$ OH) measured | Concentration of measured compound found 5 h post oral administration to rat (ng/mL) |
|---|---|---|
| Example 48 | Example 5 | 12 |
| Example 78 | Example 2 | 351 |
| Example 88 | Example 2 | 53 |
| Example 93 | Example 2 | 322 |
| Example 101 | Example 2 | 29 |
| Example 109 | Example 2 | 6 |
| Example 122 | Example 1 | 24 |

These results show that the tested compounds, when administered to rats, are converted in vivo into the corresponding compounds of formula I with $R^5=R^8=$OH.

Light Transmission Platelet Aggregation Assay

Procedure

Preparation of Platelet-Rich Plasma (PRP)

After obtaining informed consent, blood was obtained by vein puncture from healthy volunteers using a thrombin inhibitor as the anticoagulant. Platelet-rich plasma (PRP) was removed after centrifugation at 20° C. for 10 minutes at 200 g and allowed to equilibrate at 37° C. Part of the blood was centrifuged for 10 minutes at 5000 g to yield platelet poor plasma (PPP).

ADP Induced Platelet Aggregation

Light transmission platelet aggregation was carried out according to the method of Born & Cross (G. V. R. Born and M. J. Cross, *J. Physiol.* (1963), 168, 178-195) using a Chronolog lumiaggregometer with stirring (1000 rpm) at 37° C. PRP was placed into the cuvette and allowed to equilibrate at 37° C. for two minutes. In a first phase, the ADP concentration to give optimal extent of aggregation was determined for the PRP of each donor. In a second phase, PRP was incubated with inhibitors for 2 minutes at 37° C. prior to the addition of the agonist ADP at 1-5 μM final concentration. The change in light transmission, indicative of ongoing aggregation, was monitored during 5 minutes. The extent of platelet aggregation was calculated relative to light absorbance of PRP (not aggregated) and PPP (full aggregation).

Comparative Test Results

The following results have been obtained using the light transmission platelet aggregation assay as described above:

| compound falling within the general formula I of WO 2006/114774] | IC₅₀ (nM) | compound of formula I (Example N°) | IC₅₀ (nM) |
| --- | --- | --- | --- |
| (structure) | 21 | (example 5) | 1 |
| (structure) (formate salt) | 32 | (example 4) | 21 |
| (structure) | 91 | (example 2) | 8 |
| (structure) | 226 | (example 59) | 4 |

-continued

| compound falling within the general formula I of WO 2006/114774] | IC$_{50}$ (nM) | compound of formula I (Example N°) | IC$_{50}$ (nM) |
|---|---|---|---|
| | 138 | | 10 |

(example 1)

The invention claimed is:

1. A compound of formula I

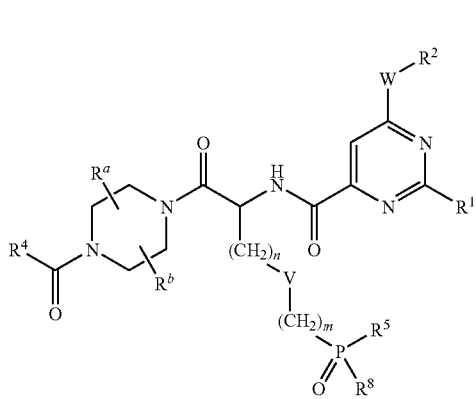

formula I wherein

R$^1$ represents phenyl, wherein the phenyl is unsubstituted or substituted 1 to 3 times by substituents each independently selected from the group consisting of halogen, methyl, methoxy, trifluoromethyl and trifluoromethoxy;

W represents a bond, and R$^2$ represents alkyl, hydroxyalkyl, alkoxyalkyl, cycloalkyl, aryl or heteroaryl; or W represents —O— and R$^2$ represents alkyl, cycloalkyl, hydroxyalkyl or heterocyclyl; or W represents —NR$^3$—, R$^2$ represents alkyl, alkoxycarbonylalkyl, carboxyalkyl, hydroxyalkyl, alkoxyalkyl, heterocyclyl, cycloalkyl, aryl or aralkyl and R$^3$ represents hydrogen or alkyl; or W represents —NR$^3$— and R$^2$ and R$^3$ form, together with the nitrogen that carries them, a heterocyclic ring of 4 to 7 members wherein the members needed to complete said heterocyclic ring are each independently selected from —CH$_2$—, —CHR$^x$—, —O—, —S—, —CO— and —NR$^y$—, it being understood however that said heterocyclic ring does not contain more than one member selected from the group consisting of —CHR$^x$—, —O—, —S—, —CO— and —NR$^y$—, R$^x$ representing hydroxy, hydroxymethyl, alkoxymethyl or alkoxy and R$^y$ representing hydrogen or alkyl;

or W represents —NR$^3$— and R$^2$ and R$^3$ form, together with the nitrogen that carries them, an imidazolyl, pyrazolyl, 1,2,3-triazolyl or 1,2,4-triazolyl ring, which ring may be substituted by an alkyl group;

R$^a$ represents hydrogen or methyl;
R$^b$ represents hydrogen or methyl;
R$^4$ represents alkoxy;
n represents 0, 1, 2 or 3, V represents a bond, and m represents 0; or
n represents 0 or 1, V represents phenyl, and m represents 0; or
n represents 1, V represents phenyl, and m represents 1;
R$^5$ and R$^8$ are identical and represent each hydroxy, unsubstituted phenyloxy, unsubstituted benzyloxy, a group —O—(CHR$^6$)—O—C(=O)—R$^7$, a group —O—(CHR$^6$)—O—C(=O)—O—R$^7$, a group —O—(CHR$^6$)—C(=O)—O—R$^9$, a group —NH-(CHR$^{10}$)—C(=O)—O—R$^9$ or a group —NH—C(CH$_3$)$_2$—C(=O)—O—R$^9$; or P(O)R$^5$R$^8$ represents a group selected from the following structures

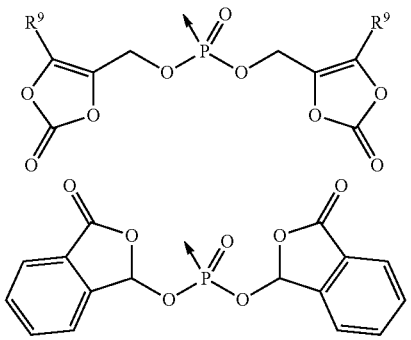

wherein the arrow marks the point of attachment to the remaining part of compounds of formula I;
R$^6$ represents hydrogen or (C$_1$-C$_3$)alkyl;
R$^7$ represents (C$_1$-C$_4$)alkyl or unsubstituted (C$_3$-C$_6$)cycloalkyl;
R$^9$ represents (C$_1$-C$_4$)alkyl;
R$^{10}$ represents hydrogen, (C$_1$-C$_4$)alkyl, unsubstituted phenyl or unsubstituted benzyl;

or a pharmaceutically acceptable salt thereof.

2. A compound of formula I according to claim 1, wherein V represents a bond or a pharmaceutically acceptable salt thereof.

3. A compound of formula I according to claim 1, wherein V represents phenyl;
or a pharmaceutically acceptable salt thereof.

4. A compound of formula I according to claim 1, wherein, when V represents a bond, then m represents 0 and n represents 1, 2 or 3;

or a pharmaceutically acceptable salt thereof.

5. A compound of formula I according to claim 1, wherein $R^1$ represents unsubstituted phenyl;
or a pharmaceutically acceptable salt thereof.

6. A compound of formula I according to claim 1, wherein W represents a bond;
or a pharmaceutically acceptable salt thereof.

7. A compound of formula I according to claim 1, wherein W represents —O—;
or a pharmaceutically acceptable salt thereof.

8. A compound of formula I according to claim 1, wherein W represents —$NR^3$—, $R^2$ represents alkyl, alkoxycarbonylalkyl, carboxyalkyl, hydroxyalkyl, alkoxyalkyl, heterocyclyl, cycloalkyl, phenyl or phenylalkyl and $R^3$ represents hydrogen or alkyl; or wherein W represents —$NR^3$— and $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O— and —$NR^y$—, it being understood however that said heterocyclic ring does not contain more than one member selected from the group consisting of —$CHR^x$—, —O— and —$NR^y$—, $R^x$ representing hydroxy, hydroxymethyl, alkoxymethyl or alkoxy and $R^y$ representing alkyl or wherein W represents —$NR^3$— and $R^2$ and $R^3$ form, together with the nitrogen that carries them, a pyrazolyl ring which may be unsubstituted or monosubstituted by an alkyl group;
or a pharmaceutically acceptable salt thereof.

9. A compound of formula I according to claim 1, wherein $R^4$ represents ($C_2$-$C_4$)alkoxy;
or a pharmaceutically acceptable salt thereof.

10. A compound of formula I according to claim 1, wherein $R^5$ and $R^8$ are identical and represent hydroxy;
or a pharmaceutically acceptable salt thereof.

11. A compound of formula I according to claim 1, which is selected from the group consisting of:
  4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid ethyl ester;
  4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester;
  4((S)-2-{[6-((S)-3-methoxy-pyrrolidin-1-yl)-2-phenyl-pyrimidine-4-carbonyl]-amino}-3-phosphono-propionyl)-piperazine-1-carboxylic acid ethyl ester;
  4((S)-2-{[6-((S)-3-methoxy-pyrrolidin-1-yl)-2-phenyl-pyrimidine-4-carbonyl]-amino}-4-phosphono-butyryl)-piperazine-1-carboxylic acid ethyl ester;
  4((S)-2-{[6-((S)-3-methoxy-pyrrolidin-1-yl)-2-phenyl-pyrimidine-4-carbonyl]-amino}-4-phosphono-butyryl)-piperazine-1-carboxylic acid butyl ester;
  4((S)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester;
  4- {(S)-2-[(2-phenyl-6-pyrazol-1-yl-pyrimidine-4-carbonyl)-amino]-4-phosphono-butyryl}-piperazine-1-carboxylic acid butyl ester;
  4((S)-2-{[6-(4-methyl-pyrazol-1-yl)-2-phenyl-pyrimidine-4-carbonyl]-amino}-4-phosphono-butyryl) -piperazine-1-carboxylic acid butyl ester;
  4-[(S)-2-({2-phenyl-6-[(S)-(tetrahydro-furan-3-yl)oxy]-pyrimidine-4-carbonyl}-amino)-4-phosphono-butyryl]-piperazine-1-carboxylic acid butyl ester;
  4-{(S)-2-[(2-phenyl-6-pyrrolidin-1-yl-pyrimidine-4-carbonyl)-amino]-4-phosphono-butyryl}-piperazine-1-carboxylic acid butyl ester;
  4-{(S)-2-[(6-isopropylamino-2-phenyl-pyrimidine-4-carbonyl)-amino]-4-phosphono-butyryl}-piperazine-1-carboxylic acid butyl ester;
  4-{(S)-2-[(6-morpholin-4-yl-2-phenyl-pyrimidine-4-carbonyl)-amino]-4-phosphono-butyryl}-piperazine-1-carboxylic acid butyl ester;
  4((S)-2-{[6-(4-methyl-piperazin-1-yl)-2-phenyl-pyrimidine-4-carbonyl]-amino}-4-phosphono-butyryl) -piperazine-1-carboxylic acid butyl ester;
  4-{(R)-2-[(6-methylamino-2-phenyl-pyrimidine-4-carbonyl)-amino]-3-phosphono-propionyl}-piperazine-1-carboxylic acid butyl ester;
  4-{(R)-2-[(6-dimethylamino-2-phenyl-pyrimidine-4-carbonyl)-amino]-3-phosphono-propionyl}-piperazine-1-carboxylic acid butyl ester;
  4-{(R)-2-[(6-ethylamino-2-phenyl-pyrimidine-4-carbonyl)-amino]-3-phosphono-propionyl}-piperazine-1-carboxylic acid butyl ester;
  4-{(R)-2-[(6-isopropylamino-2-phenyl-pyrimidine-4-carbonyl)-amino]-3-phosphono-propionyl}-piperazine-1-carboxylic acid butyl ester;
  4((S)-2-{[2-(4-fluoro-phenyl)-6-(S)-3-methoxy-pyrrolidin-1-yl)-pyrimidine-4-carbonyl]-amino}-4-phosphono-butyryl)-piperazine-1-carboxylic acid butyl ester;
  4((S)-2-{[6-((S)-3-methoxy-pyrrolidin-1-yl)-2-p-tolyl-pyrimidine-4-carbonyl]-amino}-4-phosphono-butyryl)-piperazine-1-carboxylic acid butyl ester;
  4((S)-2-{[2-(2-fluoro-phenyl)-6-(S)-3-methoxy-pyrrolidin-1-yl)-pyrimidine-4-carbonyl]-amino}-4-phosphono-butyryl)-piperazine-1-carboxylic acid butyl ester;
  4((S)-2-{[2-(3-fluoro-phenyl)-6-(S)-3-methoxy-pyrrolidin-1-yl)-pyrimidine-4-carbonyl]-amino}-4-phosphono-butyryl)-piperazine-1-carboxylic acid butyl ester;
  4-{(R)-2-[(6-methoxy-2-phenyl-pyrimidine-4-carbonyl)-amino]-3-phosphono-propionyl}-piperazine-1-carboxylic acid butyl ester;
  4-{(R)-2-[(6-methyl-2-phenyl-pyrimidine-4-carbonyl)-amino]-3-phosphono-propionyl}-piperazine-1-carboxylic acid butyl ester;
  4-{(R)-2-[(6-cyclopropylamino-2-phenyl-pyrimidine-4-carbonyl)-amino]-3-phosphono-propionyl}-piperazine-1-carboxylic acid butyl ester;
  4-{(R)-2-[(2-phenyl-6-phenylamino-pyrimidine-4-carbonyl)-amino]-3-phosphono-propionyl}-piperazine-1-carboxylic acid butyl ester;
  4-{(R)-2-[(6-benzylamino-2-phenyl-pyrimidine-4-carbonyl)-amino]-3-phosphono-propionyl}-piperazine-1-carboxylic acid butyl ester;
  4-[(R)-2-({2-phenyl-6-[(R)-(tetrahydro-furan-3-yl) amino]-pyrimidine-4-carbonyl}-amino)-3-phosphono-propionyl]-piperazine-1-carboxylic acid butyl ester;
  4-((R)-2-{[6-(3-hydroxy-pyrrolidin-1-yl)-2-phenyl-pyrimidine-4-carbonyl]-amino}-3-phosphono-propionyl)-piperazine-1-carboxylic acid butyl ester;
  4-[(R)-2-({6-[(2-methoxy-ethyl)-methyl-amino]-2-phenyl-pyrimidine-4-carbonyl}-amino)-3-phosphono-propionyl]-piperazine-1-carboxylic acid butyl ester;
  4-((R)-2-{[6-(2-ethoxycarbonyl-ethylamino)-2-phenyl-pyrimidine-4-carbonyl]-amino}-3-phosphono-propionyl)-piperazine-1-carboxylic acid butyl ester;
  4-((R)-2-{[6-(2-carboxy-ethylamino)-2-phenyl-pyrimidine-4-carbonyl]-amino}-3-phosphono-propionyl) -piperazine-1-carboxylic acid butyl ester;

4-{(R)-2-[(2,6-diphenyl-pyrimidine-4-carbonyl)-amino]-3-phosphono-propionyl}-piperazine-1-carboxylic acid butyl ester;

4-{(R)-2-[(2-phenyl-6-thiophen-3-yl-pyrimidine-4-carbonyl)-amino]-3-phosphono-propionyl}-piperazine-1-carboxylic acid butyl ester;

4-((R)-2-{[6-(4-methoxy-phenyl)-2-phenyl-pyrimidine-4-carbonyl]-amino}-3-phosphono-propionyl) -piperazine-1-carboxylic acid butyl ester;

4-{(R)-2-[(6-cyclopropyl-2-phenyl-pyrimidine-4-carbonyl)-amino]-3-phosphono-propionyl}-piperazine-1-carboxylic acid butyl ester;

4-{(R)-2-[(6-butyl-2-phenyl-pyrimidine-4-carbonyl)-amino]-3-phosphono-propionyl}-piperazine-1-carboxylic acid butyl ester;

4-[(R)-2-({2-phenyl-6-[(S)-(tetrahydro-furan-3-yl)oxy]-pyrimidine-4-carbonyl}-amino)-3-phosphono-propionyl]-piperazine-1-carboxylic acid butyl ester;

4-((R)-2-{[6-((S)-3-methoxy-pyrrolidin-1-yl)-2-phenyl-pyrimidine-4-carbonyl]-amino}-3-phosphono-propionyl)-2-methyl-piperazine-1-carboxylic acid ethyl ester;

4-((R)-2-{[6-((S)-3-methoxy-pyrrolidin-1-yl)-2-phenyl-pyrimidine-4-carbonyl]-amino}-4-phosphono-butyryl)-piperazine-1-carboxylic acid ethyl ester;

4-((R)-2-{[6-((S)-3-methoxy-pyrrolidin-1-yl)-2-phenyl-pyrimidine-4-carbonyl]-amino}-4-phosphono-butyryl)-piperazine-1-carboxylic acid butyl ester;

4-((R)-2-{[6-((1S,2S)-2-methoxymethyl-cyclopropyl)-2-phenyl-pyrimidine-4-carbonyl]-amino}-3-phosphono-propionyl)-piperazine-1-carboxylic acid butyl ester;

4-((R)-2-{[6-((1S,2S)-2-hydroxymethyl-cyclopropyl)-2-phenyl-pyrimidine-4-carbonyl]-amino}-3-phosphono-propionyl)-piperazine-1-carboxylic acid butyl ester;

4-((R)-2-{[6-(2-hydroxy-ethylamino)-2-phenyl-pyrimidine-4-carbonyl]-amino}-3-phosphono-propionyl) -piperazine-1-carboxylic acid butyl ester;

4-((R)-2-{[6-(2-hydroxymethyl-piperidin-1-yl)-2-phenyl-pyrimidine-4-carbonyl]-amino}-3-phosphono-propionyl)-piperazine-1-carboxylic acid butyl ester;

4-((R)-2-{[6-(3-methoxy-propyl)-2-phenyl-pyrimidine-4-carbonyl]-amino}-3-phosphono-propionyl) -piperazine-1-carboxylic acid butyl ester;

4-((R)-2-{[6-(3-hydroxy-butyl)-2-phenyl-pyrimidine-4-carbonyl]-amino}-3-phosphono-propionyl) -piperazine-1-carboxylic acid butyl ester;

4((S)-2-{[6-((S)-3-methoxy-pyrrolidin-1-yl)-2-(3-trifluoromethyl-phenyl)-pyrimidine-4-carbonyl]-amino}-4-phosphono-butyryl)-piperazine-1-carboxylic acid butyl ester;

4((S)-4-[bis-(2,2-dimethyl-propionyloxymethoxy)-phosphoryl]-2-{[6-((S)-3-methoxy-pyrrolidin-1-yl)-2-phenyl-pyrimidine-4-carbonyl]-amino}-butyryl)-piperazine-1-carboxylic acid butyl ester;

4-((S)-4-(bis-isobutyryloxymethoxy-phosphoryl)-2-{[6-((S)-3-methoxy-pyrrolidin-1-yl)-2-phenyl-pyrimidine-4-carbonyl]-amino}-butyryl)-piperazine-1-carboxylic acid butyl ester;

4((S)-4-{bis-[(2,2-dimethyl-propionyloxy)-ethoxy]-phosphoryl}-2-{[6-((S)-3-methoxy-pyrrolidin-1-yl)-2-phenyl-pyrimidine-4-carbonyl]-amino}-butyryl)-piperazine-1-carboxylic acid butyl ester;

4(R)-3-[bis-(2,2-dimethyl-propionyloxymethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-{bis-[1-(2,2-dimethyl-propionyloxy)-ethoxy]-phosphoryl}-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[bis-(1-isobutyryloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[bis-(1-propionyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4(R)-3-(bis-isobutyryloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester; and 4-(2-{[6-((S)-3-methoxy-pyrrolidin-1-yl)-2-phenyl-pyrimidine-4-carbonyl]-amino}-2-phosphono-acetyl)-piperazine-1-carboxylic acid butyl ester;

or a pharmaceutically acceptable salt thereof.

12. A compound of formula I according to claim 1, which is selected from the group consisting of:

4-((R)-2-{[6-(2-Hydroxy-ethoxy)-2-phenyl-pyrimidine-4-carbonyl]-amino}-3-phosphono-propionyl)-piperazine-1-carboxylic acid butyl ester;

4-((S)-2-{[6-((S)-3-Methoxy-pyrrolidin-1-yl)-2-phenyl-pyrimidine-4-carbonyl]-amino}-5-phosphono-pentanoyl)-piperazine-1-carboxylic acid butyl ester;

4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid ethyl ester;

4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid butyl ester;

4-[(S)-2-{[6-((S)-3-Methoxy-pyrrolidin-1-yl)-2-phenyl-pyrimidine-4-carbonyl]-amino}-3-(4-phosphonomethyl-phenyl)-propionyl]-piperazine-1-carboxylic acid ethyl ester;

4-[(S)-2-{[6-((S)-3-Methoxy-pyrrolidin-1-yl)-2-phenyl-pyrimidine-4-carbonyl]-amino}-3-(4-phosphonomethyl-phenyl)-propionyl]-piperazine-1-carboxylic acid butyl ester;

4-((R)-2-{[6-((S)-3-Methoxy-pyrrolidin-1-yl)-2-phenyl-pyrimidine-4-carbonyl]-amino}-5-phosphono-pentanoyl)-piperazine-1-carboxylic acid butyl ester;

4-{(R)-2-[(6-Isopropyl-2-phenyl-pyrimidine-4-carbonyl)-amino]-3-phosphono-propionyl}-piperazine-1-carboxylic acid butyl ester;

4-((R)-2-{[6-(3-Methoxymethyl-azetidin-1-yl)-2-phenyl-pyrimidine-4-carbonyl]-amino}-3-phosphono-propionyl) -piperazine-1-carboxylic acid butyl ester;

4-{(R)-2-[(6-Cyclopentyloxy-2-phenyl-pyrimidine-4-carbonyl)-amino]-3-phosphono-propionyl}-piperazine-1-carboxylic acid ethyl ester;

4-[(S)-2-{[6-((S)-3-Methoxy-pyrrolidin-1-yl)-2-phenyl-pyrimidine-4-carbonyl]-amino}-3-(4-phosphono-phenyl) -propionyl]-piperazine-1-carboxylic acid ethyl ester;

4-[2-{[6-((S)-3-Methoxy-pyrrolidin-1-yl)-2-phenyl-pyrimidine-4-carbonyl]-amino}-2-(4-phosphono-phenyl) -acetyl]-piperazine-1-carboxylic acid ethyl ester;

4-[2-{[6-((S)-3-Methoxy-pyrrolidin-1-yl)-2-phenyl-pyrimidine-4-carbonyl]-amino}-2-(4-phosphono-phenyl)-acetyl]-piperazine-1-carboxylic acid butyl ester;

4-[2-{[6-((S)-3-Methoxy-pyrrolidin-1-yl)-2-phenyl-pyrimidine-4-carbonyl]-amino}-2-(3-phosphono-phenyl)-acetyl]-piperazine-1-carboxylic acid ethyl ester;

4-[2-{[6-((S)-3-Methoxy-pyrrolidin-1-yl)-2-phenyl-pyrimidine-4-carbonyl]-amino}-2-(3-phosphono-phenyl)-acetyl]-piperazine-1-carboxylic acid butyl ester;

4-[2-{[6-((S)-3-Methoxy-pyrrolidin-1-yl)-2-phenyl-pyrimidine-4-carbonyl]-amino}-2-(2-phosphono-phenyl)-acetyl]-piperazine-1-carboxylic acid butyl ester;

4-((R)-2-{[6-(4-Methyl-piperazin-1-yl)-2-phenyl-pyrimidine-4-carbonyl]-amino}-3-phosphono-propionyl)-piperazine-1-carboxylic acid butyl ester;

4-{(R)-2-[(6-Morpholin-4-yl-2-phenyl-pyrimidine-4-carbonyl)-amino]-3-phosphono-propionyl}-piperazine-1-carboxylic acid butyl ester;

N,N'-Bis-(ethoxycarbonylmethyl)-3-{(S)-[6-((S)-3-methoxy-pyrrolidin-1-yl)-2-phenyl-pyrimidine-4-carbonyl]-amino}-4-oxo-4-(4-butoxy-carbonyl-piperazin-1-yl)-butyl-phosphonic acid diamide;

4(R)-3-(Bis-acetoxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4(R)-3-(Bis-propionyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4(R)-3-(Bis-butyryloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

N,N'-Bis-(ethoxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-ethoxycarbonylethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-(methoxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-methoxycarbonyl-2-methyl-propyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-(tert-butyloxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-methoxycarbonylpropyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-methoxycarbonyl-2,2-dimethyl-propyl)-2-{(R)-[6-((S)-3-methoxy-pyrrolidin-1-y1)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-tert-butyloxycarbonylethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-methoxycarbonyl-2-phenyl-ethyl)-2-{(R)-[6-((S)-3-methoxy-pyrrolidin-1-yl)-2-phenyl -pyrimidine-4-carbonyl]-amino}-3-oxo-3-(4-butoxy-carbonyl-piperazin-1-yl)-propyl-phosphonic acid diamide;

N,N'-Bis-((S)-methoxycarbonylphenylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-((S)-1-methoxycarbonylethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-(propyloxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-(isopropyloxycarbonylmethyl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

N,N'-Bis-(2-ethoxycarbonyl-prop-2-yl)-2-{(R)-[6-((S)-3-methoxy-pyrrolidin-1-yl)-2-phenyl-pyrimidine-4-carbonyl]-amino}-3-oxo-3-(4-butoxy-carbonyl-piperazin-1-yl)-propyl-phosphonic acid diamide;

4-((R)-3-(Bis-methoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(Bis-ethoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4(R)-3-(Bis-isopropoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4(R)-3-(Bis-tert-butoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[Bis-(1-ethyloxycarbonyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[Bis-(1-isopropyloxycarbonyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[Bis-(1-cyclohexyloxycarbonyloxy-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4(R)-3-(Diphenoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4(R)-3-[Bis-(5-methyl-2-oxo-[1,3]dioxol-4-ylmethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[Bis-(3-oxo-1,3-dihydro-isobenzofuran-1-yloxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-(Bis-ethoxycarbonylmethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4-((R)-3-[Bis-((S)-1-ethoxycarbonyl-ethoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;

4(R)-3-(Bis-benzyloxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;

4((S)-3-(Bis-acetoxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

4((S)-3-(Bis-butyryloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

N,N'-Bis-((S)-1-ethoxycarbonylethyl)-2-{(S)-[6-((S)-3-methoxy-pyrrolidin-1-yl)-2-phenyl-pyrimidine-4-carbonyl]-amino}-3-oxo-3-(4-ethoxy-carbonyl-piperazin-1-yl)-propyl-phosphonic acid diamide;

4((S)-3-(Bis-ethoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

4(R)-3-(Bis-acetoxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

4(R)-3-(Bis-butyryloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

N,N'-Bis-((S)-1-ethoxycarbonylethyl)-2-{(R)-[6-((S)-3-methoxy-pyrrolidin-1-yl)-2-phenyl-pyrimidine-4-carbonyl]-amino}-3-oxo-3-(4-ethoxy-carbonyl-piperazin-1-yl)-propyl-phosphonic acid diamide;

4-((R)-3-(Bis-ethoxycarbonyloxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid ethyl ester;

4((S)-3-[4-(Bis-butyryloxymethoxy-phosphoryl)-phenyl]-2-{[6-((S)-3-methoxy-pyrrolidin-1-yl)-2-phenyl-pyrimidine-4-carbonyl]-amino}-propionyl)-piperazine-1-carboxylic acid ethyl ester;

N,N'-Bis-((S)-1-ethoxycarbonylethyl)-4-[2-{(S)-[6-((S)-3-methoxy-pyrrolidin-1-yl)-2-phenyl-pyrimidine-4-carbonyl]-amino}-3-oxo-3-(4-ethoxy-carbonyl-piperazin-1-yl)-propyl]-phenyl-phosphonic acid diamide; and 4((S)-3-[4-(Bis-ethoxycarbonyloxymethoxy-phosphoryl)-phenyl]-2-{[6-((S)-3-methoxy-pyrrolidin-1-yl)-2-phenyl-pyrimidine-4-carbonyl]-amino}-propionyl)-piperazine-1-carboxylic acid ethyl ester;

or a pharmaceutically acceptable salt thereof.

13. A medicament comprising the compound of formula I as defined in claim 1 or a pharmaceutically acceptable salt thereof.

14. A pharmaceutical composition comprising the compound of formula I as defined in claim 1 or a pharmaceutically acceptable salt thereof, and one or more pharmaceutically acceptable carriers, diluents or excipients.

15. A method for treating occlusive vascular disorders comprising administering the compound of formula I as defined in claim 1 or a pharmaceutically acceptable salt thereof to a patient in need thereof.

16. A compound of formula I according to claim 2, wherein n represents 1;
or a pharmaceutically acceptable salt thereof.

17. A compound of formula I according to claim 2, wherein n represents 2;
or a pharmaceutically acceptable salt thereof.

18. A compound of formula I according to claim 16, wherein $R^1$ represents unsubstituted phenyl;
or a pharmaceutically acceptable salt thereof.

19. A compound of formula I according to claim 17, wherein $R^1$ represents unsubstituted phenyl;
or a pharmaceutically acceptable salt thereof.

20. A compound of formula I according to claim 18, wherein W represents —$NR^3$— and $R^2$ and $R^3$ form, together with the nitrogen that carries them, a heterocyclic ring of 4 to 6 members wherein the members needed to complete said heterocyclic ring are each independently selected from —$CH_2$—, —$CHR^x$—, —O— and —$NR^y$—, it being understood however that said heterocyclic ring does not contain more than one member selected from the group consisting of —$CHR^x$—, —O— and —$NR^y$—, $R^x$ representing hydroxy, hydroxymethyl, methoxymethyl or methoxy and Ry representing methyl;
or a pharmaceutically acceptable salt thereof.

21. A compound of formula I according to claim 19, wherein W represents —$NR^3$— and $R^2$ and $R^3$ form, together with the nitrogen that carries them, a heterocyclic ring of 4 to 6 members wherein the members needed to complete said heterocyclic ring are each independently selected from —$CH_2$—, —$CHR^x$—, —O— and —$NR^y$—, it being understood however that said heterocyclic ring does not contain more than one member selected from the group consisting of —$CHR^x$—, —O— and —$NR^y$—, $R^x$ representing hydroxy, hydroxymethyl, methoxymethyl or methoxy and Ry representing methyl;
or a pharmaceutically acceptable salt thereof.

22. A compound of formula I according to claim 20, wherein $R^4$ represents $(C_2\text{-}C_4)$alkoxy;
or a pharmaceutically acceptable salt thereof.

23. A compound of formula I according to claim 21, wherein $R^4$ represents $(C_2\text{-}C_4)$alkoxy;
or a pharmaceutically acceptable salt thereof.

24. A compound of formula I according to claim 22, wherein $R^5$ and $R^8$ are identical and represent hydroxy;
or a pharmaceutically acceptable salt thereof.

25. A compound of formula I according to claim 23, wherein $R^5$ and $R^8$ are identical and represent hydroxy;
or a pharmaceutically acceptable salt thereof.

26. A compound of formula I according to claim 22, wherein $R^5$ and $R^8$ are identical and represent each unsubstituted phenyloxy, unsubstituted benzyloxy, a group —O—($CHR^6$)—O—C(=O)—$R^7$, a group —O—($CHR^6$)—O—C(=O)—O—$R^7$, a group —O—($CHR^6$)—C(=O)—O—$R^9$, a group)—NH—($CHR^{10}$)—C(=O)—O—$R^9$ or a group —NH—C($CH_3$)$_2$—C(=O)—O—$R^9$;
or a pharmaceutically acceptable salt thereof.

27. A compound of formula I according to claim 23, wherein $R^5$ and $R^8$ are identical and represent each unsubstituted phenyloxy, unsubstituted benzyloxy, a group —O—($CHR^6$)—O—C(=O)—$R^7$, a group —O—($CHR^6$)—O—C(=O)—O—$R^7$, a group —O—($CHR^6$)—C(=O)—O—$R^9$, a group —NH—($CHR^{10}$)—C(=O)—O—$R^9$ or a group —NH—C($CH_3$)$_2$—C(=O)—O—$R^9$;
or a pharmaceutically acceptable salt thereof.

28. A compound of formula I according to claim 1, wherein $R^1$ represents phenyl;
W represents —$NR^3$— and $R^2$ and $R^3$ form, together with the nitrogen that carries them, a heterocyclic ring of 5 members wherein the members needed to complete said heterocyclic ring are each independently selected from —$CH_2$— and —$CHR^x$—, it being understood however that said heterocyclic ring does not contain more than one —$CHR^x$— group, $R^x$ representing alkoxy;

R$^a$ represents hydrogen;
R$^b$ represents hydrogen;
R$^4$ represents alkoxy;
n represents 1 or 2, V represents a bond, and m represents 0;
R$^5$ and R$^8$ are identical and represent each a group —O—(CHR$^6$)—O—C(=O)—R$^7$, a group —O—(CHR$^6$)—O—C(=O)13 O—R$^7$ or a group) —NH—(CHR$^{10}$)—C(=O)13 O—R$^9$; or
P(O)R$^5$R$^8$ represents

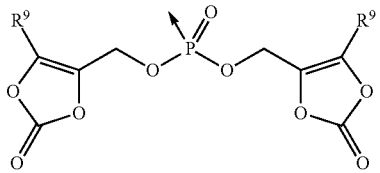

wherein the arrow marks the point of attachment to the remaining part of compounds of formula I;
R$^6$ represents hydrogen;
R$^7$ represents (C$_1$-C$_4$)alkyl;
R$^9$ represents (C$_1$-C$_4$)alkyl;
R$^{10}$ represents hydrogen, (C$_1$-C$_4$)alkyl or unsubstituted phenyl;
or a pharmaceutically acceptable salt thereof.

29. The compound according to claim 1, wherein the compound is 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester;
or a pharmaceutically acceptable salt thereof.

30. The compound according to claim 1, wherein the compound is 4((S)-2-{[6-((S)-3-methoxy-pyrrolidin-1-yl)-2-phenyl-pyrimidine-4-carbonyl]-amino}-4-phosphono-butyryl)-piperazine-1-carboxylic acid butyl ester;
or a pharmaceutically acceptable salt thereof.

31. The compound according to claim 1, wherein the compound is 4-((R)-2-{[6-(2-hydroxymethyl-piperidin-1-yl)-2-phenyl-pyrimidine-4-carbonyl]-amino}-3-phosphono-propionyl)-piperazine-1-carboxylic acid butyl ester;
or a pharmaceutically acceptable salt thereof.

32. The compound according to claim 1, wherein the compound is 4((S)-4-[bis-(isobutyryloxymethoxy)-phosphoryl]-2-{[6-((S)-3-methoxy-pyrrolidin-1-yl)-2-phenyl-pyrimidine-4-carbonyl]-amino}-butyryl)-piperazine-1-carboxylic acid butyl ester;
or a pharmaceutically acceptable salt thereof.

33. The compound according to claim 1, wherein the compound is 4-[(S)-2-{[6-((S)-3-Methoxy-pyrrolidin-1-yl)-2-phenyl-pyrimidine-4-carbonyl]-amino}-3-(4-phosphono-phenyl)-propionyl]-piperazine-1-carboxylic acid butyl ester;
or a pharmaceutically acceptable salt thereof.

34. The compound according to claim 1, wherein the compound is 4-((R)-2-{[6-(3-Methoxymethyl-azetidin-1-yl)-2-phenyl-pyrimidine-4-carbonyl]-amino}-3-phosphono-propionyl)-piperazine-1-carboxylic acid butyl ester;
or a pharmaceutically acceptable salt thereof.

35. The compound according to claim 1, wherein the compound is 4-((R)-2-{[6-(4-Methyl-piperazin-1-yl)-2-phenyl-pyrimidine-4-carbonyl]-amino}-3-phosphono-propionyl)-piperazine-1-carboxylic acid butyl ester;
or a pharmaceutically acceptable salt thereof.

36. The compound according to claim 1, wherein the compound is 4-{(S)-2-[(6-Morpholin-4-yl-2-phenyl-pyrimidine-4-carbonyl)-amino]-4-phosphono-butyryl}-piperazine-1-carboxylic acid butyl ester;
or a pharmaceutically acceptable salt thereof.

37. The compound according to claim 1, wherein the compound is 4(R)-3-(Bis-acetoxymethoxy-phosphoryl)-2-{[6-((S)-3-methoxy-pyrrolidin-1-yl)-2-phenyl-pyrimidine-4-carbonyl]-amino}-propionyl)-piperazine-1-carboxylic acid butyl ester;
or a pharmaceutically acceptable salt thereof.

38. The compound according to claim 1, wherein the compound is 4(R)-3-[Bis-(isopropoxycarbonyloxy-methoxy)-phosphoryl]-2-{[6-((S)-3-methoxy-pyrrolidin-1-yl)-2-phenyl-pyrimidine-4-carbonyl]-amino}-propionyl)-piperazine-1-carboxylic acid butyl ester;
or a pharmaceutically acceptable salt thereof.

39. The compound according to claim 1, wherein the compound is 4((S)-3-[4-(Bis-(ethoxycarbonyloxy-methoxy)-phosphoryl)-phenyl]-2-{[6-((S)-3-methoxy-pyrrolidin-1-yl)-2-phenyl-pyrimidine-4-carbonyl]-amino}-propionyl)-piperazine-1-carboxylic acid ethyl ester;
or a pharmaceutically acceptable salt thereof.

* * * * *

UNITED STATES PATENT AND TRADEMARK OFFICE
CERTIFICATE OF CORRECTION

PATENT NO.       : 8,518,912 B2
APPLICATION NO.  : 12/745358
DATED            : August 27, 2013
INVENTOR(S)      : Eva Caroff et al.

It is certified that error appears in the above-identified patent and that said Letters Patent is hereby corrected as shown below:

On the Title page of the patent, please add the following:
(30) Foreign Application Priority Data
Nov. 29, 2007 (WO) ................... PCT/IB2007/054850

In the Claims:
Claim 8, column 107, line 24, "alkoxy and R$^y$representing alkyl or wherein W represents" should read: alkoxy and R$^y$ representing alkyl or wherein W represents Claim 11, column 107, line 43, "4((S)-2-{[6-((S)-3-methoxy-pyrrolidin-1-yl)-2-phenyl-" should read: 4-((S)-2-{[6-((S)-3-methoxy-pyrrolidin-1-yl)-2-phenyl- Claim 11, column 107, line 46, "4((S)-2-{[6-((S)-3-methoxy-pyrrolidin-1-yl)-2-phenyl-" should read: 4-((S)-2-{[6-((S)-3-methoxy-pyrrolidin-1-yl)-2-phenyl- Claim 11, column 107, line 49, "4((S)-2-{[6-((S)-3-methoxy-pyrrolidin-1-yl)-2-phenyl-" should read: 4-((S)-2-{[6-((S)-3-methoxy-pyrrolidin-1-yl)-2-phenyl- Claim 11, column 107, line 52, "4((S)-2-{[6-((S)-3-methoxy-pyrrolidin-1-yl)-2-phenyl-" should read: 4-((S)-2-{[6-((S)-3-methoxy-pyrrolidin-1-yl)-2-phenyl- Claim 11, column 107, line 55, "4- {(S)-2-[(2-phenyl-6-pyrazol-1-yl-pyrimidine-4-carbo-" should read: 4-{(S)-2-[(2-phenyl-6-pyrazol-1-yl-pyrimidine-4-carbo- Claim 11, column 107, lines 58-59, "4((S)-2-{[6-(4-methyl-pyrazol-1-yl)-2-phenyl-pyrimi-dine-4-carbonyl]-amino}-4-phosphono-butyryl) -pip-" should read: 4-((S)-2-{[6-(4-methyl-pyrazol-1-yl)-2-phenyl-pyrimi-dine-4-carbonyl]-amino}-4-phosphono-butyryl)-pip- Signed and Sealed this
Fifth Day of August, 2014

Michelle K. Lee
*Deputy Director of the United States Patent and Trademark Office*

CERTIFICATE OF CORRECTION (continued)
U.S. Pat. No. 8,518,912 B2

Claim 11, column 108, lines 7-8, "4((S)-2-{[6-(4-methyl-piperazin-1-yl)-2-phenyl-pyrimi-dine-4-carbonyl]-amino}-4-phosphono-butyryl) -pip-" should read:
4-((S)-2-{[6-(4-methyl-piperazin-1-yl)-2-phenyl-pyrimi-dine-4-carbonyl]-amino}-4-phosphono-butyryl)-pip- Claim 11, column 108, line 22, "4((S)-2-{[2-(4-fluoro-phenyl)-6-(S)-3-methoxy-pyrroli-" should read:
4-((S)-2-{[2-(4-fluoro-phenyl)-6-((S)-3-methoxy-pyrroli- Claim 11, column 108, line 26, "4((S)-2-{[6-((S)-3-methoxy-pyrrolidin-1-yl)-2-p-tolyl-" should read:
4-((S)-2-{[6-((S)-3-methoxy-pyrrolidin-1-yl)-2-p-tolyl- Claim 11, column 108, line 29, "4((S)-2-{[2-(2-fluoro-phenyl)-6-(S)-3-methoxy-pyrroli-" should read:
4-((S)-2-{[2-(2-fluoro-phenyl)-6-((S)-3-methoxy-pyrroli- Claim 11, column 108, line 33, "4((S)-2-{[2-(3-fluoro-phenyl)-6-(S)-3-methoxy-pyrroli-" should read:
4-((S)-2-{[2-(3-fluoro-phenyl)-6-((S)-3-methoxy-pyrroli- Claim 11, column 109, line 2, "3-phosphono-propionyl}-pip erazine-1-carboxylic acid" should read:
3-phosphono-propionyl}-piperazine-1-carboxylic acid Claim 11, column 109, line 8, "4-carbonyl]-amino}-3-phosphono-propionyl) -pipera-" should read:
4-carbonyl]-amino}-3-phosphono-propionyl)-pipera- Claim 11, column 109, line 18, "nyl]l-piperazine-1-carboxylic acid butyl ester;" should read:
nyl]-piperazine-1-carboxylic acid butyl ester;

Claim 11, column 109, line 41, "carbonyl]-amino}-3-phosphono-propionyl) -pipera-" should read:
carbonyl]-amino}-3-phosphono-propionyl)-pipera- Claim 11, column 109, line 44, "carbonyl]-amino}-3-phosphono-propionyl) -pipera-" should read:
carbonyl]-amino}-3-phosphono-propionyl)-pipera- Claim 11, column 109, line 46, "4((S)-2-{[6-((S)-3-methoxy-pyrrolidin-1-yl)-2-(3-trifluo-" should read: 4-((S)-2-{[6-((S)-3-methoxy-pyrrolidin-1-yl)-2-(3-trifluo- Claim 11, column 109, line 50, "4((S)-4-[bis-(2,2-dimethyl-propionyloxymethoxy)-phos-" should read: 4-((S)-4-[bis-(2,2-dimethyl-propionyloxymethoxy)-phos- Claim 11, column 109, line 58, "4((S)-4-{bis-[(2,2-dimethyl-propionyloxy)-ethoxy]-phos-" should read: 4-((S)-4-{bis-[(2,2-dimethyl-propionyloxy)-ethoxy]-phos- Claim 11, column 109, line 62, "4(R)-3-[bis-(2,2-dimethyl-propionyloxymethoxy)-phos-" should read:
4-((R)-3-[bis-(2,2-dimethyl-propionyloxymethoxy)-phos-

CERTIFICATE OF CORRECTION (continued)
U.S. Pat. No. 8,518,912 B2

Claim 11, column 110, line 11, "4(R)-3-(bis-isobutyryloxymethoxy-phosphoryl)-2-{[6-" should read:
4-((R)-3-(bis-isobutyryloxymethoxy-phosphoryl)-2-{[6-

Claim 12, column 110, line 51, "nyl) -piperazine-1-carboxylic acid butyl ester;" should read:
nyl)-piperazine-1-carboxylic acid butyl ester;

Claim 12, column 110, line 57, "nyl) -propionyl]-piperazine-1-carboxylic acid ethyl" should read:
nyl)-propionyl]-piperazine-1-carboxylic acid ethyl Claim 12, column 111, line 17, "4(R)-3-(Bis-acetoxymethoxy-phosphoryl)-2-{[6-((S)-3-" should read:
4-((R)-3-(Bis-acetoxymethoxy-phosphoryl)-2-{[6-((S)-3-

Claim 12, column 111, line 21, "4(R)-3-(Bis-propionyloxymethoxy-phosphoryl)-2-{[6-" should read:
4-((R)-3-(Bis-propionyloxymethoxy-phosphoryl)-2-{[6-

Claim 12, column 111, line 25, "4(R)-3-(Bis-butyryloxymethoxy-phosphoryl)-2-{[6-((S)-" should read: 4-((R)-3-(Bis-butyryloxymethoxy-phosphoryl)-2-{[6-((S)-

Claim 12, column 111, line 54, "2-{(R)-[6-((S)-3-methoxy-pyrrolidin-1-yl)-2-phenyl-" should read:
2-{(R)-[6-((S)-3-methoxy-pyrrolidin-1-yl)-2-phenyl- Claim 12, column 111, line 63, "{(R)-[6-((S)-3-methoxy-pyrrolidin-1-yl)-2-phenyl -py-" should read:
{(R)-[6-((S)-3-methoxy-pyrrolidin-1-yl)-2-phenyl-py Claim 12, column 112, line 27, "4(R)-3-(Bis-isopropoxycarbonyloxymethoxy-phospho-" should read:
4-((R)-3-(Bis-isopropoxycarbonyloxymethoxy-phospho- Claim 12, column 112, line 31, "4(R)-3-(Bis-tert-butoxycarbonyloxymethoxy-phospho-" should read:
4-((R)-3-(Bis-tert-butoxycarbonyloxymethoxy-phospho- Claim 12, column 112, line 47, "4(R)-3-(Diphenoxy-phosphoryl)-2-{[6-((S)-3-methoxy-" should read:
4-((R)-3-(Diphenoxy-phosphoryl)-2-{[6-((S)-3-methoxy- Claim 12, column 112, line 51, "4(R)-3-[Bis-(5-methyl-2-oxo-[1,3]dioxol-4-ylmethoxy)-" should read: 4-((R)-3-[Bis-(5-methyl-2-oxo-[1,3]dioxol-4-ylmethoxy)-

Claim 12, column 113, line 1, "4(R)-3-(Bis-benzyloxy-phosphoryl)-2-{[6-((S)-3-meth-" should read:
4-((R)-3-(Bis-benzyloxy-phosphoryl)-2-{[6-((S)-3-meth- Claim 12, column 113, line 5, "4((S)-3-(Bis-acetoxymethoxy-phosphoryl)-2-{[6-((S)-3-" should read:
4-((S)-3-(Bis-acetoxymethoxy-phosphoryl)-2-{[6-((S)-3-

Claim 12, column 113, line 9, "4((S)-3-(Bis-butyryloxymethoxy-phosphoryl)-2-{[6-((S)-" should read:
4-((S)-3-(Bis-butyryloxymethoxy-phosphoryl)-2-{[6-((S)-

CERTIFICATE OF CORRECTION (continued)
U.S. Pat. No. 8,518,912 B2

Claim 12, column 113, line 17, "4((S)-3-(Bis-ethoxycarbonyloxymethoxy-phosphoryl)-2-" should read: 4-((S)-3-(Bis-ethoxycarbonyloxymethoxy-phosphoryl)-2-

Claim 12, column 113, line 21, "4(R)-3-(Bis-acetoxymethoxy-phosphoryl)-2-{[6-((S)-3-" should read: 4-((R)-3-(Bis-acetoxymethoxy-phosphoryl)-2-{[6-((S)-3-

Claim 12, column 113, line 25, "4(R)-3-(Bis-butyryloxymethoxy-phosphoryl)-2-{[6-((S)-" should read: 4-((R)-3-(Bis-butyryloxymethoxy-phosphoryl)-2-{[6-((S)-

Claim 12, column 113, line 37, "4((S)-3-[4-(Bis-butyryloxymethoxy-phosphoryl)-phe-" should read: 4-((S)-3-[4-(Bis-butyryloxymethoxy-phosphoryl)-phe- Claim 12, column 113, line 46, "4((S)-3-[4-(Bis-ethoxycarbonyloxymethoxy-phospho-" should read: 4-((S)-3-[4-(Bis-ethoxycarbonyloxymethoxy-phospho- Claim 20, column 114, line 16, "hydroxymethyl, methoxymethyl or methoxy and Ry repre-" should read: hydroxymethyl, methoxymethyl or methoxy and $R^y$ repre- Claim 21, column 114, line 28, "hydroxymethyl, methoxymethyl or methoxy and Ry repre-" should read: hydroxymethyl, methoxymethyl or methoxy and $R^y$ repre- Claim 26, column 114, line 48, "$R^9$, a group)–NH-(CHR$^{10}$)-C(=O)-O-$R^9$ or a group" should read: $R^9$, a group –NH-(CHR$^{10}$)-C(=O)-O-$R^9$ or a group Claim 28, column 115, lines 8-9, "O-C(=O)13 O-$R^7$ or a group) –NH-(CHR$^{10}$)-C(=O)13 O-$R^9$; or" should read:
O-C(=O)-O-$R^7$ or a group –NH-(CHR$^{10}$)-
C(=O)-O-$R^9$; or Claim 30, column 115, line 35, "pound is 4((S)-2-{[6-((S)-3-methoxy-pyrrolidin-1-yl)-2-" should read: pound is 4-((S)-2-{[6-((S)-3-methoxy-pyrrolidin-1-yl)-2-

Claim 32, column 115, line 45, "pound is 4((S)-4-[bis-(isobutyryloxymethoxy)-phosphoryl]-" should read: pound is 4-((S)-4-[bis-(isobutyryloxymethoxy)-phosphoryl]-

Claim 37, column 116, line 26, "pound is 4(R)-3-(Bis-acetoxymethoxy-phosphoryl)-2-{[6-" should read: pound is 4-((R)-3-(Bis-acetoxymethoxy-phosphoryl)-2-{[6-

Claim 38, column 116, line 32, "pound is 4(R)-3-[Bis-(isopropoxycarbonyloxy-methoxy)-" should read: pound is 4-((R)-3-[Bis-(isopropoxycarbonyloxy-methoxy)-

Claim 39, column 116, line 38, "pound is 4((S)-3-[4-(Bis-(ethoxycarbonyloxy-methoxy)-" should read: pound is 4-((S)-3-[4-(Bis-(ethoxycarbonyloxy-methoxy)-

UNITED STATES PATENT AND TRADEMARK OFFICE
CERTIFICATE OF CORRECTION

PATENT NO. : 8,518,912 B2  Page 1 of 1
APPLICATION NO. : 12/745358
DATED : August 27, 2013
INVENTOR(S) : Caroff et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 311 days.

Signed and Sealed this

Fifteenth Day of September, 2015

Michelle K. Lee
*Director of the United States Patent and Trademark Office*